United States Patent [19]
Maeda et al.

[11] Patent Number: 5,153,444
[45] Date of Patent: Oct. 6, 1992

[54] METHOD AND APPARATUS FOR DETECTING PATTERNS

[75] Inventors: Shunji Maeda; Takashi Hiroi; Hitoshi Kubota; Hiroshi Makihira, all of Kanagawa; Fumiaki Endo, Tokyo, all of Japan

[73] Assignee: Hitachi, Ltd., Tokyo, Japan

[21] Appl. No.: 641,001

[22] Filed: Jan. 14, 1991

Related U.S. Application Data

[63] Continuation-in-part of Ser. No. 454,356, Dec. 21, 1989, Pat. No. 5,038,048.

[30] Foreign Application Priority Data

Sep. 18, 1989 [JP] Japan .................. 1-240080
Jan. 12, 1990 [JP] Japan .................... 2-3587
Jan. 19, 1990 [JP] Japan .................... 2-8114

[51] Int. Cl.$^5$ .............................. G01N 21/88
[52] U.S. Cl. ..................... 250/562; 356/394
[58] Field of Search ............ 250/562, 563, 572; 356/237, 394, 430, 448

[56] References Cited
U.S. PATENT DOCUMENTS

| | | |
|---|---|---|
| 4,449,818 | 5/1984 | Yamaguchi et al. |
| 4,725,722 | 2/1988 | Maeda et al. |
| 4,731,855 | 3/1988 | Suda ........................ 356/237 |
| 4,791,586 | 12/1988 | Maeda et al. |

FOREIGN PATENT DOCUMENTS 60-73310 4/1985 Japan.
8503353 1/1985 PCT Int'l Appl.

Primary Examiner—David C. Nelms
Assistant Examiner—F. Shami
Attorney, Agent, or Firm—Antonelli, Terry, Stout & Kraus

[57] ABSTRACT

A method and apparatus for detecting a defect in a circuit pattern by detecting a gray image signal from each of a plurality of circuit patterns as objects of inspection, which circuit patterns have been fabricated so as to be identical with one another, and detecting a defect as a difference of edge position between two circuit patterns by comparing the detected gray image signal of one circuit pattern with the detected gray image signal of another circuit pattern.

26 Claims, 46 Drawing Sheets

DETECTED IMAGE SIGNAL f(x,y)

PATTERN    SCANNING 3 x 3 PIXELS $o = f(x+1, y-1) - f(x,y)$ $p = f(x, y-1) - f(x,y)$ $q = f(x-1, y-1) - f(x,y)$ $r = f(x-1, y) - f(x,y)$ $s = f(x-1, y+1) - f(x,y)$ $t = f(x, y+1) - f(x,y)$ $u = f(x+1, y+1) - f(x,y)$ $v = f(x+1, y) - f(x,y)$

STORED IMAGE SIGNAL g(x,y)

PATTERN $o' = g(x+1, y-1) - g(x,y)$ $p' = g(x, y-1) - g(x,y)$ $q' = g(x-1, y-1) - g(x,y)$ $r' = g(x-1, y) - g(x,y)$ $s' = g(x-1, y+1) - g(x,y)$ $t' = g(x, y+1) - g(x,y)$ $u' = g(x+1, y+1) - g(x,y)$ $v' = g(x+1, y) - g(x,y)$ if ( f(x-1, y) + f(x+1, y) - 2f(x, y) > Dth
  .or.
  f(x, y-1) + f(x, y+1) - 2f(x, y) > Dth
  .or.
  f(x-1, y-1) + f(x+1, y+1) - 2f(x, y) > Dth
  .or.
  f(x+1, y-1) + f(x-1, y+1) - 2f(x, y) > Dth ) then 1
else
  0

$(\Delta X, \Delta Y) = (0, 0)$
, $(1, -1)$
, $(1, 0)$

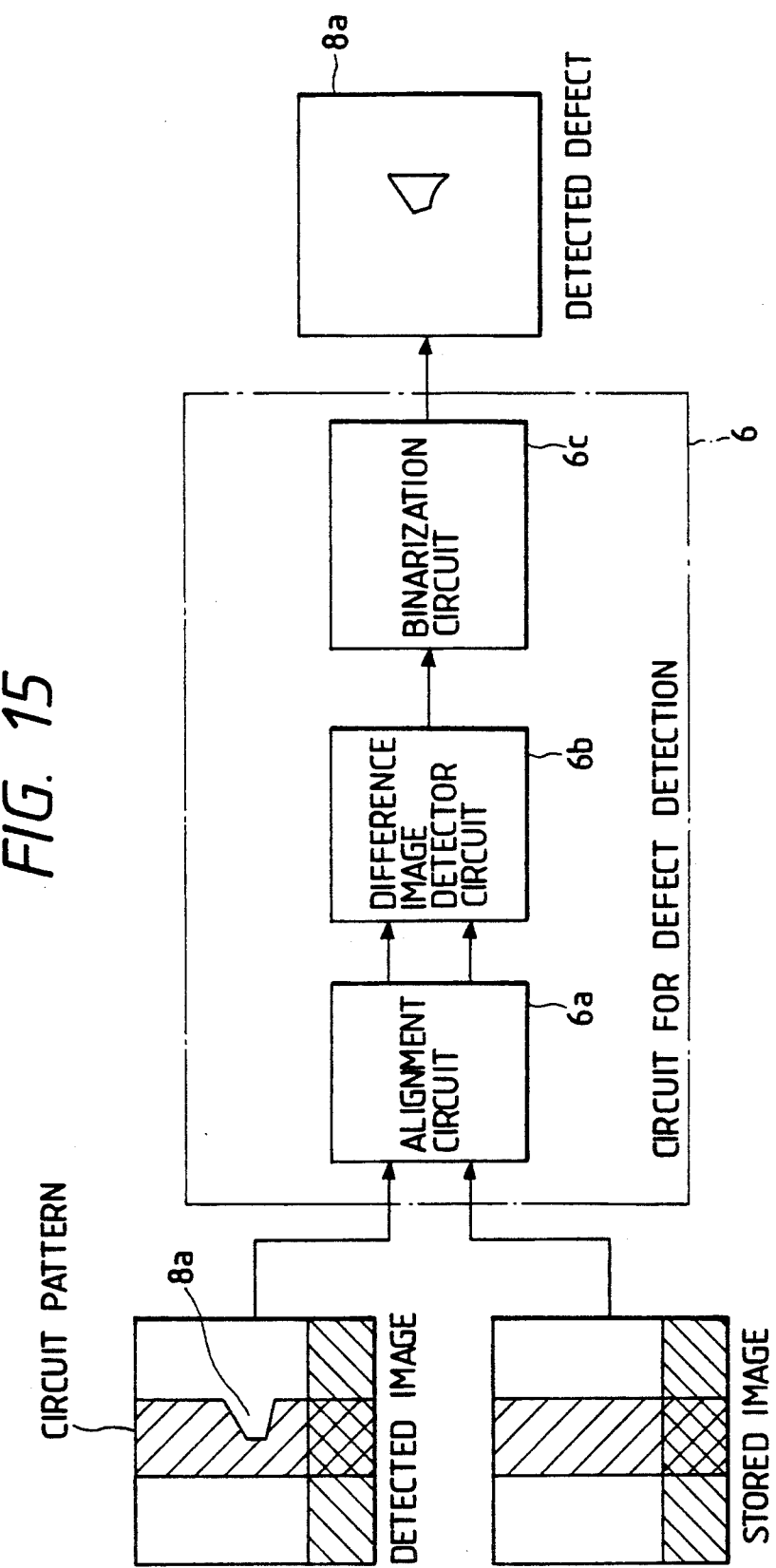

PERSPECTIVE VIEW OF PATTERN F₁

PERSPECTIVE VIEW OF PATTERN G₁

DETECTED SIGNAL WAVEFORMS ALONG A-A', B-B'

DIFFERENCE SIGNAL WAVEFORM

PERSPECTIVE VIEW OF MULTILAYER PATTERN $F_2$

PERSPECTIVE VIEW OF MULTILAYER PATTERN $G_2$

DETECTED SIGNAL WAVEFORMS ALONG A-A', B-B'

SIGNAL WAVEFORM $g_2$ OF MULTILAYER PATTERN $G_2$

SIGNAL WAVEFORM $f_2$ OF MULTILAYER PATTERN $F_2$

DIFFERENCE SIGNAL WAVEFORM $|f_2 - g_2|$

DETECTED SIGNAL WAVEFORM

DERIVATIVE POLARITY WAVEFORM

RESULT OF DETECTION

DETECTED SIGNAL WAVEFORM

DERIVATIVE POLARITY WAVEFORM

RESULT OF DETECTION

DETECTED SIGNAL WAVEFORM

DERIVATIVE POLARITY WAVEFORM

RESULT OF DETECTION

DETECTED SIGNAL WAVEFORM

SECOND DERIVATIVE

BINARIZATION OF SECOND DERIVATIVE

OR DETECTION

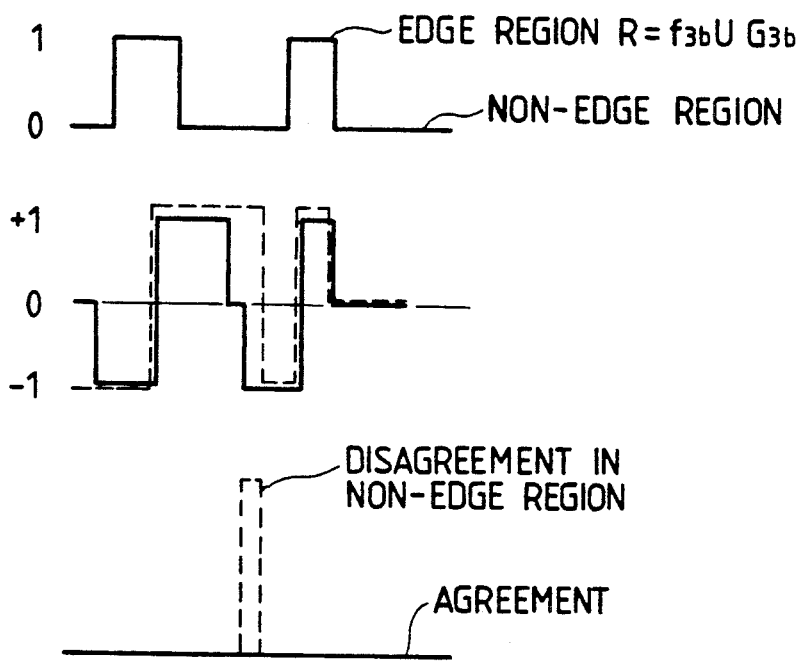

PERSPECTIVE VIEW OF PATTERN F4

PERSPECTIVE VIEW OF PATTERN G4

DETECTED SIGNAL WAVEFORMS ALONG A-A', B-B'

DIFFERENCE SIGNAL WAVEFORM

PERSPECTIVE VIEW OF MULTILAYER PATTERN F2

DEFECT

PERSPECTIVE VIEW OF MULTILAYER PATTERN G2

DETECTED SIGNAL WAVEFORMS ALONG A-A', B-B'

SIGNAL WAVEFORM g2 OF MULTILAYER PATTERN G2

SIGNAL WAVEFORM f2 OF MULTILAYER PATTERN F2

DERIVATIVE POLARITY WAVEFORMS

POSITIVE (+1)

0

NEGATIVE (-1)

RESULT OF DETECTION I

DETECTED SIGNAL WAVEFORMS ALONG A-A' AND B-B' SHIFTED TO THE LEFT

DERIVATIVE POLARITY WAVEFORMS

RESULT OF DETECTION II

RESULT OF FINAL DETECTION (AND OF I AND II)

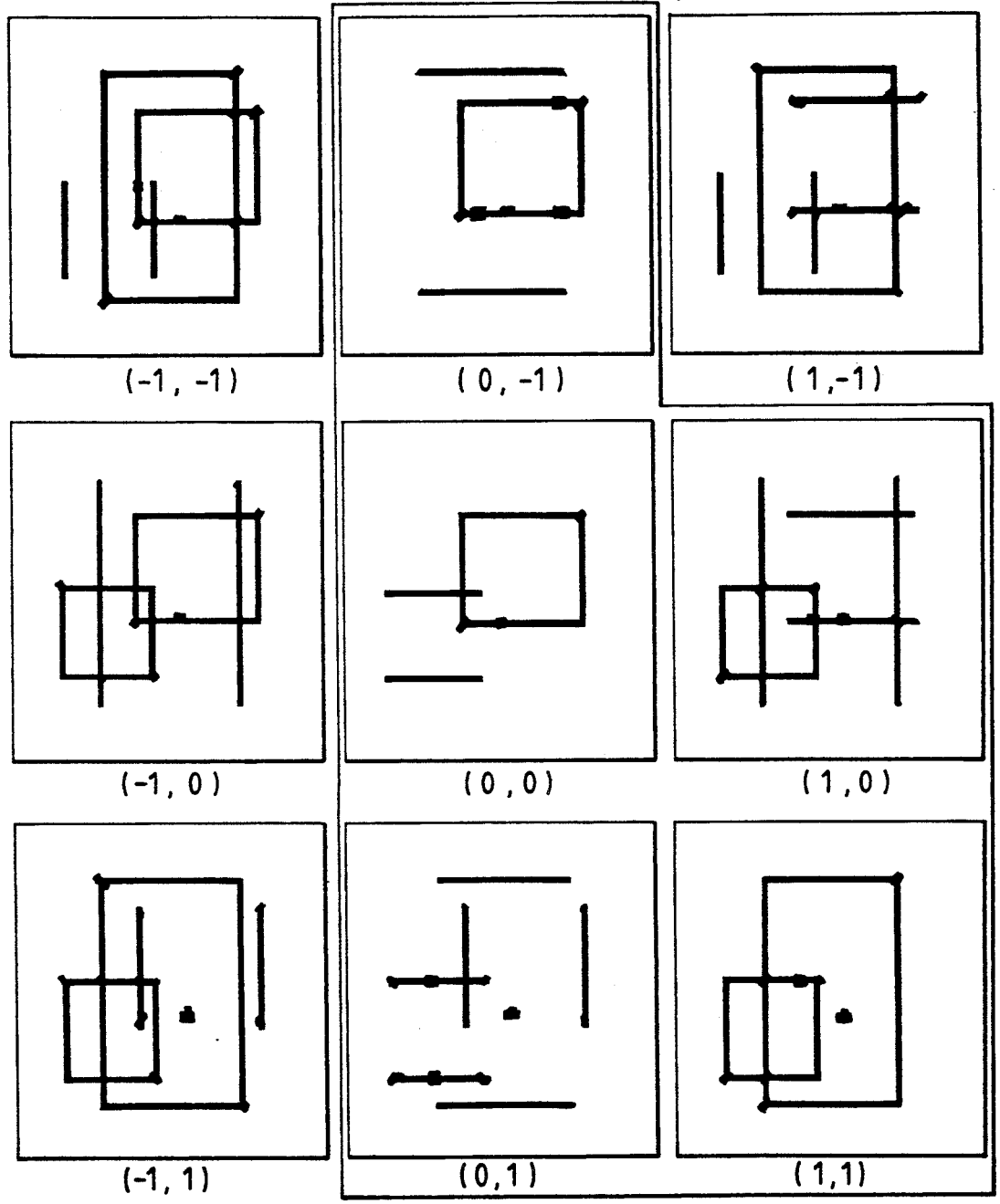

FIG. 27(a)
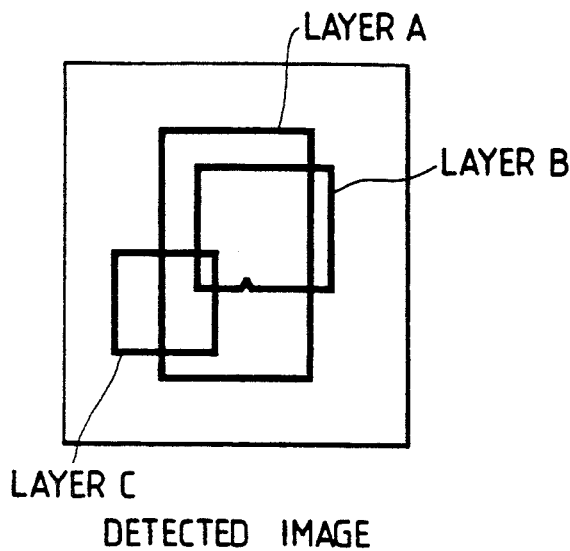
DETECTED IMAGE
FIG. 27(b)
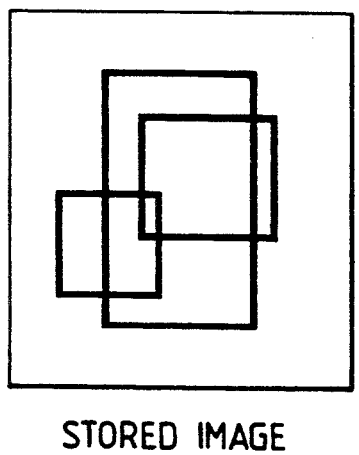
STORED IMAGE
FIG. 27(d)
NUMBER OF DISAGREEING PIXELS $S(\Delta X, \Delta Y)$
|  | -1 | 0 | 1 |
|---|---|---|---|
| -1 | 1379 | 774 | 1107 |
| 0 | 1185 | 555 | 895 |
| 1 | 1334 | 718 | 1045 |
FIG. 27(e)
(WHITE-BLACK INVERTED)
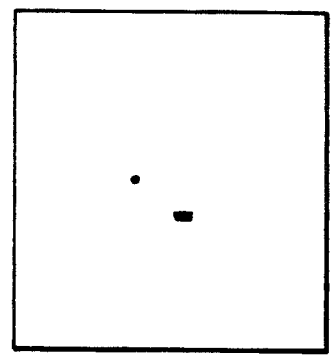
COMMON DISAGREEMENT
FIG. 27(f)
MATCHING EVALUATION VALUE $\Delta S$
| -1444 | (-1166) | -883 |
|---|---|---|
| -1400 |  | (-820) |
| -1337 | (-1054) | (-776) |

FIG. 28(a)
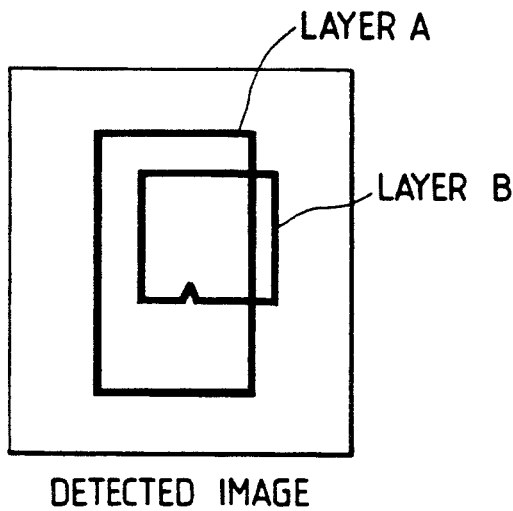
DETECTED IMAGE
LAYER A
LAYER B
FIG. 28(b)
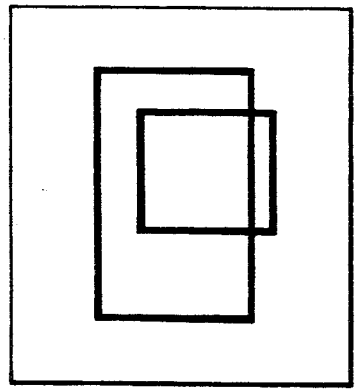
STORED IMAGE
FIG. 28(d)
NUMBER OF DISAGREEING PIXELS $S(\Delta X, \Delta Y)$
|    | -1   | 0   | 1   |
|----|------|-----|-----|
| -1 | 1228 | 772 | 964 |
| 0  | 873  | 399 | 587 |
| 1  | 925  | 441 | 633 |
FIG. 28(e)
(WHITE-BLACK INVERTED)
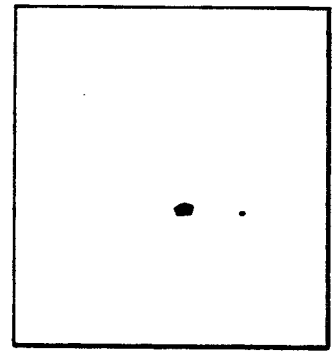
COMMON DISAGREEMENT
FIG. 28(f)
MATCHING EVALUATION VALUE $\Delta S$
| -1393 | -1123 | -837 |
|-------|-------|------|
| -1084 |       | -512 |
| -759  | -467  | (-203) |

DEFECT

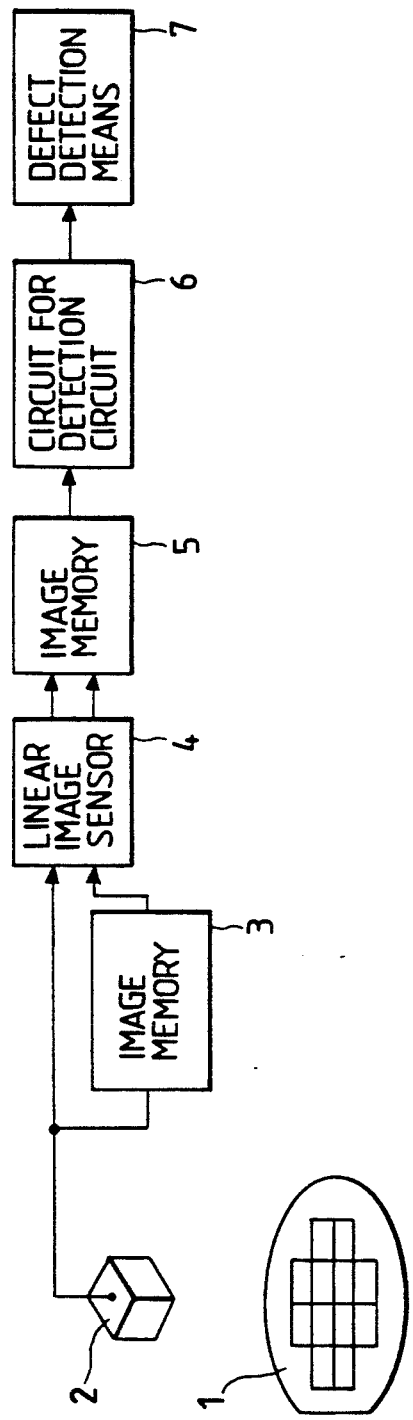
FIG. 37
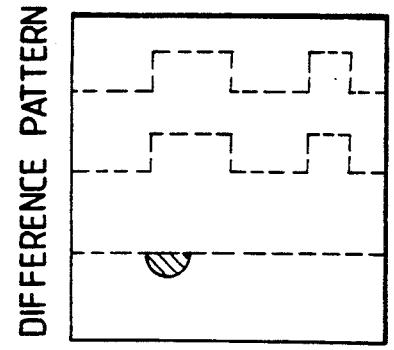
FIG. 38(c) DIFFERENCE PATTERN
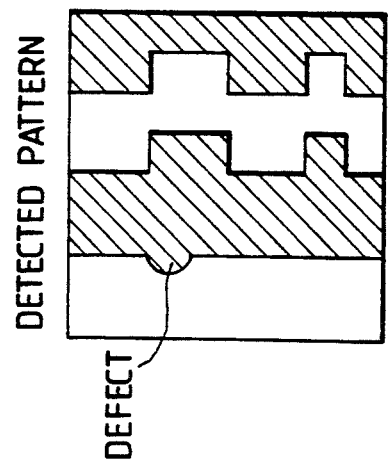
FIG. 38(b) DETECTED PATTERN
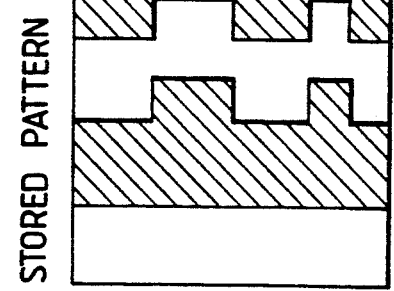
FIG. 38(a) STORED PATTERN

NORMAL PORTION

STORE PATTERN | DETECTED PATTERN

DEFECTIVE PORTION — DEFECT

STORE PATTERN | DETECTED PATTERN

DIFFERENCE IMAGE IN NORMAL PORTION

SIZE OF ERROR

DIFFERENCE IMAGE IN DEFECTIVE PORTION (0,0)

(1,0)

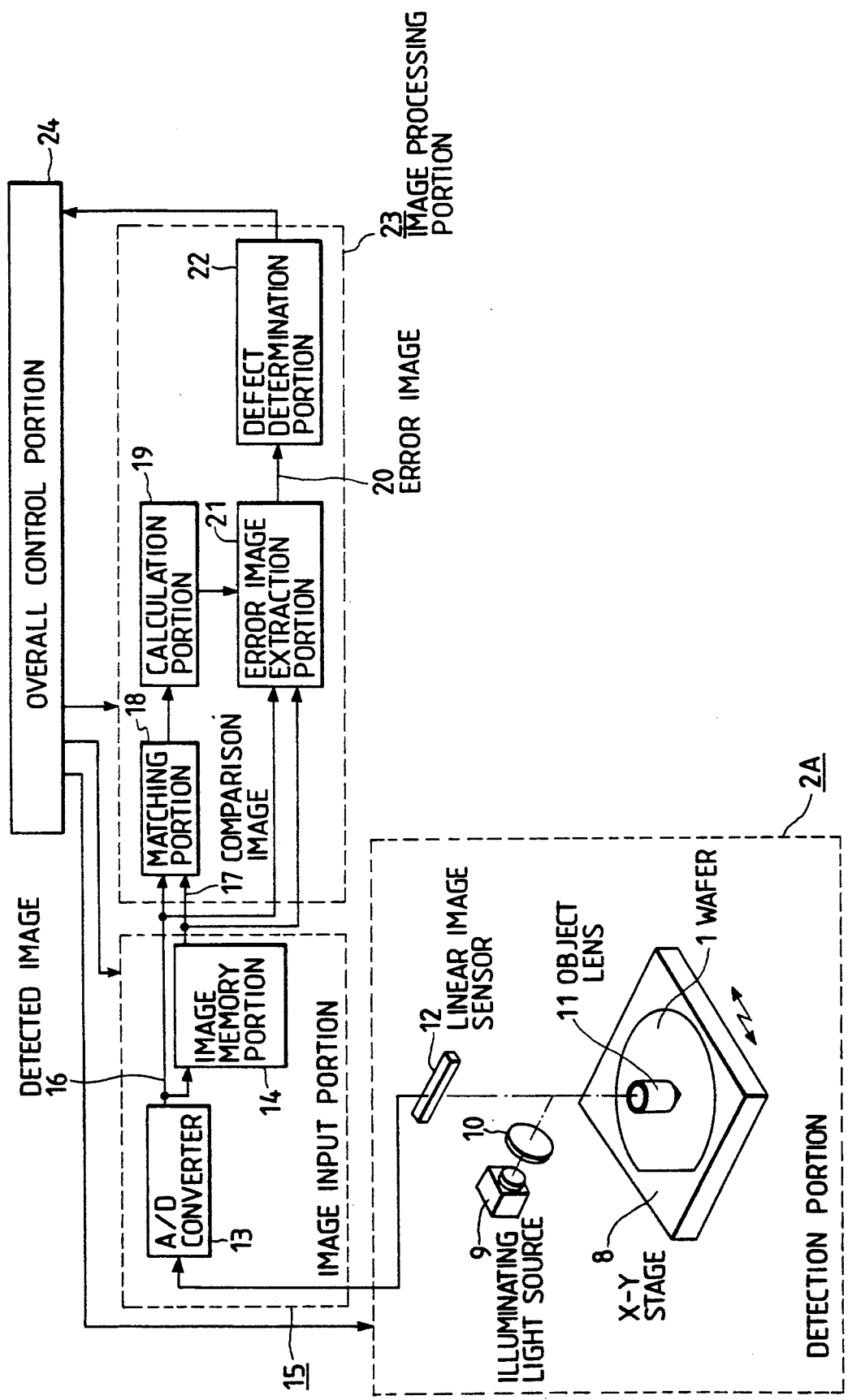

METHOD AND APPARATUS FOR DETECTING PATTERNS

CROSS-REFERENCE TO RELATED APPLICATIONS

This application is a continuation-in-part of copending application Ser. No. 454,356, filed Dec. 21, 1989, now U.S. Pat. No. 5,038,048, the subject matter of which is incorporated by reference herein

BACKGROUND OF THE INVENTION

The present invention relates to a method and apparatus for detecting patterns and defects therein as in circuit patterns formed on an LSI, TFT (Thin Film Transistor), or the like as objects of inspection. The defects may, for example, be defects in shape, foreign matter, discolorations defects or the like.

Integrated circuits such as LSI are tending to increase in packaging density and are provided with more miniaturized components. In fabricating such miniaturized circuit patterns, detection of defects in the patterns has great importance in evaluation of the quality of the products. It is already difficult to detect defects by visual inspection and to use a large amount of manpower for detecting the defects by visual inspection is not sufficient and, hence, there is increasing demand for automated defect detection.

A method and apparatus for converting image information of the surface of a semiconductor device obtained by an optical microscope or electronic microscope into an electric signal using a camera tube or image pickup device and subjecting the signal to certain signal processing to thereby detect defects in the semiconductor device is known as described, for example, in Semiconductor World (June, 1984) pp. 112 to 119, or Japanese Laid-open Patent Publication No. 59-192943. Such an apparatus is illustrated in FIG. 14, wherein a circuit pattern on a wafer 1 illuminated by a lamp 2 is enlarged and detected by an objective lens 3 and an image sensor 4. The thus detected gray image of the circuit pattern is compared in a defect detection device 6 with the image of a chip 7a (adjoining chip) detected and stored in an image memory 5 one step before and, thereby, the presence of a defect is determined. The detected image is simultaneously stored in the image memory 5 (turned into a stored image) and used for inspection by comparison for the next chip 7b. A block diagram arrangement of the defect detection device 6 for determination of existence of a defect is shown in FIG. 15. The detected image and the stored image are aligned with each other in an alignment circuit 6a and a difference image between the aligned detected image and stored image is obtained by a difference image detector circuit 6b. This signal is binarized by a binarization circuit 6c for detecting a defect. Thus, a defect 8a is detected with the described arrangement.

More minutely arranged LSI's are being fabricated and there are also appearing submicron LSI's such that it is becoming more difficult for the above-described apparatus to detect minute defects. If the miniaturization of components and multilayer structure of circuit patterns on LSI's are developed still more in the future, it is assumed that detection of defects on the order of 0.1 to 0.3 μm in such complicated and miniaturized multilayer patterns will become necessary, and such detection cannot be reliably performed with use of only the aforementioned apparatus.

A method for comparison of patterns is also disclosed in a paper entitled, "Computer Controlled Imaging System for Automatic Hybrid Inspection" (Solid State Technology/October 1980). According to the method described therein, every time a pattern is detected, the detected pattern is temporarily stored and simultaneously compared with a pattern that was detected and stored immediately before, whereby detection of a defect in the pattern is achieved. More specifically, the patterns as the object of pattern detection may be patterns on semiconductor wafers for memory LSI's, patterns for TFT, patterns on printed-wiring boards, patterns on ceramic boards, and patterns of masks and reticles used in the processes fabricating the above mentioned devices. Hereinafter, description will be made about patterns on semiconductor wafers as an example, but the same description will equally be applicable to other patterns.

The patterns as the units of chips on a semiconductor wafer are finally separated into individual chips. Before being separated, a large number of chips as individual products are mounted on one slice of the wafer. The patterns of the chips are all made alike, but each pattern as a unit of a chip is formed of a pattern portion in which memory cells or the like formed in identical patterns are periodically arranged at regular intervals and a pattern portion in which peripheral circuits or the like are arranged less periodically.

Now, the principle of a method conventionally practiced for detecting defects in patterns will be further described with reference to FIG. 35, taking a pattern on a chip, as an example, and which corresponds to the patterns illustrated in FIG. 15. In this method, in view of the fact that all chips have the same patterns and, within each chip, patterns corresponding to its cells are periodically arranged at regular intervals, when a pattern on one chip is detected, the pattern is stored, and then, when a pattern on another chip, which should be equal to the previously detected pattern, is detected, the pattern is compared with the stored pattern, and thereby, a defect is detected. FIGS. 35(a), (b), and (c) respectively show a stored pattern, a detected pattern, and a difference between the patterns (difference obtained as the result of the comparison), and it is arranged such that there occurs virtually no difference between patterns when there is no defect in either of the stored pattern and the detected pattern. However, when there is a defect present in either of the patterns, a difference between patterns is produced at the position where the defect is present. Thus, it is arranged such that a pattern defect is detected by detecting the portion where such a difference between patterns is produced. At that time, if there is produced a pattern difference, it can be determined that a defect is present in either of the patterns, but it cannot be determined in which of the patterns the defect is present. In practice, however, there are various ways to determine that, but the explanation thereof is omitted herein.

The pattern on one chip was compared with that on another chip in the foregoing method (which method will hereinafter be called the "two-chip comparison method"). It can also be arranged such that pattern comparison is carried out for cell patterns within the same chip (which method will hereinafter be called the "two-cell comparison method"). The above described method of comparison is not only applicable to patterns on a wafer, but is also applicable with relative ease to a general pattern to be defined as a superordinate concept of the pattern, although there is no such concept as chips or cells involved therein, such as members having the same patterns or a member in which the same patterns are periodically arranged at regular intervals.

Generally, in the two-cell comparison method, the error level detected in a normal portion is lower than that in the two-chip comparison method and, hence, the discrimination between a defective pattern portion and a normal pattern portion in the two-cell comparison method is easier. FIG. 36(a) shows a detected signal waveform of a pattern obtained along a pattern detecting line, FIG. 36(b) and FIG. 36(c) respectively show a waveform for the two-cell comparison and a waveform for the two-chip comparison to be compared with the detected waveform, FIG. 36(d) and FIG. 36(e) respectively show a waveform obtained two-chip comparison method. As apparent from these waveforms, the signal level of the difference signal a the portion of the normal pattern is relatively low in the two-cell comparison method, while that in the two-chip comparison method is high. This is because, in the two-cell comparison method, the patterns are compared within the same chip and, in addition, one pattern is compared with another pattern located quite close to it and, hence, the factors which produce errors in the normal pattern portion are not so great. As a result, the difference waveform at the normal pattern portion detected in the two-cell comparison method is at a relatively lower signal level while that detected in the two-chip comparison method is at a relatively higher level. Meanwhile, the signal levels of the difference signals at the portion including a defect obtained by the two-cell comparison method and by the two-chip comparison method are considered virtually of the same level. Accordingly, when discriminating a portion with a normal pattern from a portion with a defective pattern by binarizing the signal levels of the difference signals, the threshold value tolerance used for the discrimination can be made larger in the two-cell comparison method than in the two-chip comparison method and, therefore, the discrimination between the portion with a defective pattern and the portion with a normal pattern becomes easier in the two-cell comparison method than in the two-chip comparison method.

Conventionally, in detecting a defect in a pattern on a wafer, for example, the defect detection is performed either by only applying the two-chip comparison method over the entire surface of the wafer or by specifying the coordinate for the two-cell comparison and applying the two-cell comparison method to the portion where two-cell comparison is applicable and the two-chip comparison method to the portion where two-cell comparison method is not applicable. Here, the portion where the two-cell comparison is applicable is such a portion within a chip defined as the portion of a pattern where memory cells are periodically arranged at intervals of a predetermined pitch, and the portion where the two-cell comparison is not applicable is such a portion defined as the portion of a pattern within a chip other than the portion where two-cell comparison is applicable, or, more particularly, as the portion where patterns are arranged less periodically, such as a portion where peripheral circuits are formed and, hence, detection of a defect in the patterns is possible only by the two-chip comparison method.

Pattern defect detection has conventionally been performed as described above, but whichever method has been used, there has been some problem or inconvenience particularly related to each respective method. That is, when the two-chip comparison method is used, since a pattern defect is detected by the two-chip comparison method even at the portion where two-cell comparison is applicable, the threshold value tolerance inevitably becomes small. On the other hand, when the two-cell comparison method is used, preprocessing is required so as to set up in advance the coordinate of the portion where the two-cell comparison is applicable, which differs with the different types of wafers.

Another prior art pattern recognition arrangement is described in Japanese Laid-Open Patent Publication No. 57-196377, includes means for detecting a pattern, means for storing the detected pattern, means for pixelwise alignment of the pattern detected and stored one step before with the pattern currently detected, and means for extracting and evaluating the error between the aligned two patterns, whereby it is adapted such that a defect in the pattern is recognized through the comparison. The objects of pattern recognition include a pattern on a memory LSI as shown in FIG. 38, a pattern of TFT, a pattern on a printed-wiring board, a pattern on a ceramic board, and patterns of masks and reticles used in the fabricating processes of the above mentioned devices. In view of the fact that all the chips have completely the same patterns, first, a pattern is detected and stored, and then another pattern, which should be the same as the previous one, is detected, the stored pattern is brought into pixel-wise alignment with the detected image (which pixel-wise alignment is a state where, having differences between the detected pattern and the stored pattern summed up for pixels all over the area of the image and the summation performed with the stored pattern shifted one pixel at a time relative to the detected pattern, the images are brought into a position where the sum total of the differences becomes a minimum, i.e., the two images are best aligned), and the errors between the two patterns in alignment are extracted and evaluated. When there is no defect in either pattern, the difference between the patterns is small, but when there is a defect in either of the patterns, a considerable difference is produced between the patterns at the defective portion. Therefore, by comparing the patterns and detecting the position where an error is produced, a pattern defect can be recognized. At that time, if a difference is detected through the comparison, it can be said that there is a defect in either of the patterns, but it is not possible to determine in which pattern the defect is present.

A normal pattern on a wafer as the object of inspection exhibits different patterns from location to location due to various error causing factors. Therefore, a difference between patterns can not always be determined to be a defect, and it becomes difficult to discriminate a small defect from an error in the normal portion. The distinction between a defect and an error in the normal portion will first be defined. An error in the normal portion is defined to be such that the same pattern in the vicinity of the portion in question has also a similar error. On the other hand, a defect is defined to be a localized difference and such that the same pattern in the vicinity has no similar error. It is further assumed that an allowable dimensional error in the normal portion is larger than the minimum defect size to be recognized. Of course there are some exceptions, but such exceptions are not considered herein.

Utilizing the above definitions, a method in which a difference between patterns is determined to be a defect will encounter a problem as shown in FIG. 39. All patterns in FIG. 39 are shown in binary images for simplicity of explanation. FIG. 39(a) shows a case where a stored pattern and a detected pattern are compared in a normal portion having an allowable dimensional error, FIG. 39(b) shows a case where a stored normal pattern and a detected defective pattern are compared for patterns involving a defect of the least size to be recognized, and FIG. 39(c) and FIG. 39(d) respectively show the difference between the patterns in FIG. 39(a) and that in FIG. 39(b). Comparing FIG. 39(c) with FIG. 39(d), the area of the difference between the patterns in the normal portion is larger than the area of the difference between the patterns in the defective portion, and this makes the detection of a defect difficult. As such, a method must be devised to easily perform discrimination between the normal pattern with an error and a defect and to recognize features of patterns such as a discrepancy between patterns or deformation of a pattern can be easily performed.

SUMMARY OF THE INVENTION

An object of the present invention is to provide a method and an apparatus for pattern recognition and for detecting defects in patterns such as circuit patterns as an object of inspection which is capable of detecting only actual defects with high reliability and accuracy.

Another object of the present invention is to detect defects in circuit pattern without erroneously detecting, as defects, such irregularities as three-dimensional differences in shape due to a change in the film thickness or conditions of the down slope of the pattern, interlayer slippages, or sampling errors at the time of inspection, capable of satisfactorily meeting miniaturization of components and multilayer structure mounted on LSI's, and, especially, capable of detecting minute defects on the order of 0.1 to 0.3 μm.

Another object of the present invention is to provide a method and an apparatus for detecting defects in circuit patterns in which the sensitivity of defect detection is automatically adjusted in accordance with the conditions of fabrication of the shapes of the patterns as the object of inspection.

A further object of the present invention is to provide a method and an apparatus for detecting defects in circuit patterns capable of accurately detecting the dimension of a defect.

A still further object of the present invention is to provide a method and apparatus for detecting a defect in a pattern capable of performing the pattern defect detection with the two-cell comparison method and the two-chip comparison method switched to each other automatically, without the need for specifying the coordinate.

Another object of the present invention is to provide a method and apparatus for enabling pattern recognition and for enabling discrimination between a normal pattern with an error and a defect.

In accordance with the present invention, the method and apparatus provides for comparing detected and reference images representing previously detected images of circuit patterns for detecting defects in shape as positional discrepancies of the circuit patterns on the detected images. The present invention enables detection of a relatively large defect on the order of 0.5 μm, a discoloration defect, and foreign matter according to differences in gray level. Further, the present invention provides that images are aligned with each other depending on the number of disagreeing pixels detected as positional discrepancies.

According to a feature of the present invention, detection of minute defects even if shapes of gray waveforms of the detected images at normal portions are considerably different from each other is enabled. Consequently, a gray-level difference of circuit patterns, difference in the condition of down slope of the edges, interlayer slippage, and sampling errors at the time of inspection are prevented from being erroneously detected as defects. Further, since the accuracy in alignment between images are enhanced, it is possible to detect even very minute defects. Also, not only the defects in shape of circuit patterns but also such defects as discoloration can be detected without fail. Additionally, not only the presence of defects but also their dimension can be accurately detected.

In accordance with another feature of the present invention, pattern matching comparison is performed between a reference image, or detected image, and each of images obtained at coordinates for two-cell comparison and images obtained at coordinates for two-chip comparison, as plural comparison images, at the same time, no matter whether the portion of inspection is a portion where two-cell comparison is applicable or a portion where two-chip comparison is not applicable, the image providing the highest degree of agreement out of the results of the comparison is selected, and, then detection of a pattern defect between the thus selected image and the reference image, or detected image is detected.

According to a further feature, the reference image, or detected image, and each of the plural comparison images are simultaneously subjected to pattern matching comparison and, according to the results of the comparison, one of the comparison image patterns, or more particularly the comparison image pattern providing the highest degree of agreement, is selected, and detection of a pattern defect is performed between the selected image and the reference image, or detected image. At that time, the plural comparison image patterns include plural patterns at the coordinates for two-chip comparison and plural pattern at the coordinates for two-cell comparison, and the pattern matching comparison is performed between the reference image, or detected image, and the plural patterns at the coordinates for two-chip comparison having the coordinates thereof apart from the coordinate of the reference image, or detected image, by integer multiples of the chip pitch, and between the reference image, or detected image, and the plural patterns at the coordinates for two-cell comparison having the coordinates thereof apart from the coordinate of the reference image, or detected image, by integer multiples of the cell pitch.

As a consequence of the foregoing, the present invention provides that the two-cell comparison is automatically selected at the portion where two-cell comparison is applicable and the two-chip comparison is automatically selected at the portion where two-cell comparison is not applicable. More specifically, in the portion where two-cell comparison is applicable, there are present both the patterns capable of being subjected to two-cell comparison at the coordinates for two-cell comparison and the patterns capable of being subjected to two-chip comparison at the coordinates for two-chip comparison, but the two-cell comparison is selected there because the patterns capable of being subjected to two-cell comparison have weaker error producing factors in the processing than the patterns capable of being subjected to two-chip comparison and, hence, has a higher degree of agreement with the reference image, or detected image. In the portion where two-cell comparison is not applicable, however, the patterns at the coordinates for two-cell comparison include patterns not completely unable to be subjected to two-cell comparison, while the patterns at the coordinates for two-chip comparison include patterns capable of being subjected to two-chip comparison and, hence, the patterns capable of being subjected to two chip comparison have a larger degree of agreement when compared with the pattern of the reference image, or detected image, and thus, the two-chip comparison is selected there.

In accordance with other features of the present invention, a plurality of shifted images in alignment with a high degree of agreement are selected for two patterns and errors between two patterns are calculated for each pixel using values at all the shifted positions and values in the vicinity thereof, whereby an error image is generated and, depending thereon, pattern recognition is performed.

The above and other objects, features, and advantages of the present invention will become more apparent from the following description when taken in connection with the accompanying drawings which show, for the purposes of illustration only, several embodiments in accordance with the present invention.

BRIEF DESCRIPTION OF THE DRAWINGS

FIG. 14 and FIG. 15 are block diagrams relating to prior arts arrangements;

FIGS. 21(a) to (e) are diagrams for explaining polarity comparison in which second derivatives are also used;

FIGS. 27(a) to (f) are diagrams showing an experiment (three-layer pattern) for compensating for interlayer alignment error by shifting images;

FIGS. 28(a) to (f) are diagrams showing an experiment (two-layer pattern) for compensating for interlayer alignment error by shifting images;

FIG. 37 is a block diagram showing the principle for pattern recognition in accordance with the present invention;

FIGS. 38(a) to 38(c) are diagrams showing the principle for detecting a pattern defect according to a general pattern comparison method, of which FIG. 38(a) shows a stored pattern, FIG. 38(b) shows a detected pattern with a defect, and FIG. 38(c) shows a pattern taken as the difference between the patterns (a) and (b);

FIGS. 39(a) to 39(d) are examples of patterns, of which FIG. 39(a) is a normal portion with an error of allowable dimension, FIG. 39(b) is a defective portion, FIG. 39(c) is a difference image in FIG. 39(a), and FIG. 39(d) is a difference image in FIG. 39(b)

FIG. 41 is a block diagram showing another embodiment of the present invention;

DETAILED DESCRIPTION OF THE PREFERRED EMBODIMENTS

Figure 1:
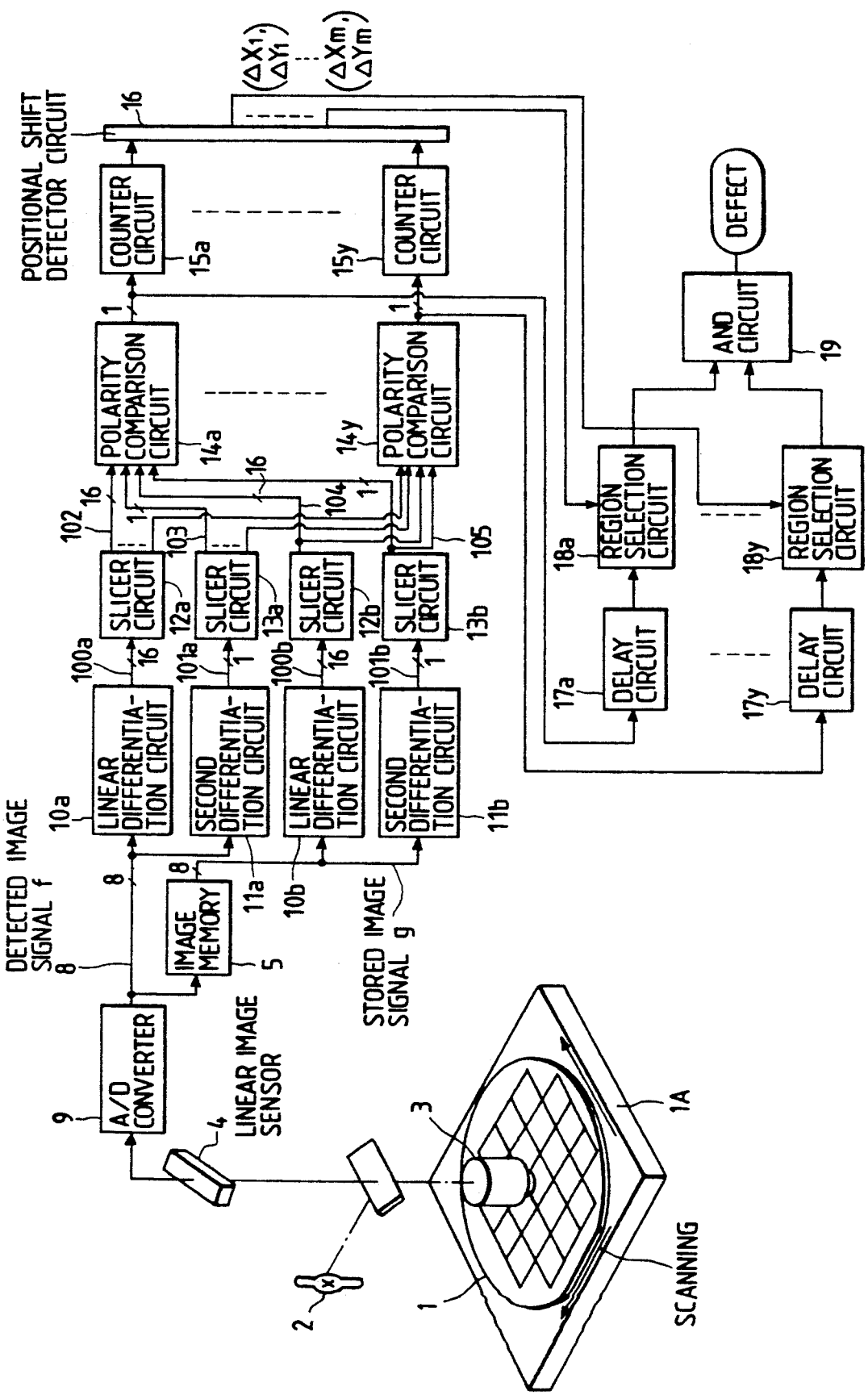
FIG. 1 is a schematic block diagram showing an embodiment of the present invention for detecting defects in circuit patterns.

An embodiment of the present invention will now be described with reference to FIG. 1. As a photoelectric transducer 4 for converting an optical image of the pattern to be inspected (circuit pattern) into an electric signal, any device such as a linear image sensor and a TV camera can be used, but the present embodiment employs a linear image sensor. By the self scanning of the linear image sensor and by the movement of an X-Y table 1A orthogonal to the scanning direction, the two-dimensional circuit pattern on a wafer 1 with the patterns to be inspected formed thereon is detected. An analog signal (video signal) detected by the linear image sensor 4 is converted by an A/D converter 9 into a digital signal 8, for example, of eight bits, and the detected gray level image signal f is compared with the signal g (stored gray level image signal) of the adjoining chip previously detected and stored in the image memory 5 and, thus, existence of a defect is determined. More specifically, as shown in FIG. 2, the circuit pattern at a position 7d inside a chip 7 of the wafer is detected (detected image signal f) and this is compared with a circuit pattern at the corresponding position 7c of the adjoining chip stored in the image memory 5 (stored image signal g) to thereby detect the defect.

Figure 2:
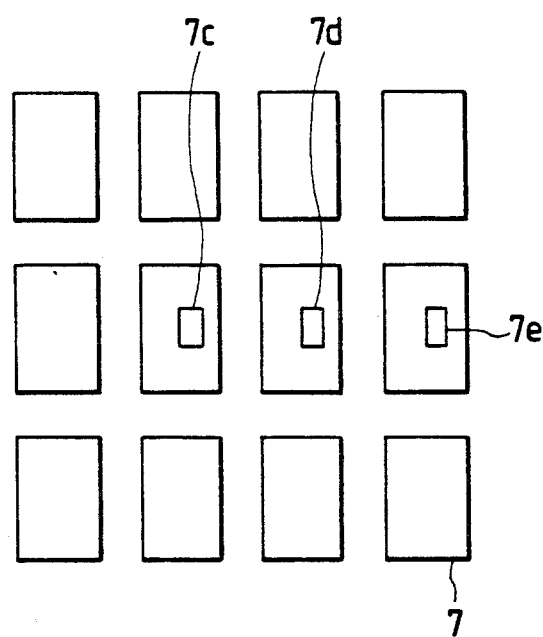
FIG. 2 is an explanatory diagram of comparison of two chips.
Figure 3A:
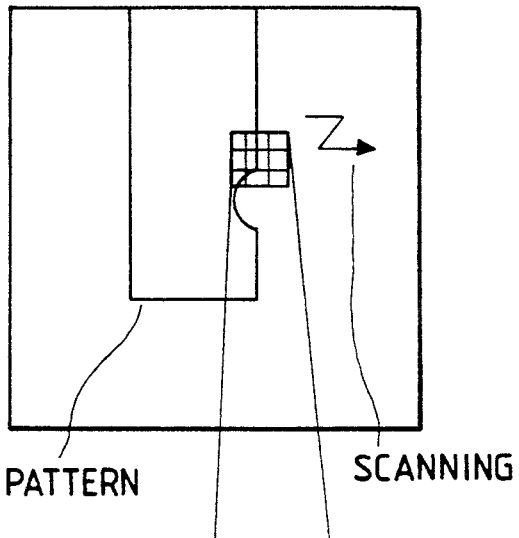
FIGS. 3a and 3b is a diagram showing an example of linear differentiation performed in a linear differentiation circuit shown in FIG. 1.
Figure 3B:
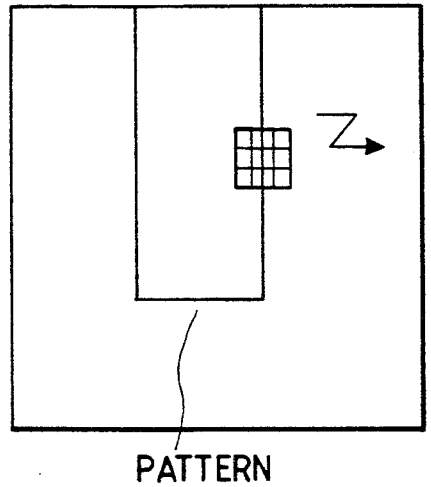
Figure 4:
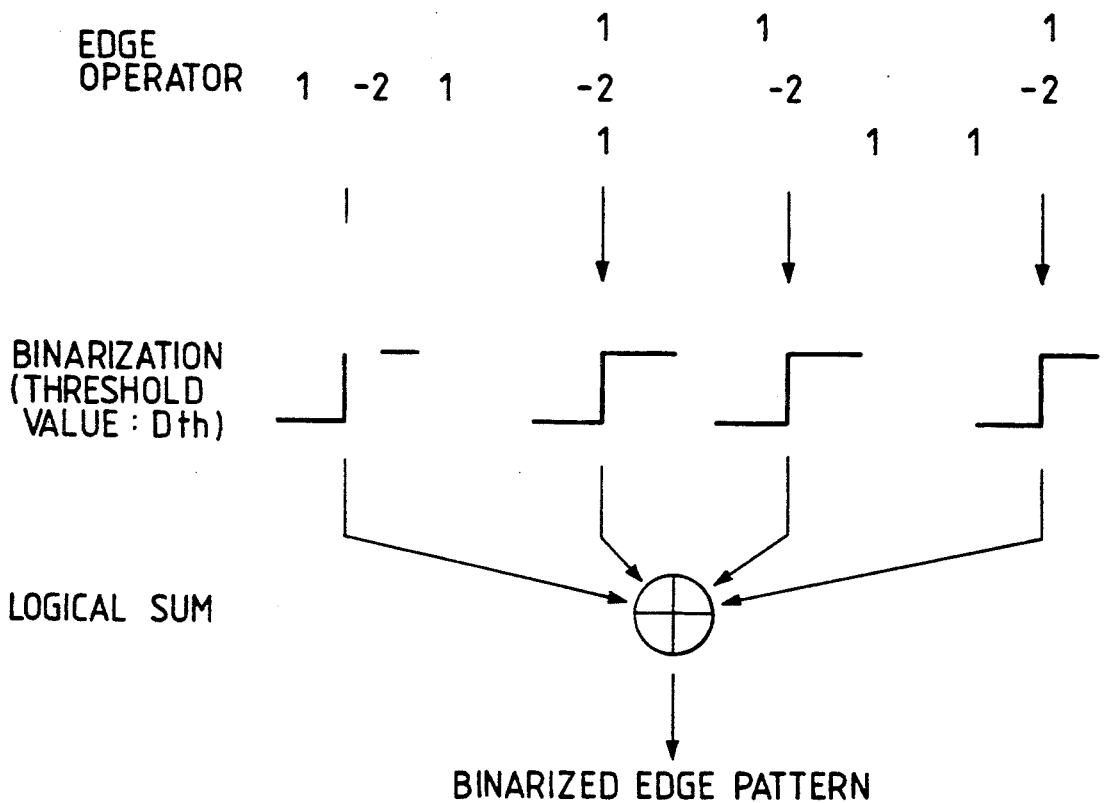
FIG. 4 is a diagram showing an example of second differentiation performed in a second differentiation circuit shown in FIG. 1.

Referring to FIG. 1, a detected image signal f and a stored image signal g, each being formed, for example, of eight bits, are sequentially subjected, for each pixel, to linear differentiation and second differentiation in linear differentiation circuits 10a and 10b and second differentiation circuits 11a and 11b. The linear differentiation circuits 10a and 10b, as shown in FIG. 3, sequentially slice 3×3 pixels from the detected and stored images and obtain linear derivatives in eight directions o, p, ..., v and o', p', ..., v', and output signals 100a and 100b, for example, of 16 bits formed of the polarities (1, 0) of the linear derivatives and the values (1, 0) obtained by binarizing the absolute values of the linear derivatives. In this case, "1" of the polarity represents the positive polarity and "0" represents the negative polarity. The second differentiation circuits 11a and 11b apply operators (1, −2, 1) to each pixel of the images and binarize the results with a threshold value Dth as shown in FIG. 4, thereby putting a dark region into "1" and another region into "0", and output signals 101a and 101b, for example, of one bit. Then, the output of the linear differentiation circuits 10a and 10b and the output of the second differentiation circuits 11a and 11b are sliced by slicer circuits 12a, 12b, 13a, and 13b. The slicer circuits 12a and 13a slice a region, for example, of 5×5 pixels and, thereby, provide a state where pixels are shifted by ±2 pixels. The slicer circuits 12b and 13b are synchronized with the position in the center of the above 5×5 pixels. Then, the linear derivatives and second derivatives of the detected image signals shifted by ±2 pixels and the stored image signals are respectively compared by polarity comparison circuits 14a to 14y using the outputs of the slicer circuits 12a, 12b, 13a, and 13b. More specifically, in the dark region of the pattern edge detected through the second differentiation, the polarities and the magnitudes of the absolute values of the linear derivatives of the detected image signal and the stored image signal are compared with each other for each of the eight directions. Then, when there is a pixel whose polarities are not in agreement in the region whereby either of the absolute values thereof is large, a value "1" indicative or the disagreement is output. The slicer circuits 12a and 13a each have, for example, 25 outputs for 5×5 pixels, and, hence, 25 polarity comparison circuits are provided in this case.

Figure 5:
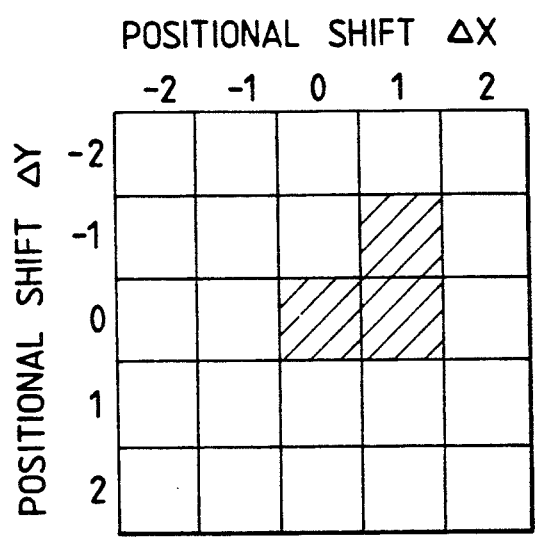
FIG. 5 is a diagram showing positional shift amounts ($\Delta X$, ($\Delta Y$)

Then, the number of disagreeing pixels obtained from the polarity comparison circuits 14a to 14y is counted by counter circuits 15a to 15y, for each area, for example, of 1024 pixels×256 pixels. A positional shift detector circuit 16 analyzes the number of disagreeing pixels obtained from the counter circuits 15a to 15y and outputs amounts of positional shifts (ΔX1, ΔY1), ..., (ΔXm, ΔYm) at which the number of disagreeing pixels is smaller than a preset value. The amounts of positional shifts, for example, are as shown in FIG. 5.

The outputs of the polarity comparison circuits 14a to 14y are delayed by delay circuits 17a to 17y until the above positional shift amounts are obtained. Then, only the outputs of the polarity comparing circuits 14 corresponding to the shift amounts (ΔX1, ΔY1), ..., (ΔXm, ΔYm) are left active and others are masked by region selection circuits 18a to 18y. Then, the logical product of the outputs of the region selection circuits 18a to 18y is obtained through an AND circuit 19, and thus, a value "1" indicative of a defect is output therefrom. The circuit 19 need not necessarily be an AND circuit, and also the region selection circuits need not necessarily be AND circuits.

A principle of operation of the present invention as illustrated in to FIG. 1 will now be described with reference to the following arrangements (1)–(9) to detect a defect.

Figure 6:
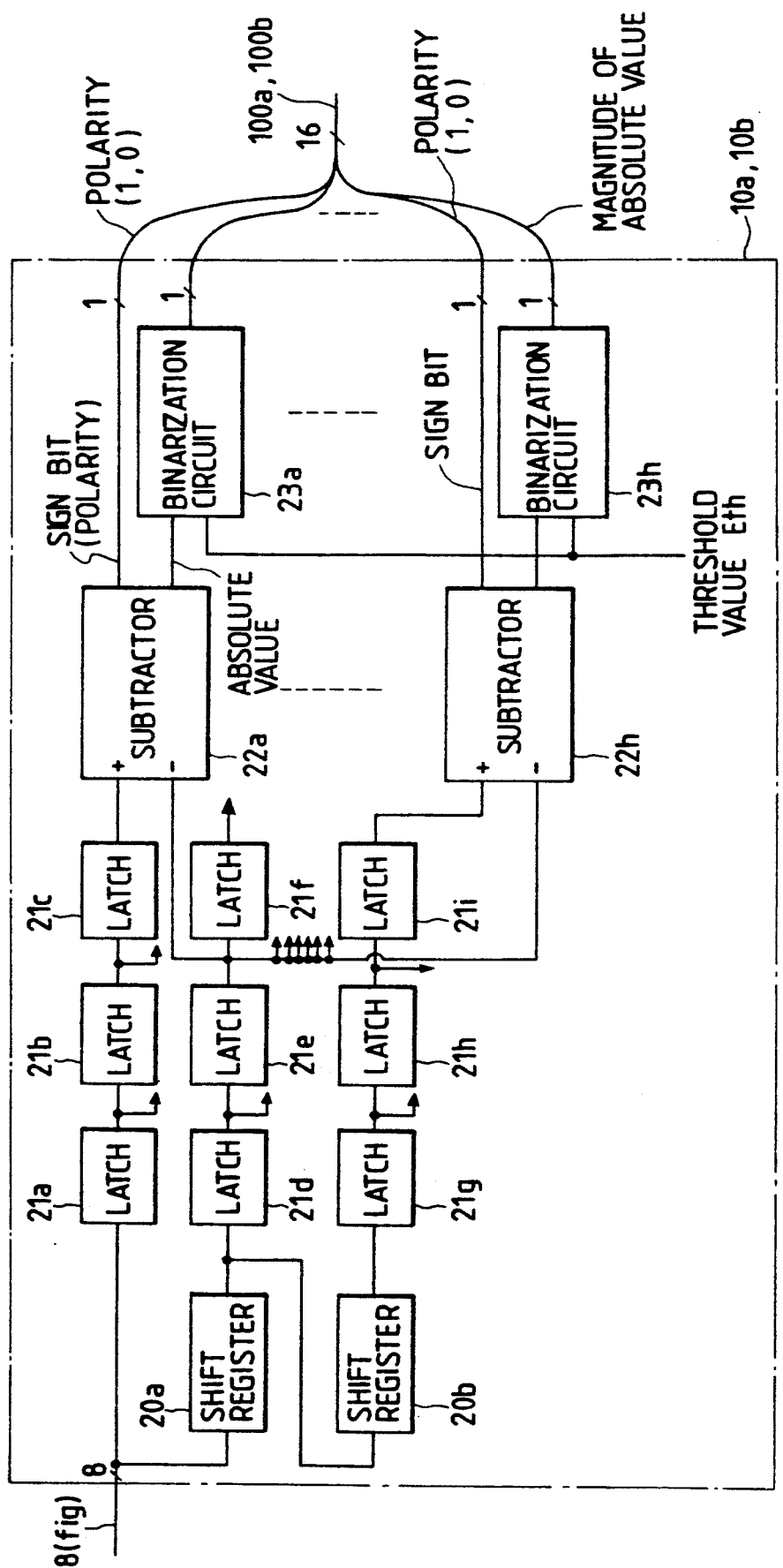
FIG. 6 is a block diagram showing an example of a construction of a linear differentiation circuit.
Figure 8:
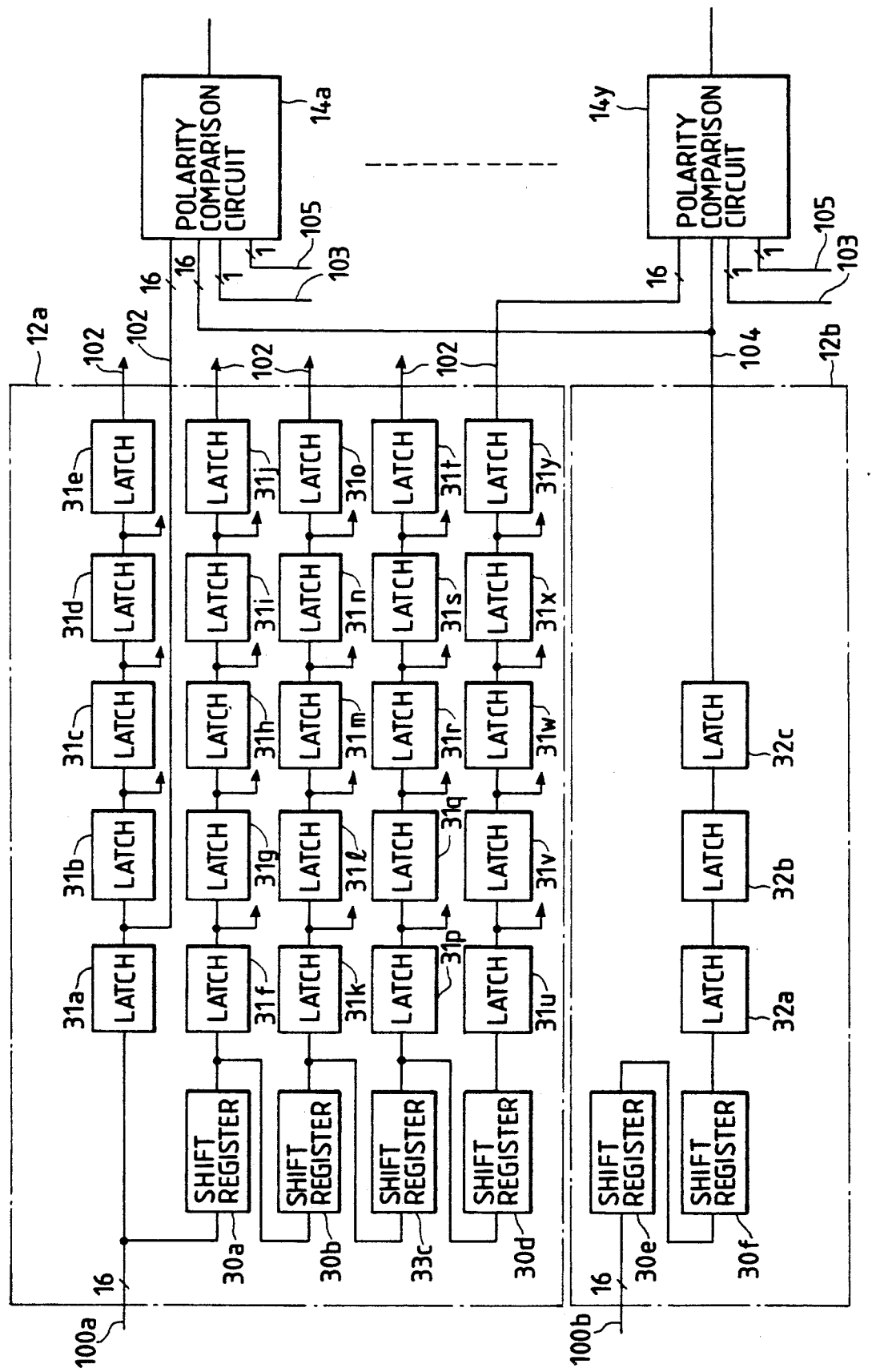
FIG. 8 is a block diagram showing an example of a construction of slicer circuits for slicing linear derivative signals output from the linear differentiation circuits.
Figure 10:
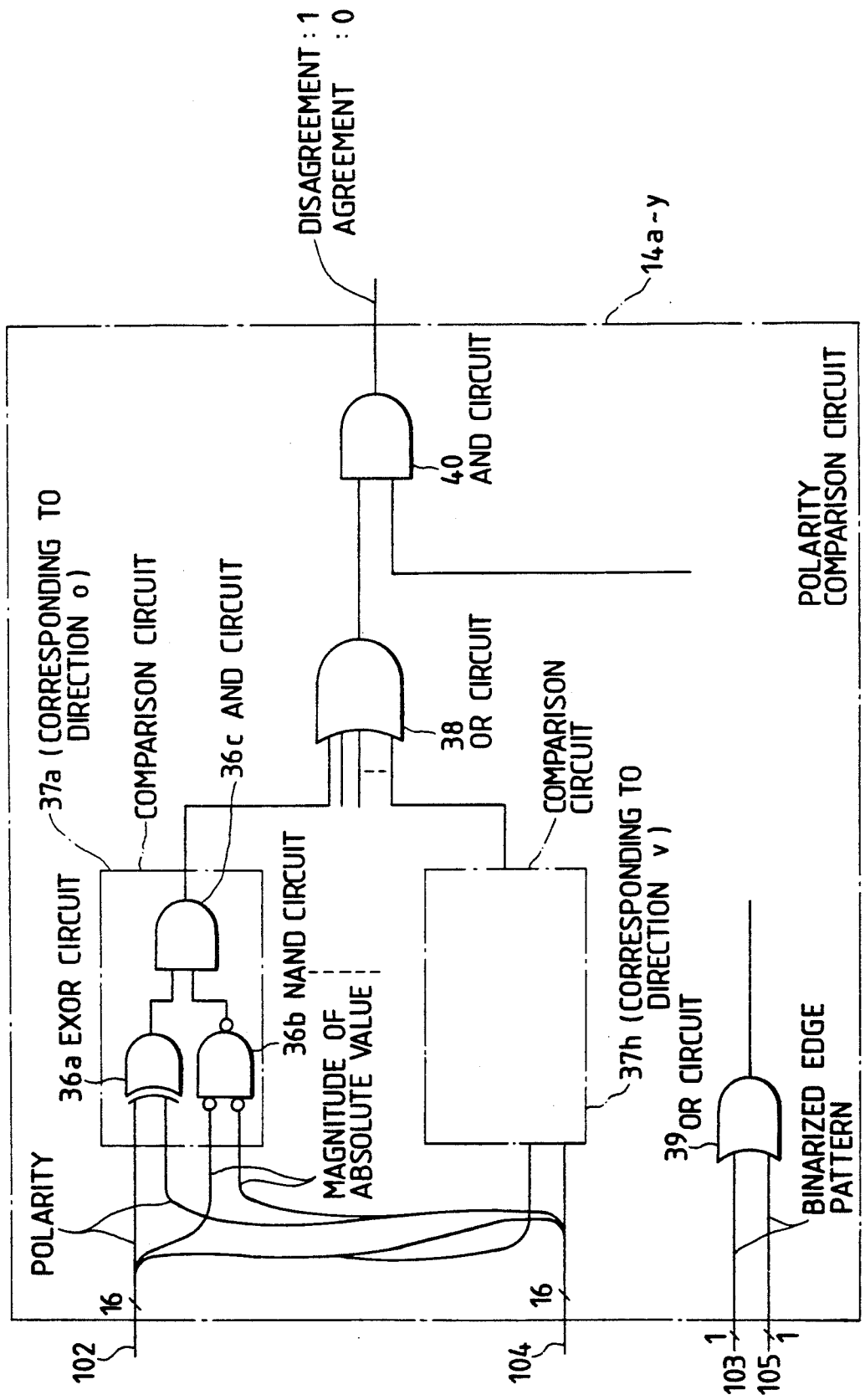
FIG. 10 is a diagram showing an example of a construction of a polarity comparison circuit.

(1) The gray image signals f and g are respectively subjected to linear differentiation in linear differentiation circuits 10a and 10b having a construction as shown in FIG. 6. Then, the polarities, whether positive or negative, of the linear derivatives obtained from subtractors 22a to 22h are compared for each of the images by means of slicer circuits 12a and 12b having a construction as shown in FIG. 8 and polarity comparison circuits 14a to 14y having constructions as shown in FIG. 10 and disagreements are detected as defects.

(2) In the linear differentiation performed in the linear differentiation circuits 10a and 10b (shown in FIG. 6), the polarity comparison of the linear derivatives obtained from the subtractors 22a to 22h is performed to detect a disagreement as a defect only for the pixel whose absolute values of the linear derivatives obtained from binarization circuits 23a to 23h, for both or either of the image signals, are larger than a preset value Eth.

Figure 7:
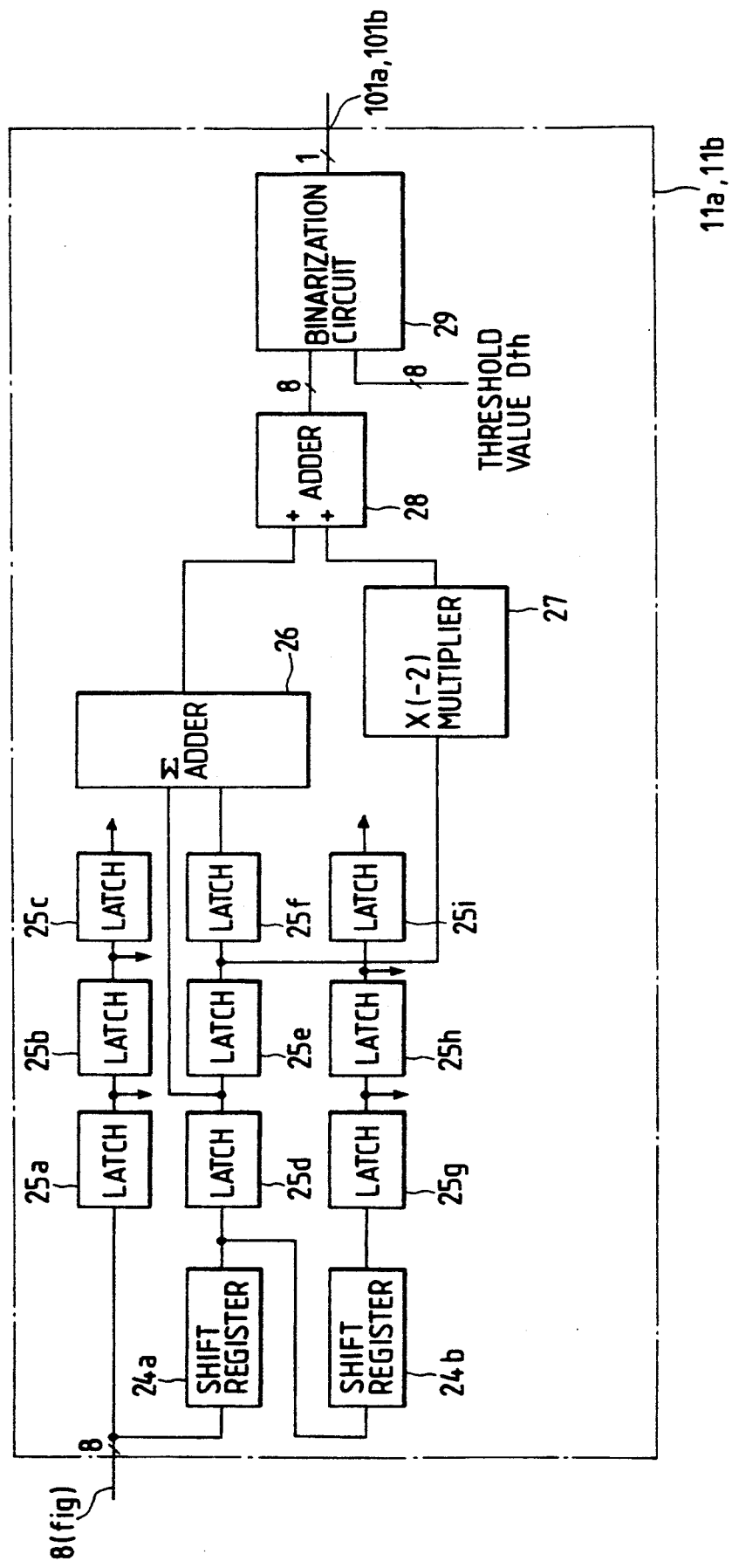
FIG. 7 is a block diagram showing an example of a construction of a second differentiation circuit.

(3) Gray image signals f and g are subjected to second differentiation in second differentiation circuits 11a and 11b having constructions as shown in FIG. 7 and binarized with a threshold value Dth and, then, the polarity comparison circuits 14a to 14y operate only in one region depending on the output signals of slicer circuits 12a, 12b (FIG. 8), and 13a and 13b (FIG. 9), and the polarity disagreement obtained thereby is detected as a defect.

Figure 12:
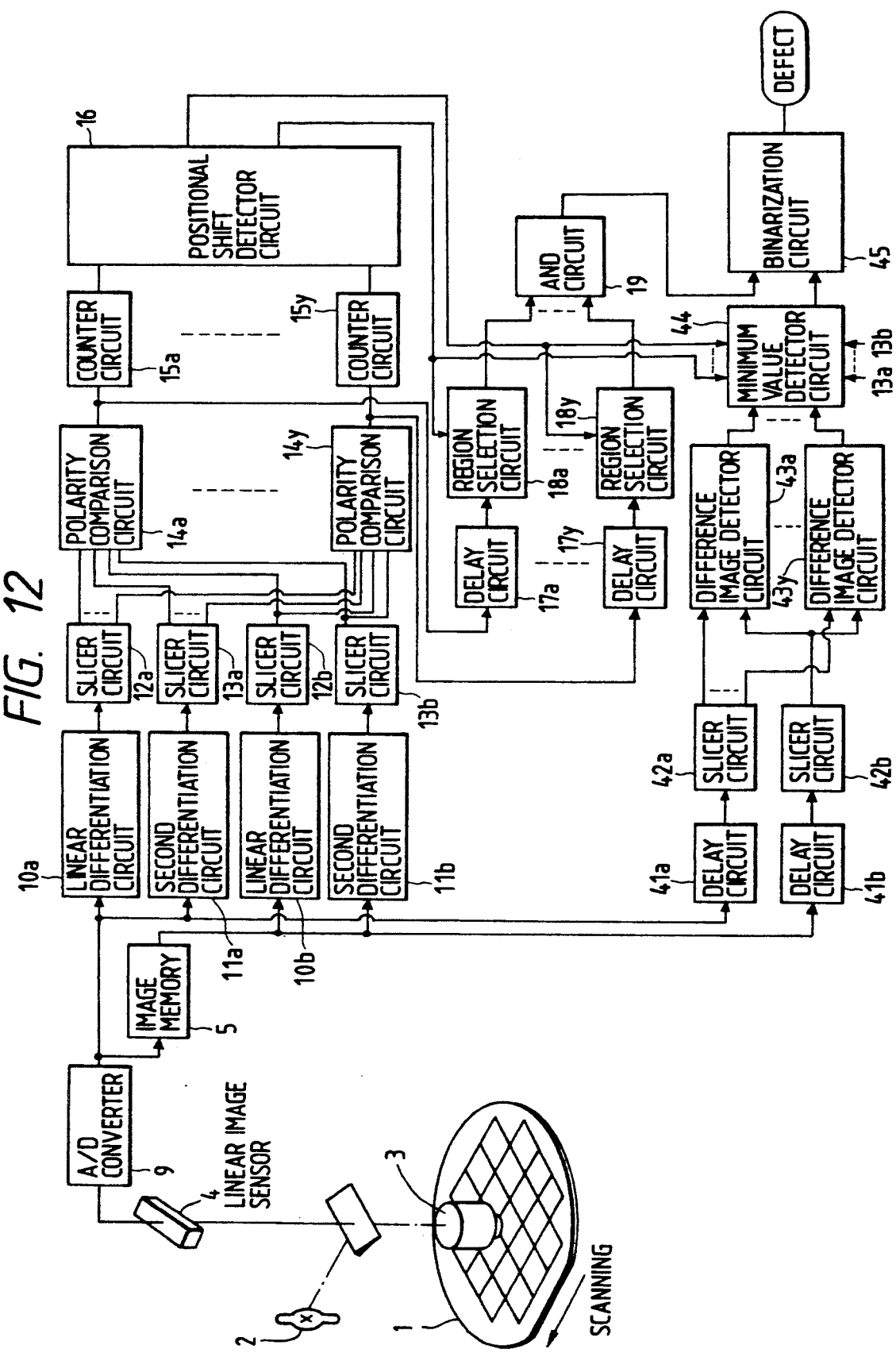
FIG. 12 is a block diagram showing another embodiment for detecting defects in circuit patterns according to the present invention different from that in FIG. 1.

(4) As shown in FIG. 12, gray image signals f and g are subjected to second differentiation in the second differentiation circuits 11a and 11b and binarized with a threshold value Dth, polarity comparison is performed in one region (edge region) and a polarity disagreement is detected as the output of an AND circuit 19, and the values of the gray signals f and g are compared in another region (non-edge region), or in all regions, and the difference image signals are binarized and a disagreement is detected as a defect by a minimum value detector circuit 44.

(5) A lower threshold value is set up in the disagreeing region obtained by either of the above-described arrangements (2) and (3), while a higher threshold value is set up in another region, and the difference image signals of the gray image signals f and g are binarized therewith to have a defect detected.

(6) Two gray images f and g are aligned with each other so that the number of disagreeing pixels obtained by either of the arrangements (2) and (3) may become a minimum.

(7) The gray image signals are aligned at a plurality of positions where the number of disagreeing pixels obtained by either of the arrangements (2) and (3) are less than a predetermined value.

(8) Images are aligned with each other in the plurality of positions obtained in the arrangements (7) and the common disagreement obtained by any of the arrangements (2) to (5) is detected as a defect.

(9) The gray images are subjected to filtering so that the number of disagreeing pixels obtained by either of the arrangements (2) and (3) may become symmetrical about the minimum number of pixels with disagreeing polarity, i.e., a center with respect to positional shifts, or the numbers of plural disagreeing pixels may become virtually equal on both side thereof.

Figure 16A:
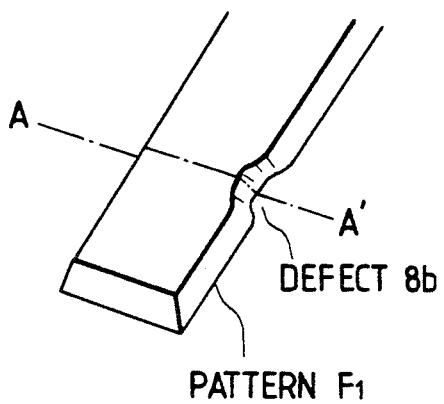
FIGS 16(a) to (d) and FIGS. 17(a) to (d) are diagrams showing examples of gray waveforms.
Figure 16B:
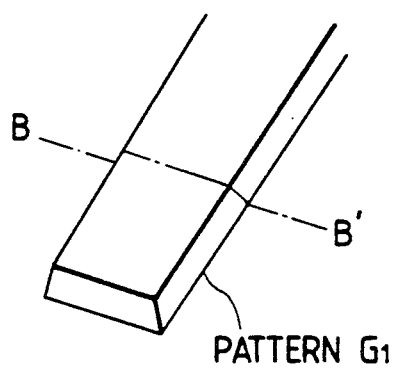
Figure 16C:
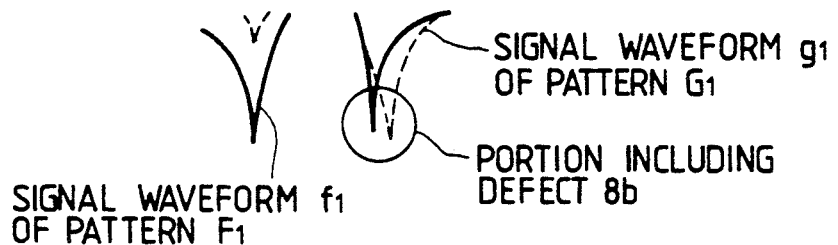
Figure 16D:
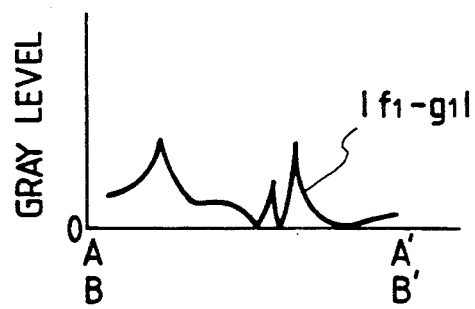
Figure 17A:
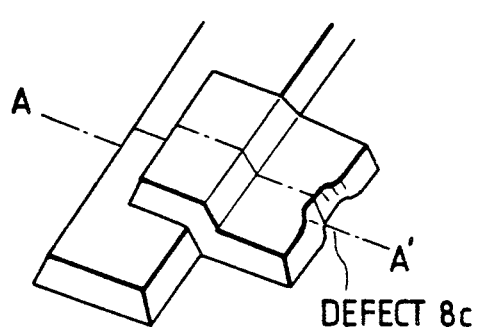
Figure 17B:
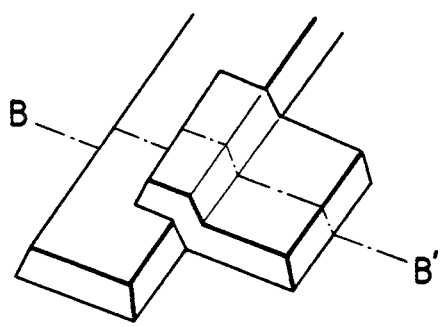
Figure 17C:
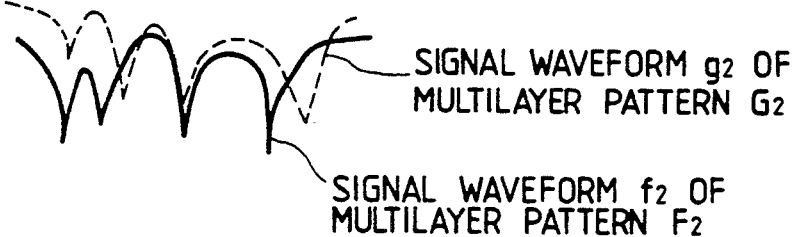
Figure 17D:
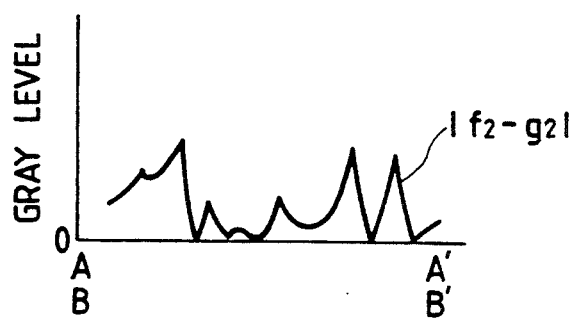
Figure 18A:
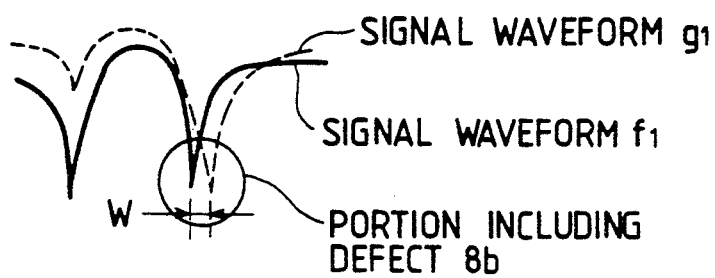
FIGS. 18(a) to (c) are diagrams for explaining the principle of polarity comparison according to the present invention.
Figure 18B:
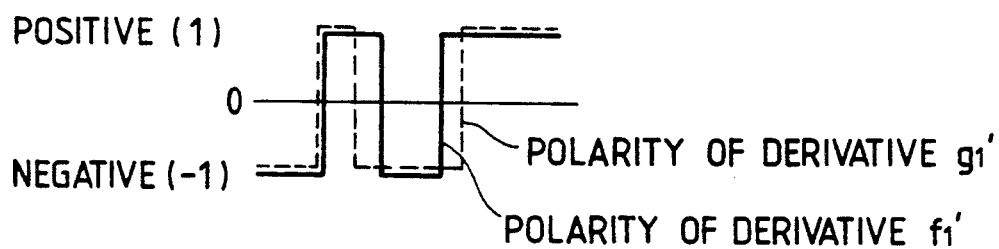
Figure 18C:
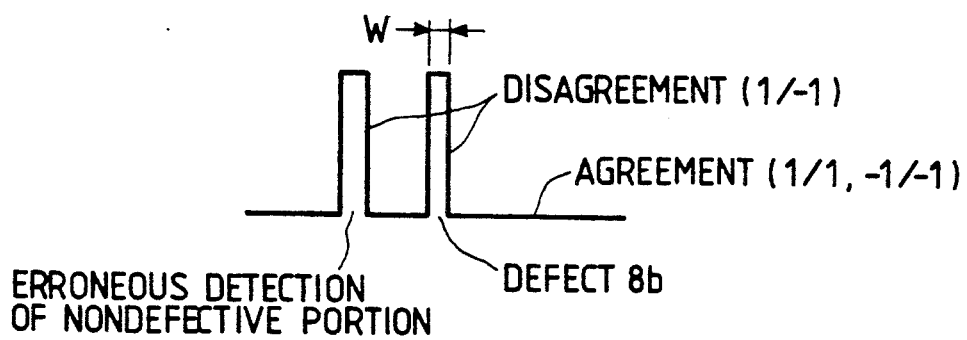
Figure 19A:
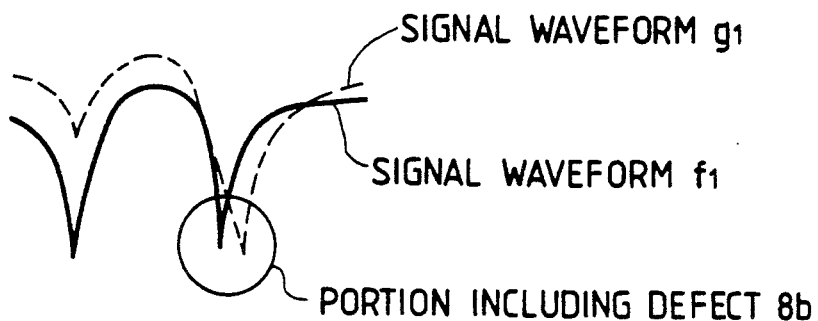
FIGS. 19(a) to (c) are diagrams for explaining the improvement made in the polarity comparison according to the present invention.
Figure 19B:
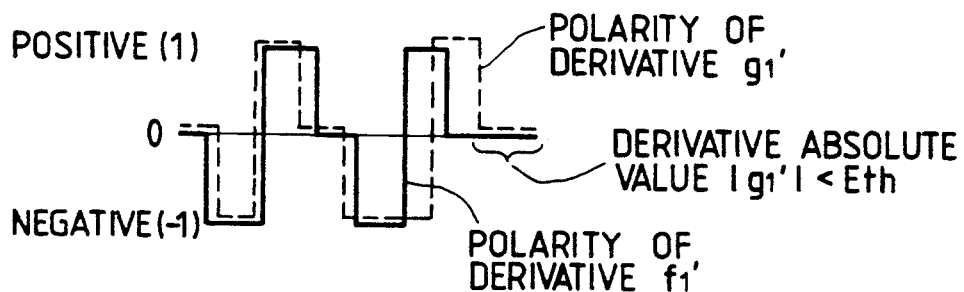
Figure 19C:
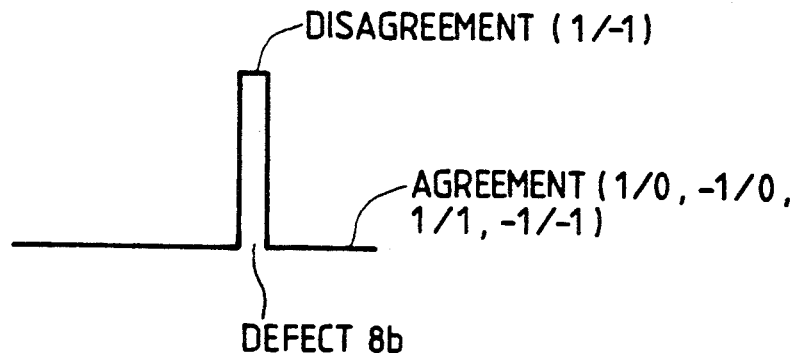
Figure 20A:
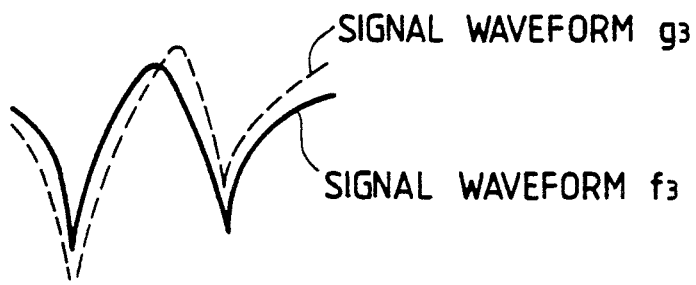
FIGS. 20(a) to (c) are diagrams for explaining occurrence or erroneous detection in the polarity detection according to the present invention.

The functions performed by the arrangements (1) to (9) using signal waveforms will now be described with respect to two circuit patterns F1 and G1 different in gray level as shown in FIGS. 16(a), (b), (c), and (d) wherein pattern F1 has a defect 8b. The signal waveforms f1 and g1 as shown in FIG. 18(a) are subjected to linear differentiation by the arrangement (1), i.e., by the linear differentiation circuits 10a and 10b, and waveforms f1' and g1' are obtained and, then, by plotting their polarities, waveforms as shown in FIG. 18(b) are obtained. Then, 1 bit (1 0), which becomes 1 or −1 depending on the polarity, whether positive or negative, of the linear derivative from the subtractors 22a to 22h of the linear differentiation circuits 10a and 10b, is assigned to the corresponding waveforms. Thereupon, the two polarity waveforms are compared with each other and a disagreement is detected when one is 1 and the other is −1. Then, a waveform as shown in FIG. 18(c) is obtained. The defect 8b can be detected as a disagreement and the detected size is accurately concurrent with the size of the actual defect. However, erroneous detection can occur in the normal portions due to difference in the condition or the down slope at the edge of the circuit pattern or the like. Hence, the arrangement (2) is used. More specifically, if absolute values $|f1'|$ and $|g1'|$ of the linear derivatives f1' and g1' from the binarization circuits 23a to 23h of the linear differentiation circuits 10a and 10b, with respect to a threshold value Eth, are in the condition as expressed as $$|f1'| < Eth \text{ or } |g1'| < Eth,$$

the polarity of the linear derivatives f1' and g1' is brought to 0 by force and, thereby, polarity waveforms as shown in FIG. 19(b) are obtained. By comparing these waveforms, a waveform as shown in FIG. 19(c) is obtained, whereby only the defect 8b can be accurately detected. The above described detection corresponds to defect detection performed in the region where $\min\{|f1'|,|g1'|\} \geq Eth$ holds, but a similar result can be obtained by performing detection in the region where $\max\{|f1'|,|g1'|\} \geq Eth$ holds. As described above, defect detection by the arrangement (2) is achieved, but in the case or some objects of inspection, signal waveforms f3 and g3 as shown in FIG. 20(a) are obtained even in the normal portion and, thereby, erroneous detection in the normal portion is produced because of a difference between the waveforms at the bright portion.

Figure 14:
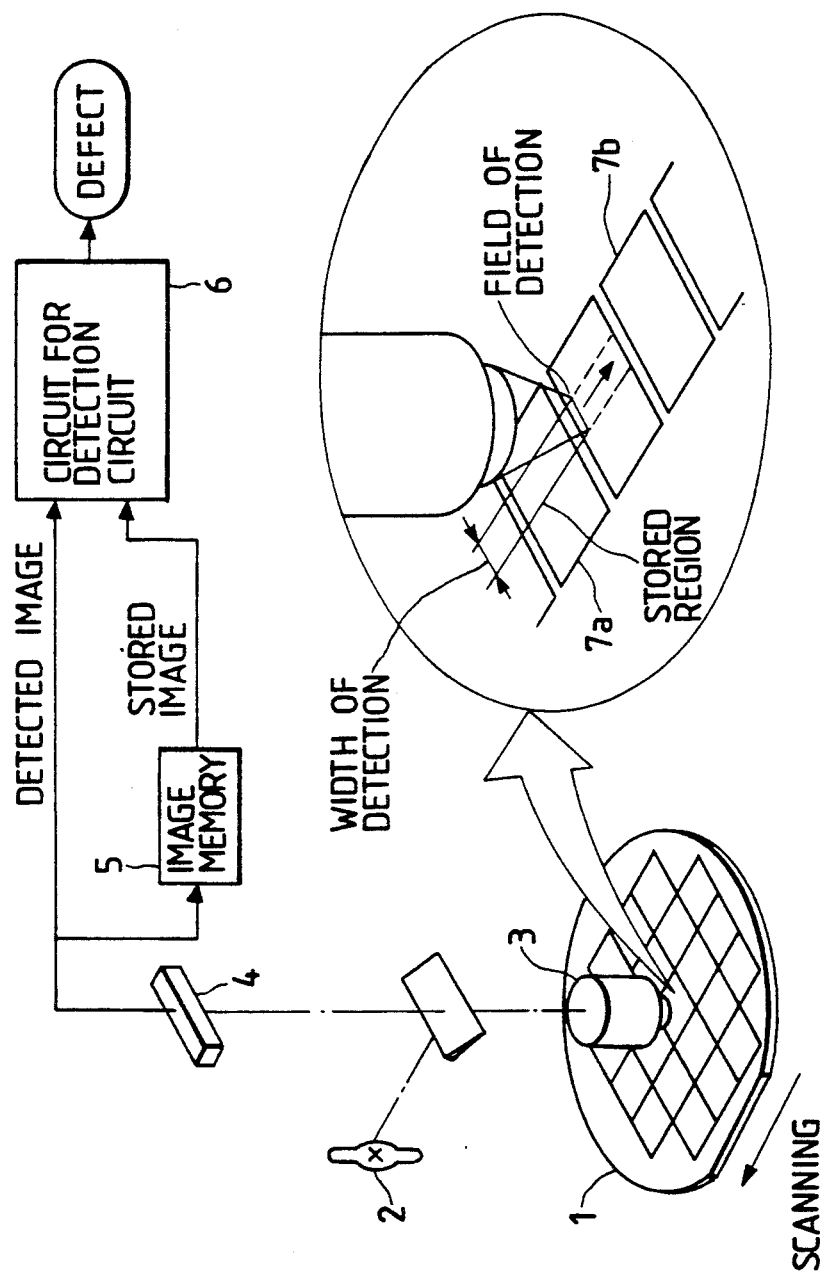
Figure 21A:
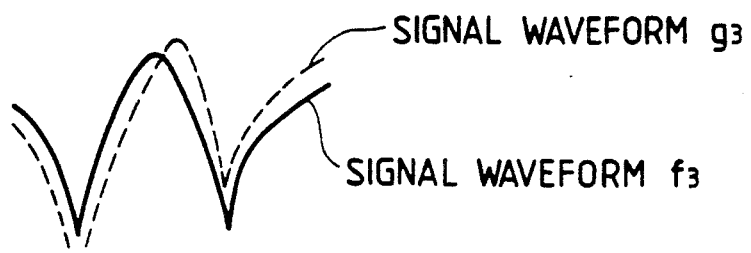
Figure 21B:
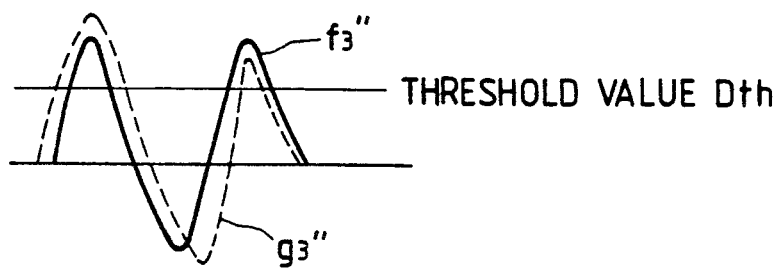
Figure 21C:
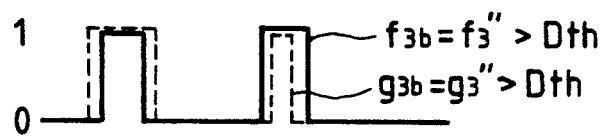
Figure 21D:

In the ordinary bright field illumination as shown in FIG. 14, the circuit pattern edge is seen to be dark and, therefore, by using the arrangement (2) for the dark edge, the erroneous detection as described above can be prevented. That is, the arrangement (3) is used as shown in FIGS. 21(a) to (d). More specifically, second derivatives of the signal waveforms f3 and g3, i.e, f3'' and g3'', are binarized by the second differentiation circuits 11a and 11b (FIG. 7) with a threshold value Dth (an edge operator (1, −2, 1) is realized by an adder 26, a multiplier 27, and an adder 28, and then the obtained signals are binarized by a binarization circuit 29 with the preset threshold value Dth), whereby signals f3b and g3b are obtained where f3b=f3''>Dth and g3b=g3''>Dth, and the logical sum of these signals, i.e., f3b U g3b, is obtained. The region R in question corresponds to the edge of circuit pattern and, hence, by comparing the polarities of the linear derivatives in this region, the erroneous detection is prevented from occurring as shown in FIG. 21(e).

Figure 22A:
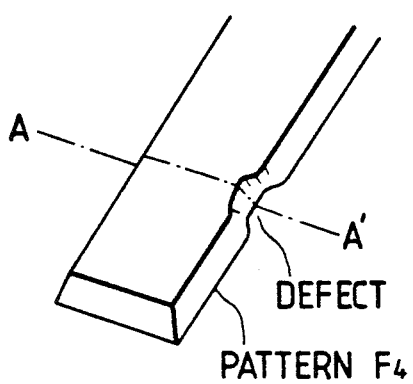
FIG. 22(a) to (e) are diagrams explaining discoloration defect detection.
Figure 22B:
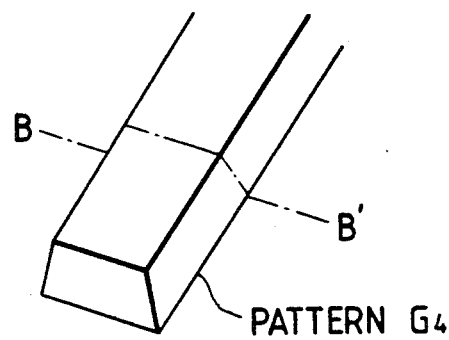

By using the arrangement (3), not only the existence or nonexistence of a shape defect at the edge of circuit pattern, but also the size of the defect are accurately detected. However, in the case as shown in FIGS. 22(a) and (b), where the difference in film thickness between the circuit pattern F4 and the circuit pattern G4 is so great as to exceed an acceptable limit, the arrangement (4) is used to make such a difference detectable as a defect. That is, a difference signal waveform $|f4−g4|$, as shown in FIG. 22(d) obtained from the waveforms in FIG. 22(c) (by means of the difference image signal detector circuits 43a to 43y shown in FIGS. 12 and 13) is binarized with a threshold value Vth. Then, the portion in question becomes detectable as shown in FIG. 22(e).

By using the arrangement (5), i.e., by having signals binarized with a lower threshold value in the region of disagreement obtained by the arrangement (3) and with a higher threshold value in another portion, it also becomes possible to detect even small defects strictly at the edge of circuit pattern, while defects at another portion are roughly detected to such a degree that erroneous detection is just prevented from being made.

Figure 23:
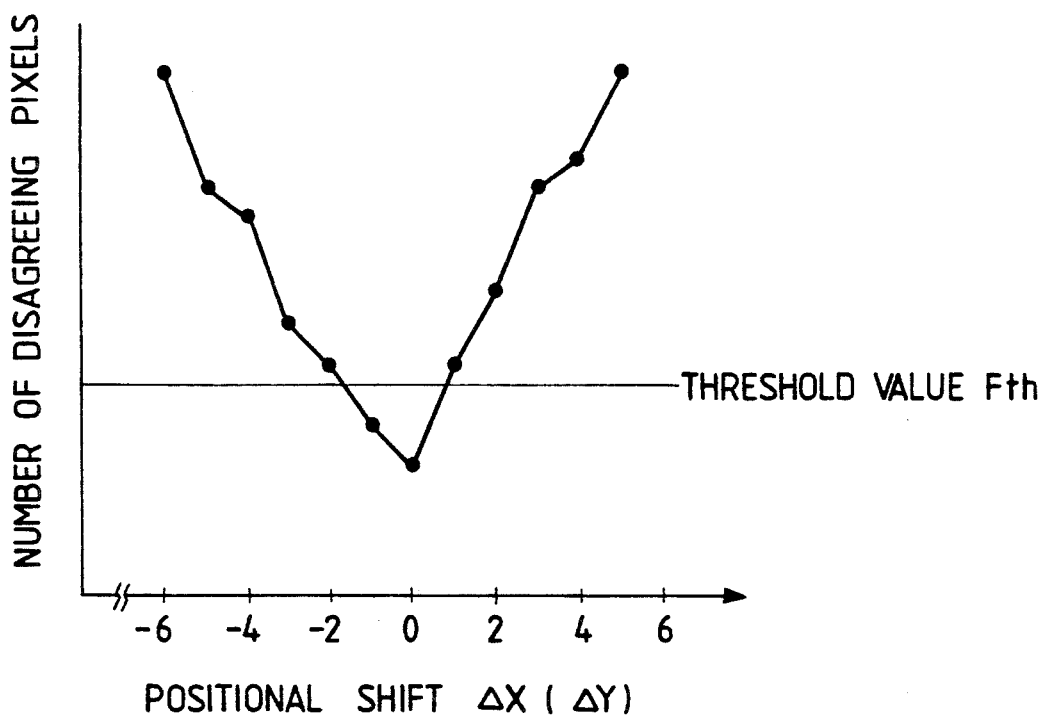
FIG. 23 is a graph showing the relationship between numbers of disagreeing pixels and shift amounts.

The number of disagreeing pixels obtained by the above described arrangements (2) or (3) plotted against the amounts of positional shift ΔX (ΔY) between two images takes the form as shown in FIG. 23. Therefore, by using the means (6), that is, by having the two images f and g aligned by slicer circuits 12a and 12b (FIG. 8) such that the number of disagreeing pixels becomes a minimum, the state where the edge positions of the circuit patterns in the images match well (two images are accurately registered) can be realized. By performing comparison using any of the arrangements (2) to (5) with two images accurately registered, detection of a defect can be achieved with high accuracy.

Figure 24A:
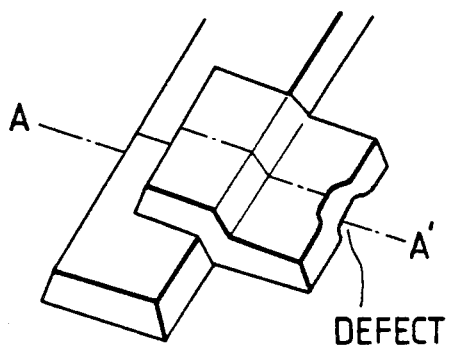
FIGS. 24(a) to (i) are diagrams for explaining polarity comparison at portions where interlayer slippages are present.
Figure 24B:
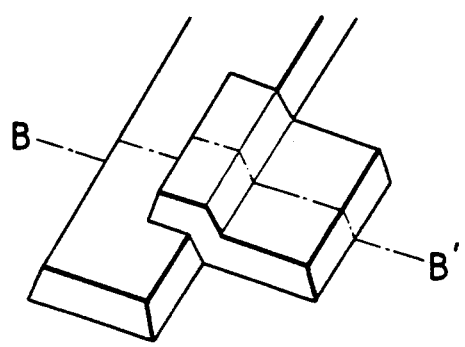
Figure 24C:
Figure 24D:
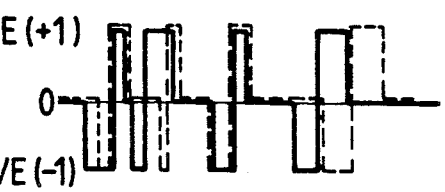
Figure 24E:
Figure 24F:
Figure 24G:
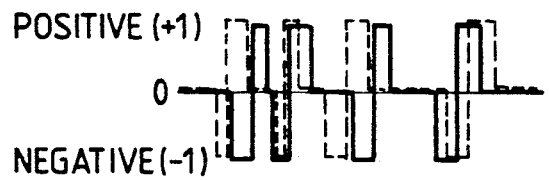
Figure 24H:
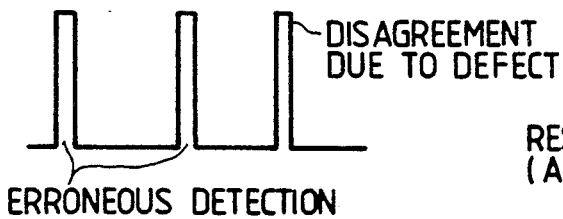
Figure 24I:

In the case where there is an interlayer slippage as shown in FIGS. 24(a) and (b) representing perspective views of multilayer patterns F2 and G2, the number of disagreeing pixels is not at its minimum only at one point, but the number is minimized at a plurality of points where the pattern edges of the multiple patterns are put in alignment. Therefore, the two images f2 and g2 are aligned with each other by means of the slicer circuits 12a and 12b for example at the position ΔX=0 in FIG. 23, where the number of the disagreeing pixels becomes a minimum. Then, the signal waveforms f2 and g2 at the portions AA' and BB' of FIGS. 24(a) and (b) become as shown in FIG. 24(c). Then, if the arrangement (3) is used, an erroneous detection is made at the position where the interlayer slippage is present as shown in FIG. 24(e). Then, the two images f2 and g2 are aligned at the position ΔX=−1, if the number of disagreeing pixels becomes the second lowest thereat. By using the arrangement (3) to shift the signal waveform f2 and the signal waveform g2 to the left by one pixel, waveforms shown in FIGS. 24(g) and (h) are obtained. Thereupon, if an AND operation is performed on the result of detection at the position ΔX=0 and the result of detection at the position ΔX=−1 by an AND circuit 19, the disagreement commonly output in both of the results can be detected as shown in FIG. 24(i), and thus, only the defect can be accurately detected without being affected by the interlayer slippage.

The number of disagreeing pixels varies with the objects to be inspected not only due to the existence of interlayer slippages, but also due to minute irregularities which the circuit patterns have. By determining the number of plural points where the images are to be aligned in accordance with the number of disagreeing pixels, the sensitivity of the defect detection can be automatically set up corresponding to the fabricated conditions of the circuit patterns.

Figure 25A:
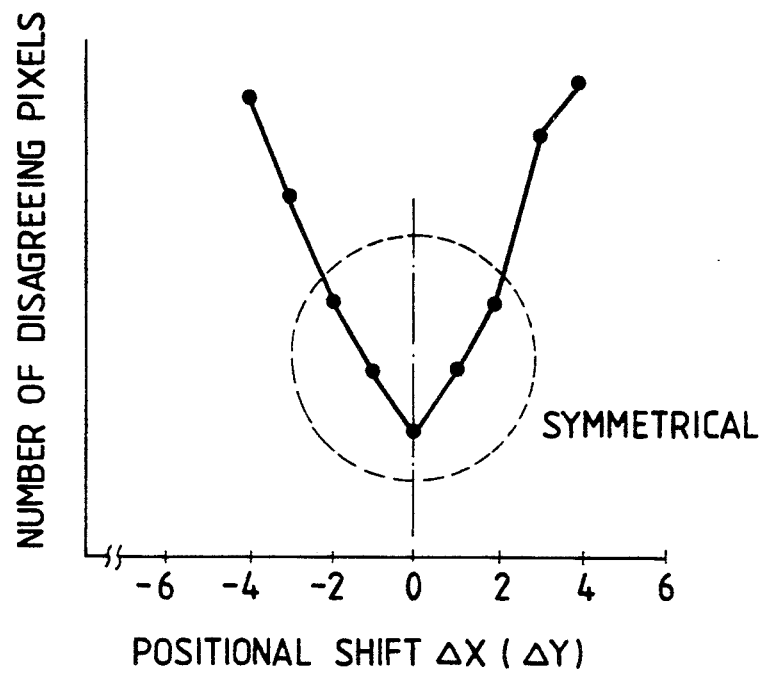
FIGS. 25(a) and (b) are each a graph showing the relationship between numbers of disagreeing pixels and shift amounts.
Figure 25B:
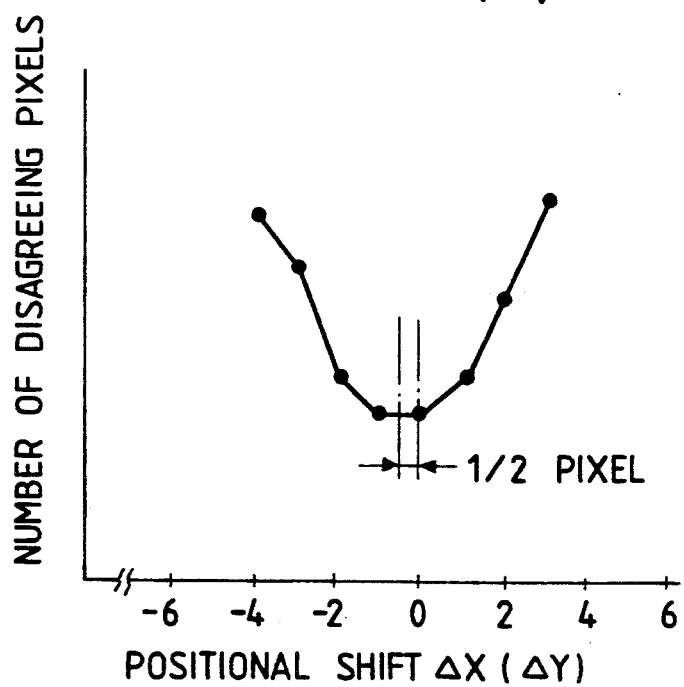

According to the arrangement (9), the conditions of positional shift of the images can be changed as desired by applying filtering to the obtained gray image. More specifically, if the number of disagreeing pixels becomes as shown in FIG. 25(a), it is indicated that the alignment of the two images can be achieved with accuracy below a fraction of one pixel, and if the same becomes as shown in FIG. 25(b), it is indicated that one image is just shifted from another by ½ pixel. Accordingly, in the case of FIG. 25(a), by performing the alignment at the position where the number of disagreeing pixels is at its a minimum, i.e., ΔX=0 in the present case, defect detection with extremely high accuracy can be achieved and very minute defects can be detected. In the case of FIG. 25(b), by performing alignment at two points where the numbers of disagreeing pixels are minimized, i.e., points ΔX=0 and ΔX=−1, defect detection allowing a shape difference corresponding to ½ pixel can be realized. Here, the above described filtering of the image is realized by having a filter with these coefficients $$\begin{vmatrix} a11 & a12 & a13 \\ a21 & a22 & a23 \\ a31 & a32 & a33 \end{vmatrix}$$

convoluted in the image, where the coefficients aij (i, j=1 to 3) can be determined according to the number of disagreeing pixels.

Referring now to the detailed block diagram of the circuits, FIG. 6 is a block diagram showing an example of the construction of the linear differentiation circuit 10a, 10b. From an eight-bit digital signal 8, an area of 3×3 pixels is sliced by shift registers 20a and 20b and latches 21a to 21i and these are stored in the latches 21a to 21i. From these 3×3 pixels, the linear derivatives in eight directions as shown in FIG. 3 indicated as o-v for signal f and o'-v' for signal g are calculated by means of subtractors 22a to 22h.

The linear derivatives for signal f are expressed as:

$o = f(x+1, y-1) - f(x,y)$ $p = f(x, y-1) - f(x,y)$ $q = f(x-1, y-1) - f(x,y)$ $r = f(x-1, y) - f(x,y)$ $s = f(x-1, y+1) - f(x,y)$ $t = f(x, y+1) - f(x,y)$ $u = f(x+1, y+1) - f(x,y)$ $v = f(x+1, y) - f(x,y)$

The linear derivatives for signal g are expressed as:

$o' = g(x+1, y-1) - g(x,y)$ $p' = g(x, y-1) - G(x,y)$ $q' = G(x-1, y-1) - G(x,y)$ $r' = G(x-1, y) - g(x,y)$ $s' = G(x-1, y+1) - G(x,y)$ $t' = G(x, y+1) - G(x,y)$ $u' = G(x+1, y+1) - G(x,y)$ $v' = G(x+1, y) - G(x,y)$

In this case, the subtractor 22a corresponds to the linear differentiation o and the subtractor 22h corresponds to the linear differentiation v (thus, the subtractors 22a to 22h perform linear differentiation o to v) and the output of the subtractors 22a to 22h is formed of one bit each of the sign bit for a positive or negative polarity (1, 0) and eight bits representative of the absolute value ($|f'|$ or $|g'|$) of the linear derivatives. Each of binarization circuits 23a to 23h is a circuit for obtaining a binarized signal by binarizing the absolute value of the linear derivative with a preset threshold value Eth as shown in FIG. 19(b), i.e., the circuit outputs "1" when the absolute value ($|f'|$ or $|g'|$) of the linear derivative is larger than the threshold value Eth and outputs "0" when it is smaller than the threshold value Eth. That is, the binarization circuit outputs a value of one bit (1, 0) obtained by binarizing the absolute value of the linear derivative. It is apparent that the threshold value Eth may be changed for $|f'|$ and $|g'|$. Thus, from the subtractors 22a to 22h and the binarization circuits 23a to 23h, a signal of a 16-bit structure obtained by combining signals indicative of polarities with respect to the adjoining eight pixels (in eight directions) an eight signals indicative of magnitudes of the absolute values with respect to the adjoining eight pixels (in eight directions) is output as a signal 100a or 100b.

FIG. 7 is a block diagram showing an example of the construction of the second differentiation circuit 11a, 11b. From an eight-bit digital signal 8, an area of 3×3 pixels is sliced by shift registers 24a and 24b and latches 25a to 25i and these pixels are stored in the latches 25a to 25i. From these 3×3 pixels, a binary edge pattern is extracted using the edge operator as shown in FIG. 4. More specifically, the edge operator (1, −2, 1) is realized by means of an adder 26, a multiplier 27, and an adder 28 and the thus obtained signals are turned into a binary signal by means of a binarization circuit 29 with a preset threshold value Dth in accordance with the following relations:

if(f(x−1, y)+f(x+1, y)−2f(x, y)>Dth or f(x, y−1)+f(x, y+1)−2f(x, y)>Dth or f(x−1, y−1)+(x+1, y+1)−2f(x, y)>Dth or f(x+1, y−1)+f(x−1, y+1)−2f(x, y)>Dth) then 1, otherwise 0.

Thereby, a signal of one-bit structure is output as a signal 101a, 101b, with "1" assigned to the dark region of the pattern edge and "0" assigned to another region. The other three edge operators shown in FIG. 4 can be similarly realized by an adder 26, a multiplier 27, and an adder 28. (The adders 26, the multipliers 27, and the adders 28 for realizing the other three edge operators are not shown in FIG. 7.)

FIG. 8 is a block diagram showing an example of the construction of the slicer circuits 12a and 12b. From the 16-bit digital signal 100a (a combination of eight signals indicative of polarities (1, 0) and eight signals indicative of magnitudes of the absolute values of the linear derivatives) output from the linear differentiation circuit 10a, an area of 5×5 pixels is sliced by means of shift registers 30a to 30d and latches 31a to 31y and these pixels are stored in the latches 31a to 31y. Also from the 16-bit digital signal (a combination of eight signals indicative of polarities (1, 0) and eight signals indicative of magnitudes of the absolute values of the linear derivatives) 100b output from the linear differentiation circuit 10b, the pixel corresponding to the pixel in the center of the above 5×5 pixels is input, by means of shift registers 30e and 30f and latches 32a, 32b, and 32c, to the latch 32c.

Figure 9:
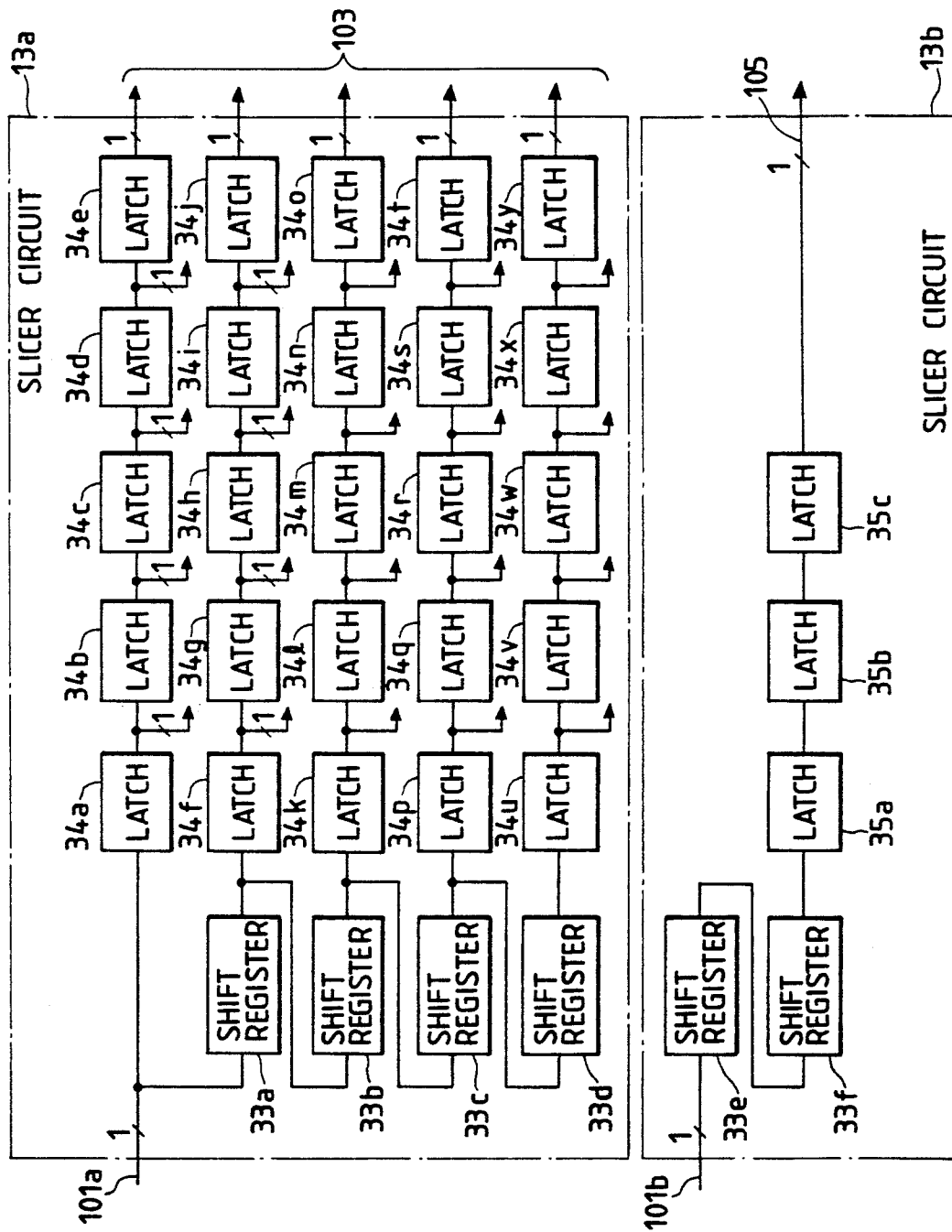
FIG. 9 is a block diagram showing an example of a construction or slicer circuits for slicing second derivative signals output from the second differentiation circuits.

The slicer circuits 13a and 13b shown in FIG. 1 can be realized in a similar structure to that described above. FIG. 9 shows an example thereof. From the one-bit binary signal 101a (the signal (1, 0) indicative of an edge region and another region) output from the second differentiation circuits 11a, an area of 5×5 pixels is sliced by shift registers 33a to 33d and latches 34a to 34y and these pixels are stored in the latches 34a to 34y. Also from the one-bit binary signal 101b (the signal (1, 0) indicative of an edge region and another region) output from the linear differentiation circuit 11b, the pixel corresponding to the pixel in the center of the above 5×5 pixels is input, by shift registers 33e and 33f and latches 35a, 35b, and 35c, to the latch 35c.

FIG. 10 is a diagram showing an example of the construction of the polarity comparison circuit 14a to 14y. A comparison circuit 37a, which makes effective a disagreement as a result of the polarity comparison only in the region where the absolute value of the linear derivative signal is large, is constituted by an EXOR circuit 36a detecting disagreement in polarity (positive:1, negative:0) of the polarities (positive:1, negative:0) included in the 16bit signals 102 and 104 to output a signal "1" when they are in disagreement and output a signal "0" when they are in agreement, a NAND circuit 36b outputting a signal "0" when the signals indicative of the magnitudes of the absolute values of the linear derivatives included in the 16-bit signals 102 and 104 are both small, i.e., "0", and outputting a signal "1" in other cases, and an AND circuit 36c prohibiting the signal "1" indicative of the disagreement in polarity from the EXOR circuit 36 from being output therethrough when the output of the NAND circuit 36b is "0". An OR circuit 38 is for obtaining the logical sum of the eight outputs (for eight directions) from comparison circuits 37a to 37h to thereby output, when a disagreement is detected as a result of the polarity comparison in the region where the absolute value of the linear derivative is large by at least one of the eight comparison circuits 37a to 37h, the signal indicative of the polarity disagreement. An OR circuit 39 is for obtaining the logical sum of the binarized edge pattern signals 103 and 105 output from the slicer circuits 13a and 13b to thereby output a signal "1" indicative or the fact that the edge pattern signal "1" has been detected in either of the detected image signal f or the stored image signal g, i.e., in either of the slicer circuit 13a or the slicer circuit 13b. An AND circuit 40 is for obtaining the logical product of the output of the OR circuit 38 and the output of the OR circuit 39 to thereby output a signal "1" indicative of the polarity disagreement obtained in the region where the absolute value of the linear derivative is large at the edge pattern.

By use of the above described arrangement, polarity waveforms of the linear derivatives for the detected image signal f1 and the stored image signal g1, which are as shown in FIG. 19(a), are obtained by changing the level to "0" in the region (the linear derivative $|f1'|$ or $|g1'|$ <Eth, of which the threshold value Eth can apparently be changed for $|f1'|$ and $|g1'|$) and converting the level into conformity with the polarity signal (positive: 1, negative: −1) of the linear derivative (f1' or g1') in another region (the region where the absolute value of the linear derivative is large), and the polarity waveform thus obtained is shown in FIG. 19(b). Then, the polarity signal (positive: 1, negative: −1) of the linear derivative (f1' is compared with the polarity signal (positive: 1, negative: −1) of the linear derivative g1' in the region where the absolute value of the linear derivative signal is large (where the linear derivative $|f1'|$ or $|g1'|$ >Eth), and a signal indicative of a disagreement (1/−1) is output from the OR circuit 38 of the polarity comparing circuits 14a to 14y shown in FIG. 10 as the result of the determination as shown in FIG. 19(c). Namely, in the region where the absolute value of the linear derivative signal is large, the defect 8b is detected as a disagreement of the polarity with respect to the detected image signal f1 and the stored image signal g1 by means of the OR circuit 38 of the polarity comparing circuits 14a to 14y shown in FIG. 10. However, if, as shown in FIG. 18, it is attempted to detect the defect 8b only depending on the polarity disagreement with respect to the detected image signal f1 and the stored image signal g1, a polarity disagreement is detected at the normal portion as shown in FIG. 18 due to an extreme difference between the output image signals because of a special relationship between the detected image signal f1 and the stored image signal g1 and such a disagreement is erroneously detected as a defect. Then, by effecting an arrangement such that the polarity disagreement between the detected image signal f1 and the stored image signal g1 is detected in the region where the absolute value of the linear derivative signal is large, the erroneous detection at the normal portion can be prevented as shown in FIG. 19.

Figure 20B:
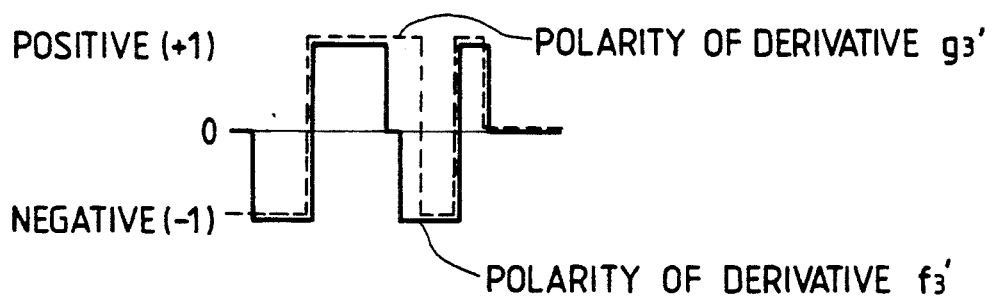
Figure 20C:
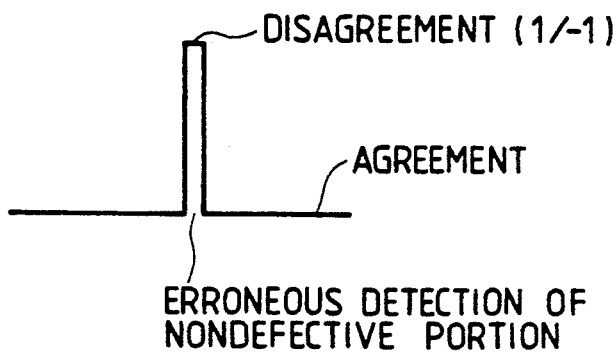

Further, as shown in FIG. 20, as the circuit pattern becomes more minute, a polarity disagreement comes to be detected in the middle of the circuit pattern due to a special relationship between the detected image signal f3 and the stored image signal g3 and, as a result, a normal portion comes to be erroneously detected as a defect. Then, the detected image signal f3 and stored image signal g3 as shown in FIG. 21(a) are converted to second derivative signals f3" and g3" (shown in FIG. 21(b) as "Second Derivative") by means of second differentiation circuits 11a and 11b, respectively. Then, by binarizing the second derivative signals f3" and g3" with a threshold value Dth (f3b=f3">Dth, g3b=g3">Dth), the edge signals 101a and 101b (shown in FIG. 21(c) as "Binarization of Second Derivative") are obtained. Thereupon, it is detected whether or not there is an edge signal in any direction through the OR detection (f3b U g3b) (shown in FIG. 21(d) as "OR Detection") in the OR circuit 39 of the polarity comparing circuit 14a to 14y shown in FIG. 10, and an edge signal "1" of the circuit pattern is obtained. Then, the defect signal due to a polarity disagreement detected by the OR circuit 38 of the polarity comparing circuit 14a to 14y shown in FIG. 10 is filtered by means of the AND circuit 40 obtaining the logical product of the same and the signal "1" obtained through the OR detection in the OR circuit 39 of the polarity comparing circuit 14a to 14y. Thus, as shown in FIG. 21(e), the erroneous detection at the normal portion due to the minute polarity disagreement occurring in the middle (non-edge region) of a circuit pattern can be prevented.

Figure 11:
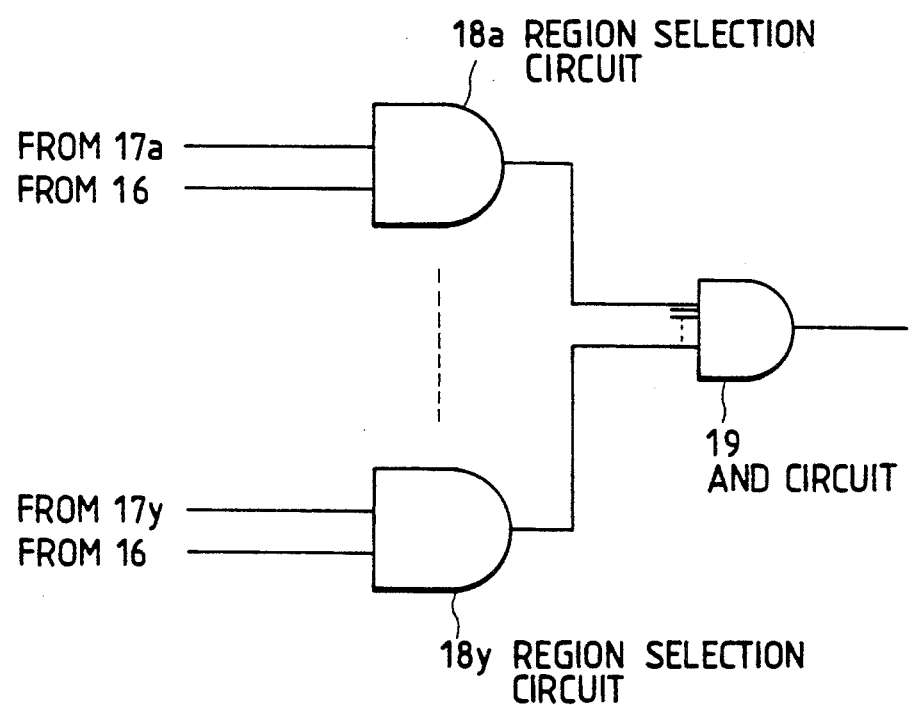
FIG. 11 is a diagram showing a region selection circuit and an AND circuit.

FIG. 11 is a diagram showing an example of the construction of region selection circuits 18a to 18y and an AND circuit 19. Results of the polarity comparison output from delay circuits 17a to 17y are binarized signals indicative of disagreement obtained as a result of comparison of polarities of the detected image signal f and the stored image signal g at the positions shifted by ±2 pixels by means of the slicer circuits 12a, 12b, 13a, and 13b. On the other hand, signals to be input to the region selecting circuits (AND circuits) 18a to 18y are selected as signals "1" depending on the shift amounts (ΔX1, ΔY1), ..., (ΔXm, ΔYm) obtained in the positional shift detector circuit 16. In the region selection circuits (AND circuits) 18a to 18y, the logical products of the disagreement binary signals output from the polarity comparison circuits 14a to 14y and the binary signals selected by the positional shift detector circuit 16 are obtained, i.e., the positional shift amounts beyond the range corresponding to a certain threshold value Fth (Sth) are masked as shown in FIG. 23, and then, outputs of these AND circuits are input to the AND circuit 19 so that the logical product thereof is obtained within the region of ±2 pixels and, thus, the determination as shown in FIG. 24 can be achieved.

Especially, in the case of multilayer circuit patterns as shown in FIG. 24, the positional shift detector circuit 16, the region selection circuits (AND circuits) 18a–18y, and the OR circuit 19 become necessary in defect detection. A multilayer pattern to be detected F2 is shown in FIG. 24(a) and a reference multilayer pattern G2 is shown in FIG. 24(b), and signal waveforms of the detected image signal f2 of the multilayer pattern to be detected F2 and the stored image signal g2 of the reference multilayer pattern G2 are shown in FIG. 24(c). As seen from these signal waveforms, there are present portions at which both patterns have no positional discrepancy therebetween and some portions at which they have some positional discrepancies therebetween. In the case of a multilayer pattern, in general, there are produced no positional discrepancy between upper layers, but there are produced some discrepancy between lower layers. Accordingly, polarity waveform signals 100a and 100b of linear derivatives as shown in FIG. 24(d) are obtained from the linear differentiation circuits 10a and 10b. If the polarity waveform signals 100a and 100b are only compared by the polarity comparing circuits 14a to 14y, the result of detection I is obtained (in which both erroneous detection and detection of disagreement due to a defect are carried out in the edge regions as polarity disagreements as shown in FIG. 24(e)). Then, the stored image signal g2 of the reference multilayer pattern G2 is shifted by means of the slicer circuit 12b to the left with respect to the detected image signal f2 of the multilayer pattern to be detected, and the relationship between the signals is shown in FIG. 24(f). The polarity waveform signals 100a and 100b of the derivatives of these signals are shown in FIG. 24(g). The polarity waveform signals 100a and 100b are compared in the polarity comparison circuits 14a to 14y, whereby the result of detection II is obtained (two disagreements by erroneous detection and one disagreement due to a defect are detected as polarity disagreements in the edge regions as shown in FIG. 24(h)). By obtaining the logical product of the result of detection I and the result of detection II through the AND circuit 19, the result of final detection as shown in FIG. 24(i) (in which the polarity disagreement due to a real defect is detected) is obtained.

So far, an example making use of polarities of linear derivatives for performing alignment and defect detection has been described. By virtue of the described arrangement, only real or actual defects can be accurately detected even if circuit patterns on LSI wafers or the like as objects of inspection have three-dimensional discrepancies due to differences in film thickness and condition of down slope at the edge portion, interlayer slippage, and difference in shape due to sampling errors at the time of inspection. The discrepancy in position of the darkest point of a pattern edge can be detected as a defect with very high accuracy.

Although, in the above described arrangement, both the linear differentiation and the second differentiation have been performed with 3×3 pixels sliced off, such can be realized even if the area to be sliced off is expanded to 5×5 pixels or more. Although the second differentiation in the above description has been arranged to detect dark pattern edges because the detection has had images obtained under bright field illumination as the object of inspection, bright pattern images may be detected under dark field illumination, in which case the edge operator may be of a($-1'$, 2, $-1$) arrangement or the like.

In the positional shift detector circuit 16, positional shift amounts $\Delta X$ and $\Delta Y$ meeting the condition $$S(\Delta X, \Delta Y) = Sth \ (Fth)$$

with respect to the number of disagreeing pixels $S(\Delta X, \Delta Y)$, where $\Delta X, \Delta Y \leq -2, -1, 0, 1, 2$, have been obtained, but instead of setting a constant for the threshold value Sth (Fth), it may be automatically set according to an expression as $$Sth = C1\{\min_{\Delta X, \Delta Y} S(\Delta X, \Delta Y)\} + C2$$

where C1, C2 are constants. According to this arrangement, the number of points where images are aligned can be adjusted according to the conditions of fabrication of the circuit patter (wiring pattern) and the sensitivity of defect detection can thereby be automatically set up.

In order to allow the existence of interlayer slippages more positively, the plural points where images are aligned may be obtained in the manner as described below. The number of disagreeing pixels $S(\Delta Xmin, \Delta Ymin)$ (where $\Delta Xmin, \Delta Ymin:\Delta X, \Delta Y$ minimizing $S(\Delta X, \Delta Y)$) is the number of disagreeing pixels when the detected image signal f and the stored image signal g are aligned and includes both disagreements at a normal portion and a defect. The main cause of the disagreement at the normal portion is an interlayer slippage and another cause is the existence of minute irregularities in the circuit pattern.

In the case of a pattern having an interlayer slippage, a position ($\Delta Xr, \Delta Yr$) where alignment is possible as shown in FIG. 26 can be obtained by shifting one image (for example, the recorded image) on the x-y plane. Accordingly, the value of the $S(\Delta X, \Delta Y)$ becomes smaller in the region where there is an interlayer slippage. On the other hand, a defect does not always fit in with the other image at such position (Xr, $\Delta Yr$) and, hence, the value of $S(\Delta Xr, \Delta Yr)$ of the defect is unchangeable. However, when one image is shifted in the case of a pattern having no interlayer slippage, a normal portion where both images were in agreement at the position ($\Delta Xmin, \Delta Ymin$) comes to be detected as a disagreement, and consequently, the value of $S(\Delta Xr, \Delta Yr)$ does not become smaller. Therefore, it is impossible to detect the positions $\Delta Xr, \Delta Yr$ allowing the existence of the interlayer slippage directly from comparison of the magnitude of $S(\Delta X, \Delta Y)$.

Therefore, a quantity $\Delta S(\Delta X, \Delta Y, \Delta Xof, \Delta Yof)$ given by the following expression (1) is introduced:

$$\Delta S(\Delta X, \Delta Y, \Delta Xof, \Delta Yof) = S(\Delta Xmin + \Delta Xof - \Delta X, \Delta Ymin + \Delta Yof - \Delta Y) - 2S(\Delta Xmin + \Delta Xof, \Delta Ymin + \Delta Yof) - S(\Delta Xmin + \Delta Xof + \Delta X, \Delta Ymin + \Delta Yof + \Delta Y) \quad (1)$$

where $\Delta S$ represents the disagreements that cannot be eliminated even if one of the images at the position ($\Delta Xmin + \Delta Xof, \Delta Ymin + \Delta Yof$) is shifted by $\Delta X, \Delta Y$. This will be described with reference to FIG. 27. FIG. 27 is a diagram showing an example of experiment for compensating for interlayer alignment errors (with a three-layer pattern) by an image shift. More specifically, the diagram shows a simulation pattern of a three-layer structure having minute interlayer slippages between the detected image and the stored image. FIG. 27 shows disagreeing images obtained through polarity comparison performed on the x-y plane with the recorded image shifted by $\pm \Delta X, \Delta Y$ (one pixel each). In the diagram, ($\Delta Xmin, \Delta Ymin$)=(0, 0), while the interlayer slippage is allowed to be present at the positions ($\Delta Xr, \Delta Yr$)=(1, 1), (0, $-1$).

Now, setting ($\Delta Xof, \Delta Yof$)=(0, 0), the position ($\Delta Xs, \Delta Ys$), where $\Delta S(\Delta X, \Delta Y, 0, 0)$ becomes a minimum, represents the position (1, 1), where the layers B are aligned, and these expressions are obtained:

$\Delta S(\Delta Xs, \Delta Ys, 0, 0)/4$: a disagreement with respect to the layer C at (0, 0).

$S(0, 0) - \Delta S(\Delta Xs, \Delta Ys, 0,0)/4$: a disagreement with respect to the layer B at (0, 0).

Further, the quantity $S(0, 0) - \Delta S(\Delta Xs, \Delta Ys, 0, 0)$ becomes zero at (1, 1). This means, with regard to the disagreeing pixels obtained by aligning patterns at a plurality of positions, that the most suitable alignment is achieved by selecting the position where the number of disagreeing pixels is close to the linear sum of signals of disagreeing pixels at two positions.

Therefore, these expressions can be obtained: min $S(\Delta X, \Delta Y, 0, 0)/4$: a disagreement related with a layer which cannot be aligned at the position ($\Delta Xmin, \Delta Ymin$) and the position shifted therefrom by ($\Delta X, \Delta Y$).

$S(\Delta Xmin, \Delta Ymin) - \min \Delta S(\Delta X, \Delta Y, 0, 0)/4$: a disagreement related with a layer which cannot be aligned at the position ($\Delta Xmin, \Delta Ymin$) but can be aligned at the position shifted therefrom by ($\Delta X, \Delta Y$).

More generally, $\min \Delta S(\Delta X, \Delta Y, \Delta X, f, \Delta Yof)/4$: a disagreement related with a layer which cannot be aligned at the position ($\Delta Xmin + \Delta Xof, \Delta Ymin + \Delta Yof$) and the position shifted therefrom by ($\Delta X, \Delta Y$).

$S(\Delta Xmin + \Delta Xof, \Delta Ymin + \Delta Yof) - \min \Delta S(\Delta X, \Delta Y, \Delta Xof, \Delta Yof)/4$: a disagreement related with a layer which cannot be aligned at the position ($\Delta Xmin + \Delta Xof \Delta Ymin + \Delta Yof$) but can be aligned at the position shifted therefrom by ($\Delta X, \Delta Y$).

Accordingly, at the position ($\Delta Xmin + \Delta Xof, Ymin + \Delta Yof$) where $\min_j S(\Delta X, \Delta Y, \Delta Xof, \Delta Yof)/4$ is small and $S(\Delta min + \Delta Xof, \Delta Ymin + \Delta Yof - \min \Delta S(iX, \Delta Y, \Delta Xof, \Delta Yof)/4$ is large and the position where the image is shifted therefrom by ($\Delta X, \Delta Y$), many of normal portions which did not align at ($\Delta Xmin + \Delta Xof, \Delta Ymin + \Delta Yof$) come to be correctly aligned by shifting ($\Delta X, \Delta Y$) so as to be eliminated, and, in addition, the disagreements that do not match even if the image is shifted can be reduced.

In the case of FIG. 27, the positions where $$\min \Delta S(\Delta X, \Delta Y, 0, 0)/4 < Sth, \quad (2)$$

Sth: threshold value holds are (0, 0) and (1, 1), and the position where $$\min \Delta S(\Delta X, \Delta Y, \Delta Xof, \Delta Yof) \leq \min \Delta S(\Delta X, \Delta Y, 0, 0) \quad (3)$$

holds are five points (0, −1), (0, 0), (1, 0), (0, 1), and (1, 1). The layers A, B and C can all be correctly aligned at these positions, and it is found that the above technique was reasonable.

Figure 28C:
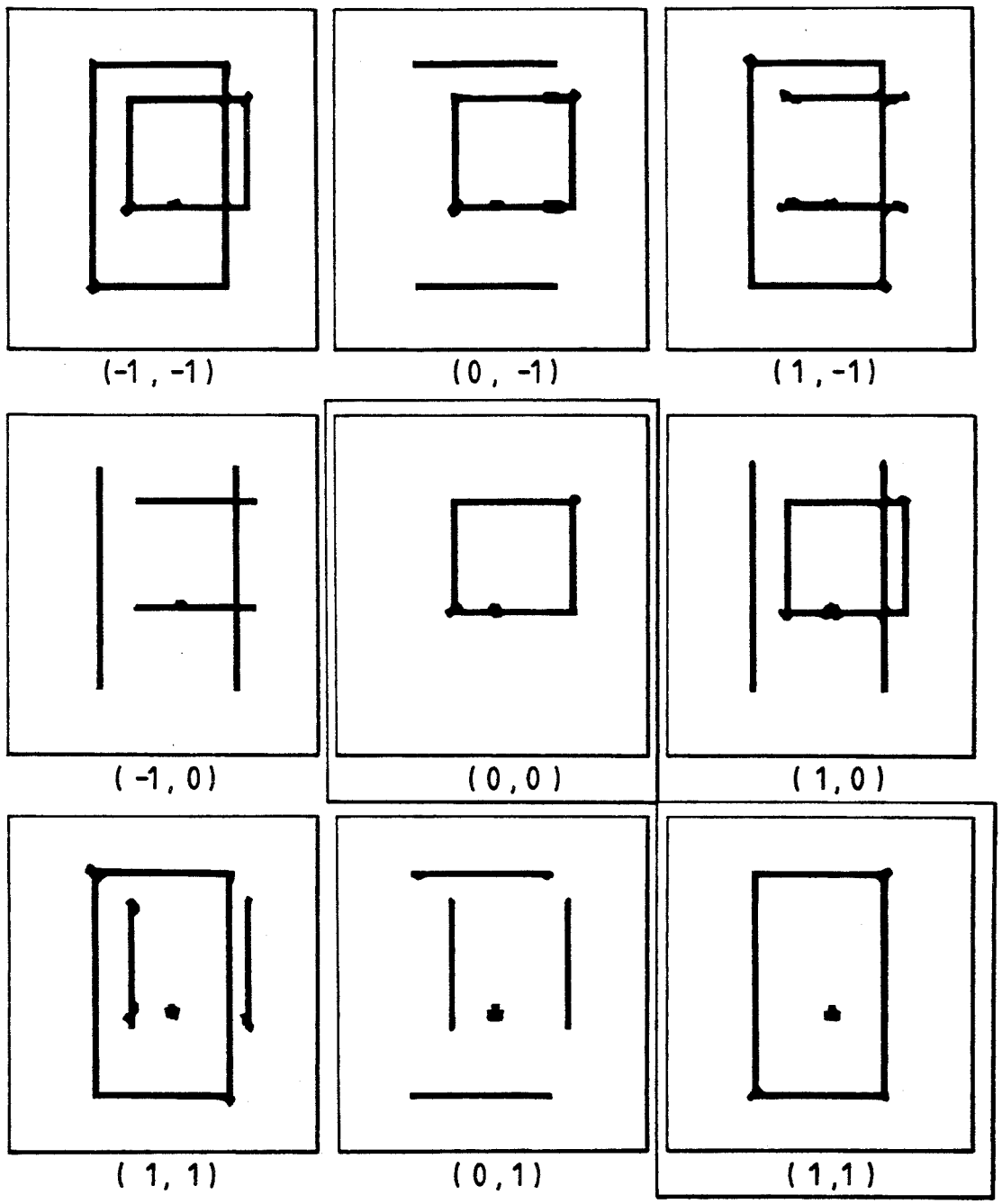

In the case of two-layer pattern, the above technique leads to an optimum solution. FIG. 28 is a diagram showing an example of an experiment (two-layer pattern) for compensating for interlayer alignment errors by shifting the image, i.e., a two-layer simulation pattern is illustrated. There are minute interlayer slippages between the detected image signal and the stored image signal. Referring to the diagram, the positions where $$\min \Delta S(\Delta X, \Delta Y, \Delta Xof, \Delta Y, f) \leq \min \Delta S(\Delta X, \Delta Y, 0, 0) < Sth \quad (4)$$

holds obtained by shifting the image by $(\Delta Xmin + \Delta Xof, \Delta min + \Delta Yof)$ and $(\Delta X, \Delta Y)$ are $(0, 0)$ and $(1, 1)$, where the layer A and the layer B each can be correctly aligned.

A specific method to detect $(\Delta Xs, \Delta Ys)$ will be given as follows:

If $S(\Delta Xmin, \Delta Ymin) \geq V_1$ (the number of disagreeing pixels is large)

(There are disagreements ... defects/interlayer slippages). Then, $$\text{if } S(\Delta Xmin, \Delta Ymin) - \min_{\nu X, \Delta Y} |\Delta S(\Delta X, \Delta Y, 0, 0)/4| \geq V_2,$$

The number of disagreeing pixels out of the disagreeing pixels $S(\Delta Xmin, \Delta Ymin)$ related to a pattern, which cannot be aligned at the position $(\Delta Xmin, \Delta Ymin)$ but can be aligned if the image is shifted by $(\Delta X, \Delta Y)$.

This value is large (the disagreements are considered to be interlayer slippages).

(The largest number of eliminable disagreements ... interlayer slippages.) Or, $$\text{if } \min \Delta S(\Delta X, \Delta Y, 0, 0) \leq V_3, \Delta X, \Delta Y$$

The number of disagreeing pixels out of $S(\Delta Xmin, \Delta Ymin)$, which cannot be aligned at the position $(\Delta Xmin, \Delta Ymin)$ and cannot be aligned even if the image is shifted $(\Delta X, \Delta Y)$ therefrom.

This value is small (the number of disagreements itself is small).

(Small number of disagreements ... eliminable.)

Then select $(\Delta Xmin + \Delta X, \Delta Ymin + \Delta Y)$ $(\Delta Xmin + \Delta Ymin)$.

Selection of the position where images are aligned.
endif $$\text{if } S(\Delta Xmin, \Delta Ymin) - \min_{\Delta X, \Delta Y} |\Delta S(\Delta X, \Delta Y, 0, 0)/4| \geq V_2,$$

The number of disagreeing pixels out of the disagreeing pixels $S(\Delta Xmin, \Delta Ymin)$ related to a pattern, which cannot be aligned at the position $(\Delta Xmin, \Delta Ymin)$ but can be aligned if the image is shifted by $(\Delta X, \Delta Y)$.

This value is large (the disagreements are considered to be interlayer slippages). (The largest number of eliminable disagreements ... interlayer slippages.)

Then, $$\text{if } |\min_{\Delta X, \Delta Y} \Delta S(\Delta X, \Delta Y, \Delta Xof, \Delta Yof)| \leq \min_{\Delta X, \Delta Y} |\Delta S(\Delta X, \Delta Y, 0)0|$$

The number of disagreeing pixels is small even at the position shifted $(\Delta X, \Delta Y)$ from the position $(\Delta Xmin + \Delta Xof, \Delta Ymin + \Delta Yof)$, which is the position obtained by adding an offset $(\Delta Xof, \Delta Yof)$ to the position $(\Delta Xmin, \Delta Ymin)$.

(The largest number of eliminable disagreements.)

Then, select $(\Delta Xmin + \Delta Xof + \Delta X, \Delta Ymin + \Delta Yof + \Delta Y)$, $(\Delta Xmin + \Delta Xof, \Delta Ymin + \Delta Yof)$.

Selection of the position for aligning the images.

endif
endif
endif

Alignment is performed at two arbitrary position eliminable disagreements at these positions are obtained, and the position where remaining disagreements are small in number is detected as the position where interlayer slippages are allowed to be present.

FIG. 12 is a block diagram showing another embodiment of the invention. The structure from the image sensor 4 to the AND circuit 19 is the same as that in FIG. 1. The detected image signal f and the stored image signal g are delayed by delay circuits 41a and 41b, and an area of 5×5 pixels of the delayed detected image signal f is sliced by a slicer circuit 42a of a similar structure to that of the slicer circuits 12a, 13a, and a state where images are shifted by ±2 pixels is provided. The delayed stored image signal g is synchronized with the position in the center of the 5×5 pixels by the slicer circuit 42b of a similar structure to that of the slicer circuits 12b, 13b. Then, using the outputs of the slicer circuits 42a and 42b, difference images between the detected image signals f shifted by ±2 pixels and the stored image signal g are detected by difference image detector circuits 43a to 43y. A minimum value detector circuit 44 detects the minimum value of the difference image signals output from the difference image detector circuits 43a to 43y at the positions output from the positional shift detector circuit 16 in the regions for which the binarized edge patterns as the outputs of the slicer circuits 13a and 13b are both zero (the non-edge regions detected as "0" in FIG. 21(d) by the OR circuit 39 obtaining the logical sum of the outputs of the slicer circuits 13a and 13b shown in FIG. 10). If either of the binarized edge pattern detected by the OR circuit 39 is "1", the minimum value is set, for example, to zero and the difference image output is turned into zero. A binarization circuit 45 is a circuit for binarizing the minimum difference image output from the minimum value detector circuit 44 with a predetermined threshold value Vth (for example, as shown in FIG. 22) thereby detecting such a defect as a discoloration and obtaining the logical product of it and the output of the AND circuit 19.

Figure 22C:
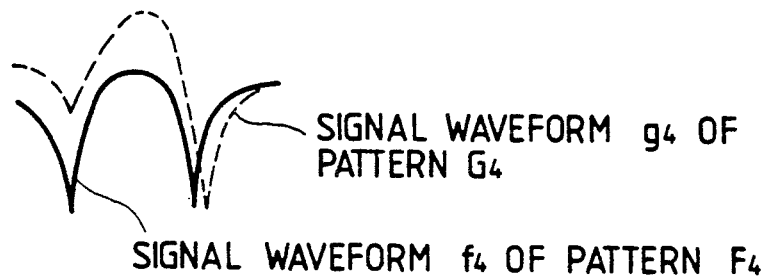
Figure 22D:
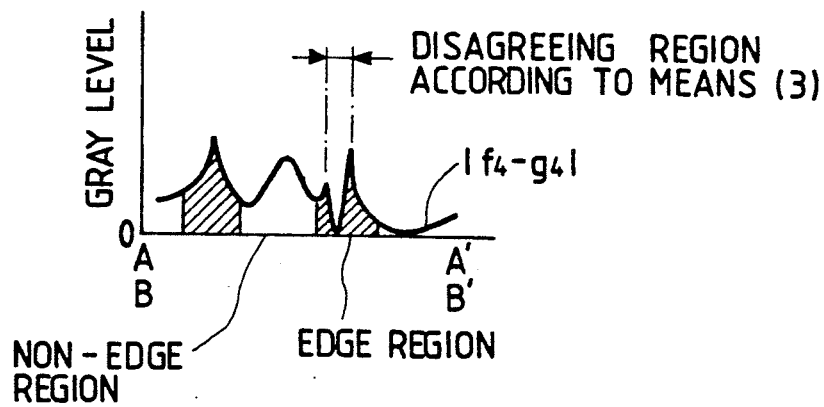
Figure 22E:
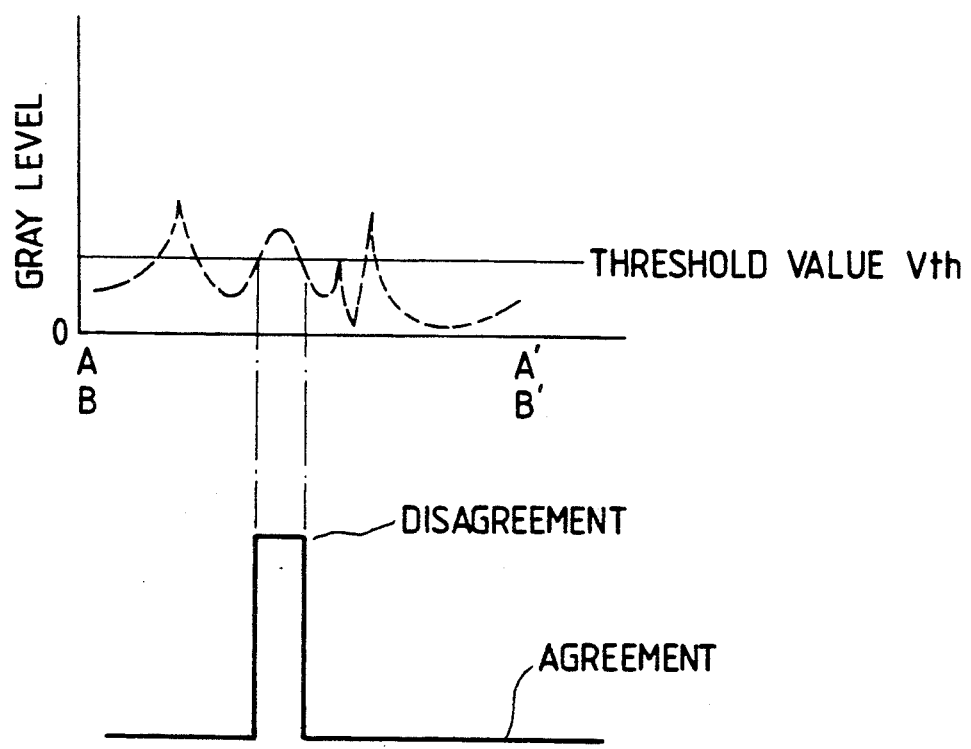

With the described arrangement, the difference image detector circuits 43a to 43y detect the difference image (shown in FIG. 22(d) as "Difference Signal Waveform") between the detected image signal (signal waveform) f4 of the pattern F4 and the detected image signal (signal waveform) g4 of the pattern G4 shown in FIG. 22(c). The minimum value detector circuit 44, in the non-edge region detected as "0" by the OR circuit 39 for obtaining the logical sum of the outputs of the slicer circuits 13a and 13b, obtains the minimum value, within the region of the positions output from the positional shift detector circuit 16 (where there are no positional shift), out of the difference image signals output from the difference signal detector circuits 43a to 43y. The binarization circuit 45 outputs a signal "1" when the above mentioned minimum value of the difference signal is larger than a predetermined threshold value Vth and obtains the logical sum of this signal and the output of the AND circuit 19 and, therefore, a defect such as discoloration can be detected as shown in FIG. 22(e).

As another embodiment, such an arrangement is possible, in which the binarization circuit 45 in FIG. 12 is eliminated, the minimum value of the difference image signals output from the difference image detector circuits 43a to 43y within the range of the positions output from the positional shift detector circuit 16 (where there is no positional shift) is detected without using the binarized edge pattern signal detected by the OR circuit 39, and the minimum value of the difference image signal is binarized by the minimum value detector circuit 44 with a threshold value varying in accordance with the signal indicative of the polarity disagreement from the AND circuit 19, that is, with a lower threshold value in the region where the polarities output from the AND circuit 19 are in disagreement and with a higher threshold value in another region (where the polarities are not in disagreement), and thus, various defects (such as dimensional defects and decoloration defects) can be detected according to the obtained binarized signal.

As another embodiment, the threshold value Vth used by the binarization circuit 45 in FIG. 12 may be such as expressed, with the detected image signal f and the stored image signal g respectively represented by f(x, y) and g(x, y), as $$Vth(x, y) = C1 \min\{f(x, y), g(X, y)\} + C2,$$

where C1 and C2 are constants. If the output of the minimum value detector circuit 44 is binarized with the above threshold value Vth(x, y), most suitable binarization in accordance with brightness of the circuit pattern can be achieved and various defects detected. At this time, the threshold value is determined according to the detected image signal input to the minimum value detector circuit 44, depending on the gray level of the pixel corresponding to the positional shift minimizing the number of disagreeing pixels obtained by the positional shift detector circuit 16 and on the gray level of the corresponding pixel of the stored image signal.

Figure 13:
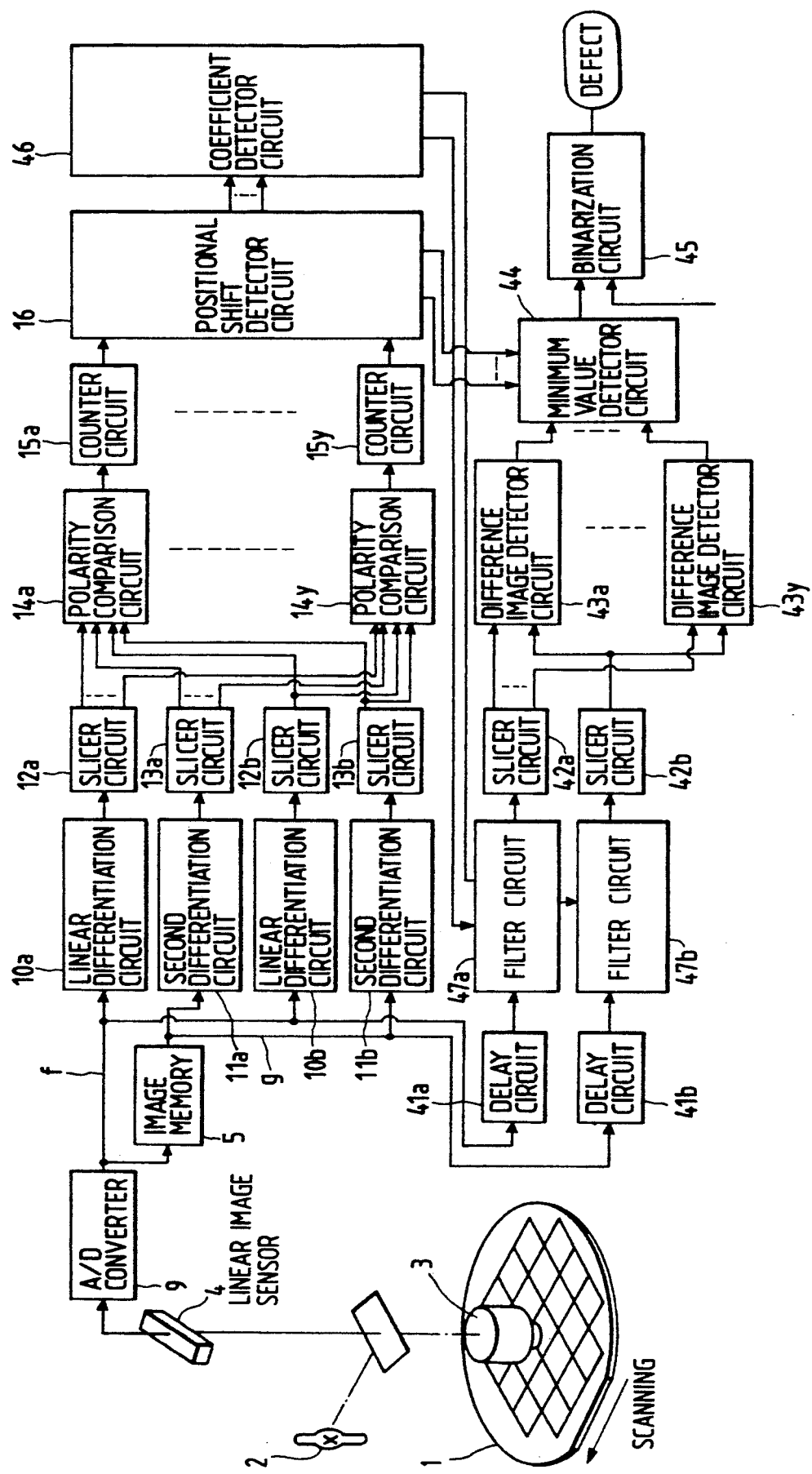
FIG. 13 is a diagram showing a further embodiment for detecting defects in circuit patterns according to the present invention different from that in FIG. 12.

FIG. 13 is a block diagram showing another embodiment for performing a filtering operation of the image. The structure from the image sensor 4 to the positional shift detector circuit 16 is the same as that of the arrangement in FIG. 1. A coefficient detector circuit 46 is a circuit receiving values of disagreeing pixels from the positional shift detector circuit 16 to thereby obtain coefficients aij and bij for the below described filter circuits 47a and 47b. The filter circuits 47a and 47b are circuits having filters with coefficients aij and bij convoluted in image signals delayed by delay circuits 41a and 41b. A slicer circuit 42a slices a region of 5×5 pixels from the detected image signal f subjected to the filtering and provides a state of the images shifted by ±2 pixels. A slicer circuit 42b synchronizes the stored image signal g subjected to the filtering with the position in the center of the 5×5 pixels. Then, the difference image signals between the detected image signal f shifted by ±2 pixels and the stored image signal g are obtained by difference signal detector circuits 43a to 43y using outputs of the slicer circuits 42a and 42b. A minimum value detector circuit 44 detects the minimum value of the difference image outputs from the difference image detector circuits 43a to 43y at the positions output from the positional shift detector circuit 16. A binarization circuit 45 is a circuit for binarizing the output of the minimum value detector circuit 44.

In obtaining the coefficients, a quadratic function or the like is applied to the curve in FIG. 23 and the imaginary position where the number of disagreeing pixels becomes a minimum is obtained by such means as the method of least squares to the accuracy below a unit of one pixel and, then, the difference between this position and the position where the number of the disagreeing pixels becomes a minimum is detected in units of pixels. Thereafter, the filter coefficients aij and bij for shifting the detected image signal and the stored image signal toward each other by half the above obtained difference are obtained.

For example, if the detected image signal and the stored image signal can be aligned by shifting the detected image signal 0.2 pixel in the x direction and 0.3 pixel in the y direction and shifting the stored image signal equal quantities in the opposite directions, the coefficients are obtained as $$[aij] = \left( \begin{bmatrix} 0 & 0 & 0 \\ 0 & 0.8 & 0.2 \\ 0 & 0 & 0 \end{bmatrix} + \begin{bmatrix} 0 & 0 & 0 \\ 0 & 0.7 & 0 \\ 0 & 0.3 & 0 \end{bmatrix} \right)/2$$

$$= \begin{bmatrix} 0 & 0 & 0 \\ 0 & 0.75 & 0.1 \\ 0 & 0.15 & 0 \end{bmatrix}$$

$$[bij] = \begin{bmatrix} 0 & 0.15 & 0 \\ 0.1 & 0.75 & 0 \\ 0 & 0 & 0 \end{bmatrix}$$

Although the above example enables accurate registering of two images, two images may be shifted so that there is a for example, of ½ pixel therebetween and the minimum value may be detected at a plurality of positions ΔX=0 and ΔX −1 as shown in FIG. 25(b) to thereby positively allow existence of a shape difference of ½ pixel.

Figure 26A:
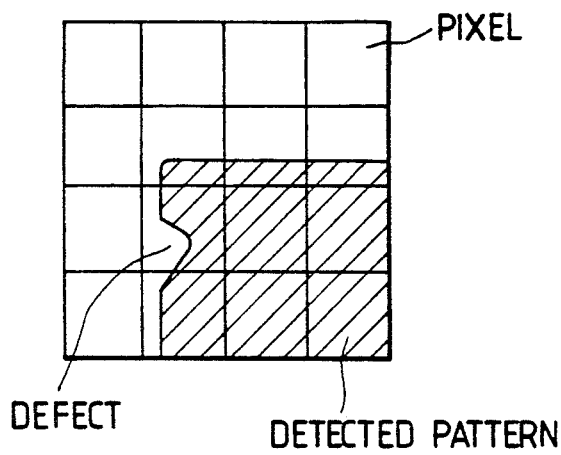
FIGS. 26(a) to 26(c) are diagrams in which a detected image signal (pattern) and a stored image signal (pattern) are brought into a registered state.
Figure 26B:
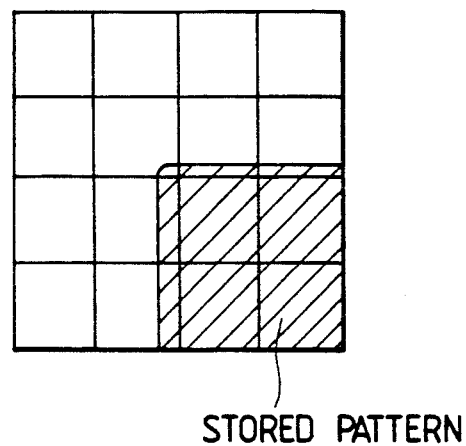
Figure 26C:
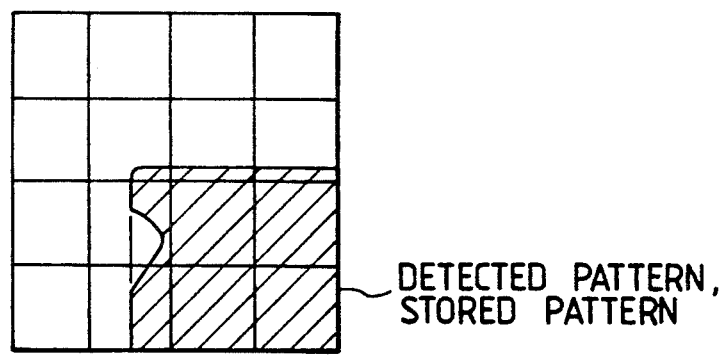

With the arrangement described above, images can be aligned with accuracy at desired degrees. For example, as shown in FIG. 26, the sampling error at the time of image inspection can be compensated for. Here, FIG. 26(a) shows a detected pattern, FIG. 26(b) shows a stored pattern, and FIG. 26(c) shows the detected pattern and the stored pattern after undergoing the filtering.

Although an example where existence of defects was determined by detecting difference images of gray images was shown in FIG. 13, the determination may be achieved by means of polarity comparison as shown in FIG. 1 or by a combination of the polarity comparison and difference image detection as shown in FIG. 12.

With the above described arrangements, the accuracy in alignment is greatly improved from that in the unit of one pixel in the prior art to that in the unit of a fraction of pixel and, thus, it has become possible to detect more minute defects. It is thus possible to detect minute defects even if there are differences in detected waveforms of gray images at normal positions, and therefore, erroneous detection by variations in thickness of pattern films, differences in the condition of down slope of the pattern edges, interlayer slippages, or sampling errors at the time of inspection can be prevented. Since the alignment accuracy has been improved, detection of minuter defects are made possible. Further, not only the defects in shape but also discoloring and the like can be detected without fail. Additionally, not only existence of defects but also the dimension can be detected accurately.

Figure 29:
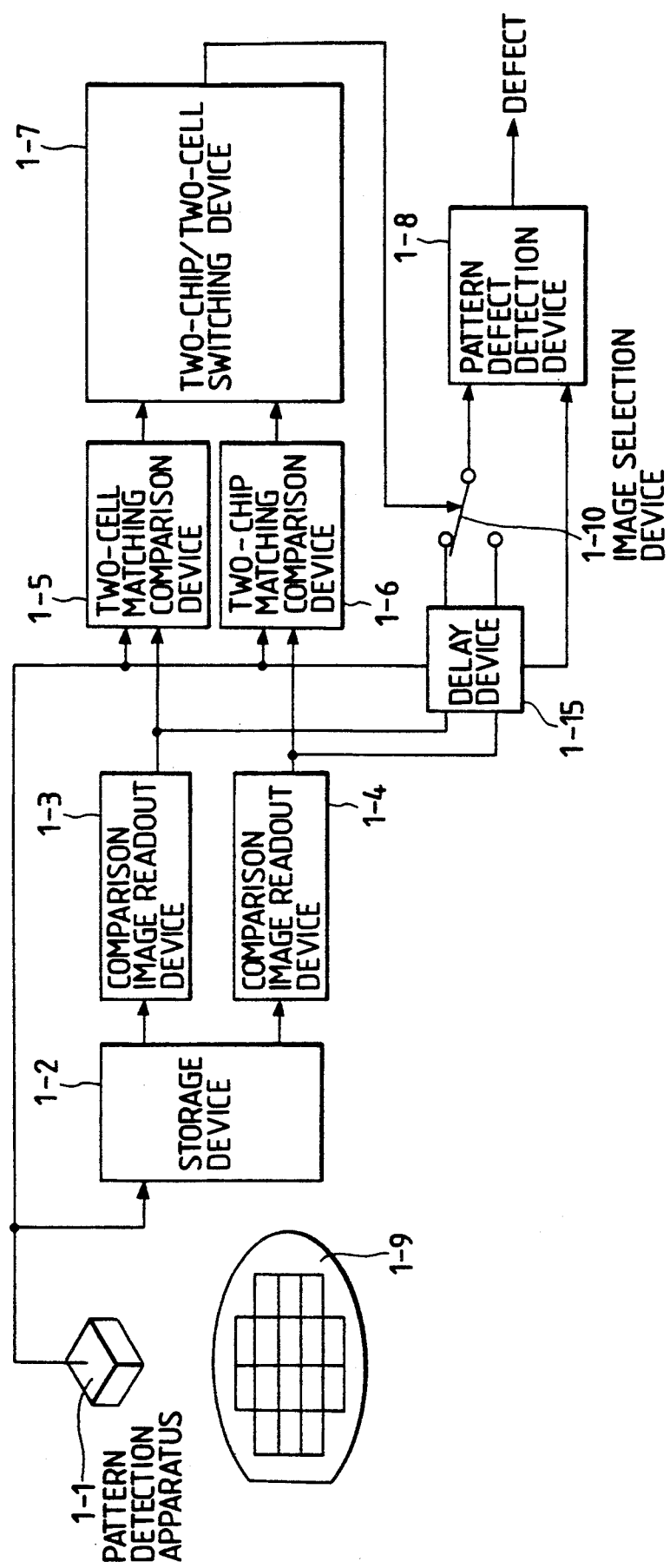
FIG. 29 is a block diagram of another embodiment for detecting a pattern defect according to the present invention.

According to another embodiment as illustrated in FIG. 29, an apparatus for detecting a defect in a pattern according to the two-chip and two-cell comparison of the present invention is now described. A pattern on a wafer 1-9 is previously detected by a pattern detection apparatus 1-1 and stored in a storage device 1-2, and then, a new pattern is detected by the pattern detection apparatus as a reference image pattern or detected image pattern. In synchronism with this pattern detection, a comparison image readout device 1-3 extracts, from the entire portion of the pattern previously stored in the storage device 1-2, the patterns at the coordinates for two-cell comparison with the reference image pattern or detected image pattern, in the portion where the two-cell comparison method is applicable. In like manner, a comparison image readout device 1-4 extracts, from the entire portion of the pattern previously stored in the storage device 1-2, the patterns at the coordinates for two-chip comparison with the reference image pattern or detected image pattern, in the portion where the two-cell comparison method is not applicable (where two-chip comparison is applicable).

The comparison image patterns from the readout devices 1-3 and 1-4 are subjected to matching comparison with the reference image or detected image pattern, in a two-cell matching comparison device 1-5 and in a two-chip matching comparison device 1-6, respectively, and the degrees of agreement as the results of matching comparison are output therefrom. Depending on the degrees of agreement, the comparison method providing the largest degree of agreement of these degrees of agreement is selected by a two-chip/two-cell switching device 1-7. The comparison image pattern according to the selected comparison method is subjected through an image selection device 1-10 to comparison with the reference image pattern, or detected image pattern, in a pattern defect detection device 1-8 after such patterns are subject to appropriate delay in delay device 1-15 and, thereby, the detection of a pattern defect is achieved. The comparison image patterns, and the reference image or detected image pattern, to be supplied to the pattern defect detection device 1-8 are temporarily stored in the delay device 1-15 before they are supplied to the pattern defect detection device 1-8 while other patterns are being subjected to the pattern matching comparison.

Figure 30:
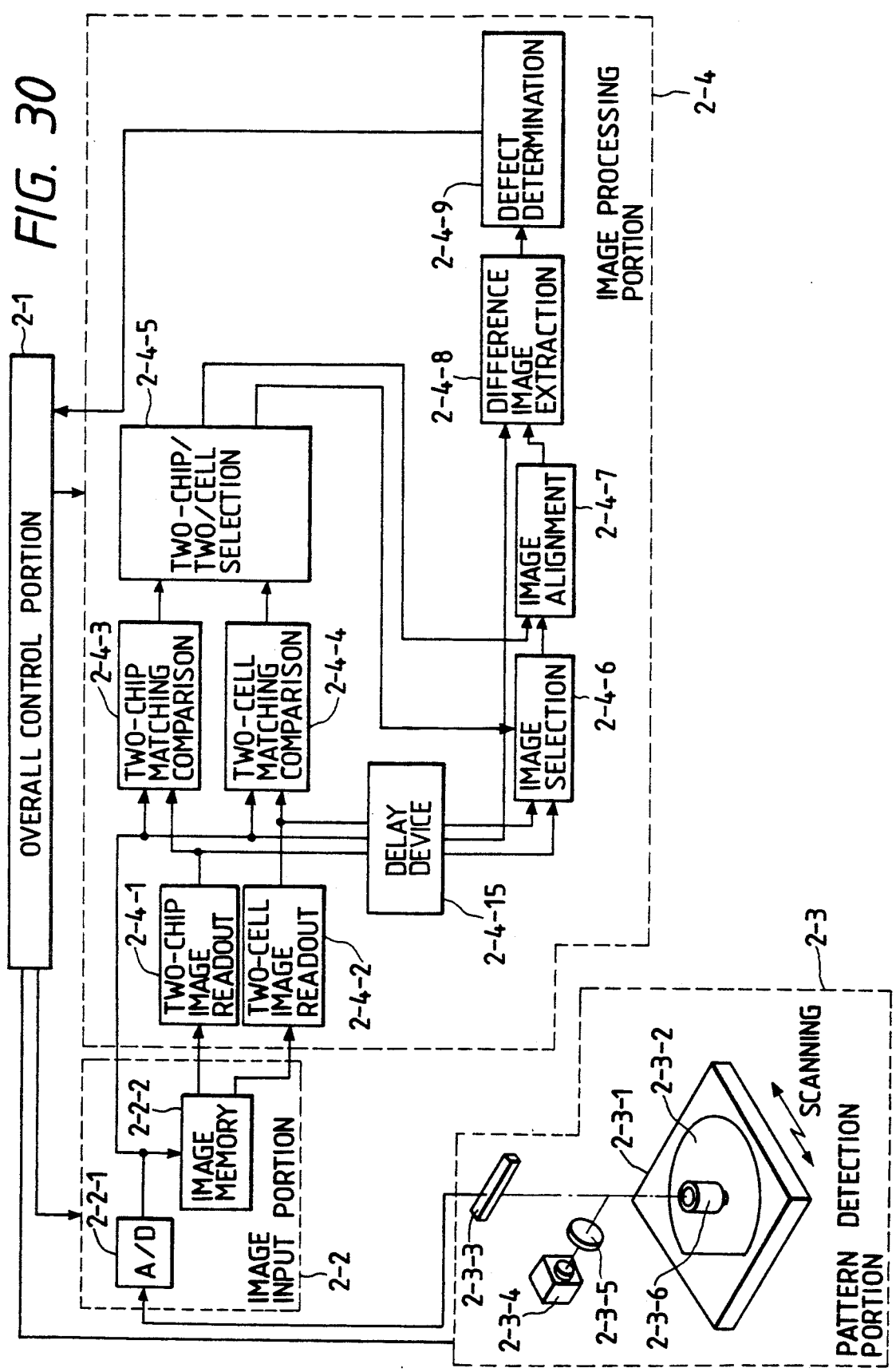
FIG. 30 is a more detailed block diagram of the apparatus for detecting a pattern defect according to the present invention.

FIG. 30 is a more detailed block diagram showing the apparatus for detecting a pattern defect. In the present example, an LSI wafer pattern inspecting apparatus is utilized and, hence, the pattern is illustrated as a pattern on a wafer, but of course the apparatus is applicable to other patterns such as TFT patterns. In this example, the entire apparatus includes a pattern detection portion 2-3, an image input portion 2-2, an image processing portion 2-4, and an overall control portion 2-1, of which the overall control portion 2-1 performs control of an XY stage and management of storage and display of information on a defect from the image processing portion 2-4 and overall sequential control. The operation of the apparatus will be described below.

After every portion is initialized upon instruction from the overall control portion 2-1, a wafer 2-3-2 is illuminated by an illuminating light beam from an illuminating portion 2-3-4 through an illuminating lens 2-3-5, for example, and a two dimensional pattern on the wafer is detected by a linear image sensor 2-3-3 through an objective lens 2-3-6, in synchronism with the scanning by movement of the XY stage 2-3-1. A pattern detection signal is detected through photoelectric transfer by the linear image sensor 2-3-3, digitized by an A/D converter 2-2-1 within the image input portion 2-2, and sequentially stored into an image memory portion 2-2-2, whereby the two-dimensional pattern is stored in the image memory 2-2-2 in the order of predetermined addresses. Thus, the contents in the image memory 2-2-2 is retained as a stored image and the two-dimensional pattern on the wafer 2-3-2 is detected again, and the pattern detection signal at this time is used as a reference image signal. At the same time, the comparison signal is read out from the image memory, and then, the image memory is overwritten with the detection signal in preparation for comparison with the signal of the next chip. In synchronism with this reference image signal, an image for two-chip comparison and an image for two-cell comparison are taken out by a two-chip image readout portion 2-4-1 and a two-cell image readout portion 2-4-2, respectively.

Figure 31A:
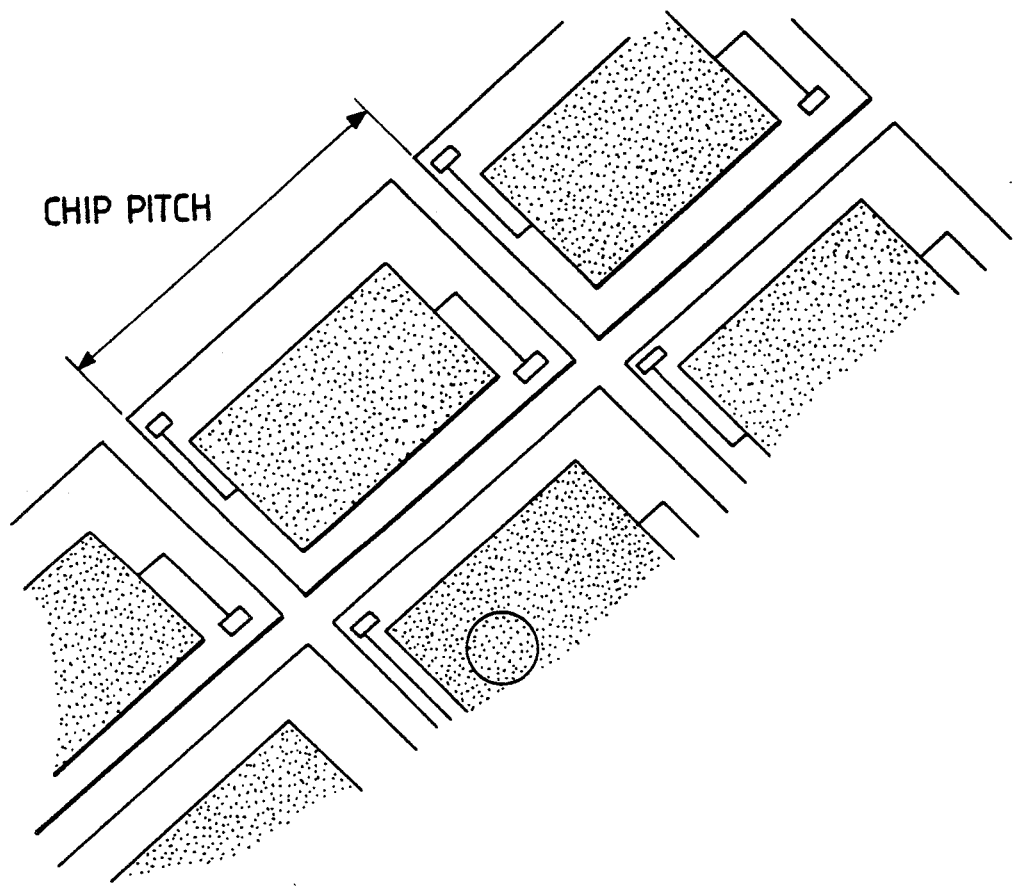
FIG. 31(a) is a view showing a wafer in perspective and FIG. 31(b) is a view showing an enlarged state of the portion enclosed with a circle in FIG. 31(a)
Figure 31B:
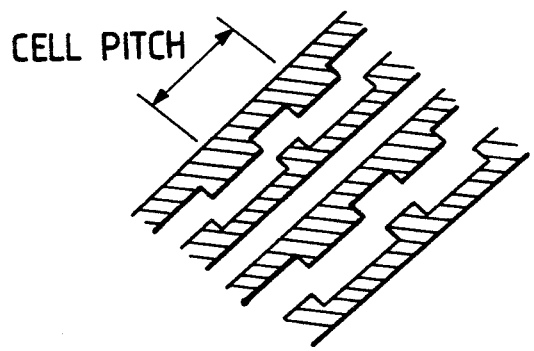

Describing now the two-chip image readout portion 2-4-1 referring to FIG. 31(a), in which a wafer is shown in perspective, the two-chip image readout portion 2-4-1 functions to take out images for two-chip comparison by referencing to predetermined addresses in the image memory portion 2-2-2 in view of the fact that the coordinates for two-chip comparison and the reference image are multiples of one chip pitch apart. Describing now the two-cell image readout portion 2-4-2 referring to FIG. 31(b), in which an enlarged view of the portion enclosed with a circle in FIG. 31(a) is shown, the two-cell image readout portion 2-4-2 functions to take out images for two-cell comparison by referencing to predetermined addresses in the image memory portion 2-2-2 in view of the fact that the coordinates for two-cell comparison and the reference image are multiples of one cell pitch apart.

While the reference image is subjected to matching comparison with the image for two-chip comparison and the image for two-cell comparison in a two-chip matching comparison portion 2-4-3 and a two-cell matching comparison portion 2-4-4, respectively, the manner in which the two-chip matching comparison is performed will be described referring to FIG. 32.

Figure 32:
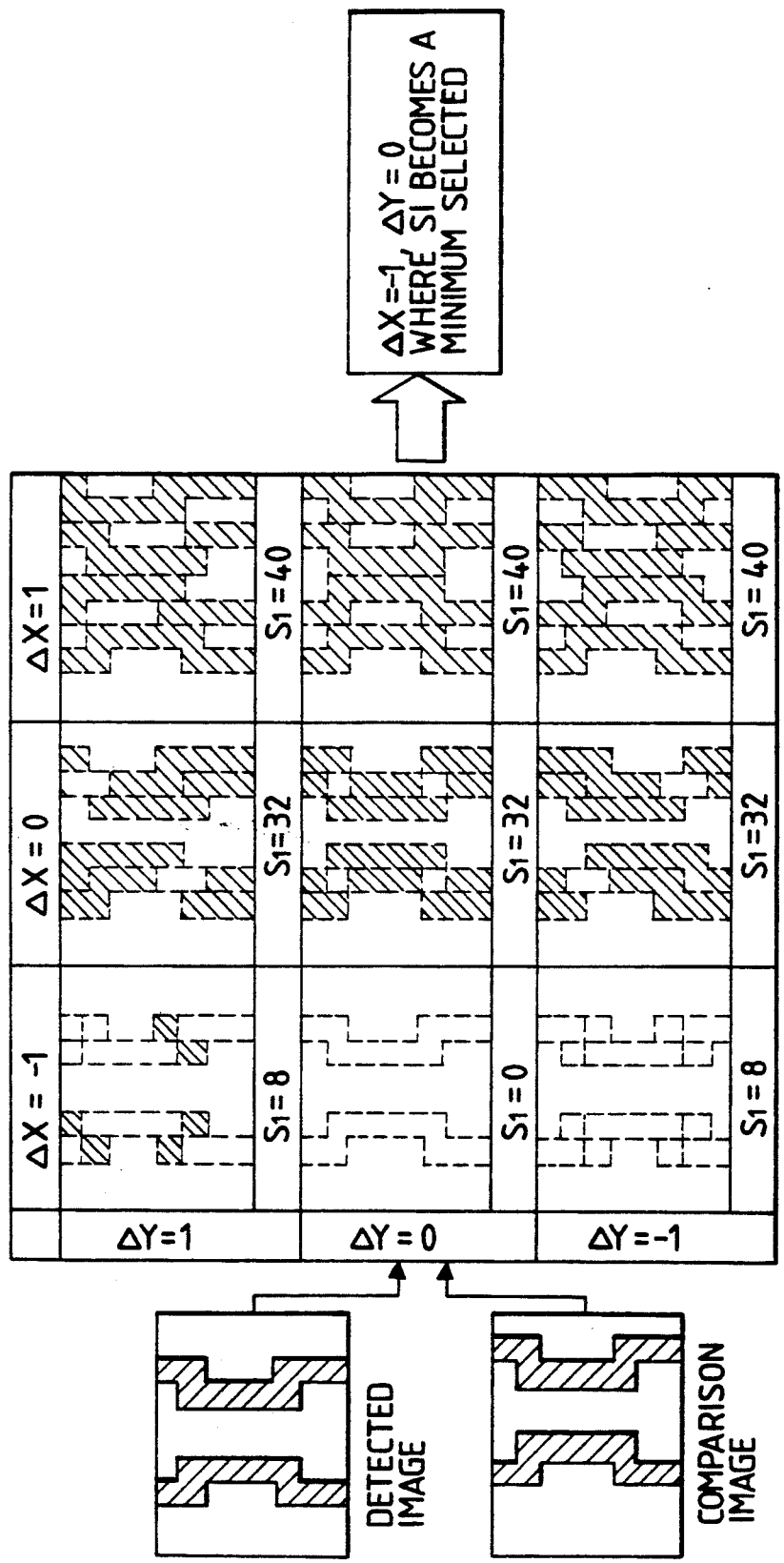
FIG. 32 is a diagram for explaining a matching comparison process performed in a two-cell and a two-chip matching comparison portion in FIG. 30.

As shown in FIG. 32, the differences between the reference image (detected image) and the two-chip comparison image with the two-chip comparison image shifted in the directions of $\Delta X$ and $\Delta Y$ by $\pm \delta$ pixels, i.e., the positional shift tolerance ($\delta = 1$ is assumed in the present example, but this value may generally be determined depending on dimensional accuracy of the object of inspection and the positioning accuracy of the defect detecting apparatus and a suitable value therefor may be established according to requirements), are arranged to be obtained from the calculation according to the expression (5), $$S1(\Delta i, \Delta j) = \Sigma\Sigma |f(i, j) - g1(i + \Delta i, j + \Delta j)| \quad (5)$$

f(i, j) represents the value of the reference image at the pixel (i, j), g1(i, j) represents the value of the two-chip comparison image at the pixel (i, j), and S1(Δi, Δj) represent the differences between these images at image shift amounts (Δi, Δj). Further, ΣΣ indicates summation performed over all the area of images where the positional shifts are calculated and Δi and Δj are adapted to take values from −1 to +1. Quite similar calculation to the above is performed also in the two-cell matching comparison portion 2-4-4. That is, the differences between the reference image and the two-cell comparison image with the two-cell comparison image shifted in the directions of ΔX and ΔY by ±δ pixels, i.e., the positional shift tolerance, are arranged to be obtained, whereby the differences corresponding to the positional shifts are obtained as degrees of agreement (matching values), from the calculation according to the expression (6), $$S2(\Delta i, \Delta j) = \Sigma\Sigma |f(i, j) - g2(i + \Delta i, j + \Delta j)| \quad (6)$$

where f(i, j) represents the value of the reference image at the pixel (i, j), g2(i, j) represents the value of the two-cell comparison image at the pixel (i, j), and S2(Δi, Δj) represent the differences between these images at image shift amounts (Δi, Δj), and, further, ΣΣ indicates summation performed over all the area of images where the positional shifts are calculated and Δi and Δj are adapted to take values from −1 to +1.

In a two-chip/two-cell selection portion 2-4-5, searching is effected for the lowest value of the degrees of agreement S1 and S2, and the lowest value thereby obtained is determined to represent the highest degree of agreement and the related method of comparison is selected and, further, the positional shift amount where the minimum value is provided is obtained. More specifically, the minimum value is obtained from the degrees of agreement at positions corresponding to various positional shift amounts, and if the minimum value is obtained from the degrees of agreement S1, the two-chip comparison method is selected, and if the minimum value is obtained from the degrees of agreement S2, the two-cell comparison method is selected. Further, the image shift amount, or positional shift amount, (Δi, Δj), where the minimum value is provided is also obtained. According to the comparison method selected by the two-chip/two-cell selection portion 2-4-5, the comparison image related to the comparison method is selected in an image selection portion 2-4-6, and the thus selected comparison image is subjected to a position adjustment in an image alignment portion 2-4-7 in accordance with the positional shift amount obtained from the two-chip/two-cell selection portion 2-4-5, and then, the comparison image is subjected to extraction of a difference image between the same and the reference image in a difference image extraction portion 2-4-8 according to expression (7), $$S(i, j) = |f(i, j) - g3(i, j)| \quad (7)$$

where f(i, j) represents the value of the reference image at the pixel (i, j), g3(i, j) represents the value of the comparison image adjusted for position at the pixel (i, j), and S(i, j) represents the value of the difference image at the pixel (i, j). As shown, the images are subject to appropriate delay by delay device 2-4-15.

The value S(i, j) is binarized in a defect determination portion 2-4-9 with a threshold value Vth for defect determination and area, width, projected length, or other feature parameters at the position where the difference is present are extracted and so that the presence of a defect is determined. Thus, when the comparison image to be compared with the reference image is selected, having positional shifts allowed, detection of a defect can be achieved even if the positioning accuracy is not very good.

In the foregoing, the general operation of an embodiment of the apparatus for detecting a pattern defect according to the present invention has been described, but the present invention is not limited to such embodiment. For example, in the detection of the two-dimensional pattern on a wafer, the two-dimensional pattern may be detected with a TV camera while an XY stage is allowed to effect step-movement, and a combination of a point type sensor, such as a photomultiplier, and a scanning mechanism, or any type of sensor may be utilized.

Instead of calculating the difference of image between the reference image and the comparison image according to the expressions (5) and (6) and obtaining the difference between the images corresponding to each positional shift amount as the matching value, it is possible to extract an edge by subjecting each of the reference image and the comparison image to filtering, calculate the difference between images with respect to the edge images according to expressions (5) and (6), and obtain the differences between the images as the matching values corresponding to the positional shift amounts, or it is also possible to subject each of the reference image and the comparison image to filtering and then binarization, calculate, according to expressions (5) and (6), the differences between images with respect to the edge binarized images obtained as above, and obtain the differences between the images corresponding to the positional shift amounts as the matching values. When matching values are obtained on the basis of the edge image, the result is scarcely affected by difference in the brightness of pattern between the reference image and the comparison image. Even if the quantity of the pattern detection light beam is changed, the position of the edge as a pattern boundary is not changed and, hence, matching values can be obtained by comparing the edge positions not affected by the change in the quantity of the detecting light beam.

Further, by preparing the object of comparison at the time of two-cell comparison or two-chip comparison not from one coordinate but from a plurality of coordinates so that the reference image is compared with each of such objects of comparison, the least matching value is selected. In other words, when a reference image is compared with each of a plurality of comparison images, even if a large defect is present in any of the comparison images, the probability of the presence of a defect in all of the other comparison images is very low, and hence, selection of the comparison method can be achieved.

Additionally, in view of the fact that the difference between the coordinates for two-cell comparison and the reference image is equal to an integer multiple of the cell pitch by allowing the two-cell readout portion to refer to a predetermined address which is an integer multiple of the cell pitch to thereby read out an image for two-cell comparison, image comparison at a distance of an integer multiple of the cell pitch is achievable and the difference in coordinate can be set to an integer multiple of the size of the pixel. Thus, it is possible to effect image comparison without being affected by sampling error at the time of pattern detection. For example, if a cell is compared with its adjoining cell in a case where the cell pitch is 5 μm and the pixel size is 0.3 μm, the distance measured in pixels may become 16.67 (=5 μm/0.3 μm), not an integer. This indicates that the comparison is made between one image in the first pixel and another image in the 17th pixel and involves an error of 0.33 pixel. Then, if comparison is made between the first cell and the third cell, the difference measured in pixels becomes 50 (=5 μm×3/0.3 μm), an integer. By doing the comparison between the first pixel and the 50th pixel, the comparison can be achieved without an error of a fraction of one pixel size.

Further, by having various parameters to be provided to the difference image readout portion and the defect determination portion set to suitable values according to the comparison method selected by the two chip/two-cell selection portion, it becomes possible to have such parameters as the threshold value for determining existence of a defect in the portion where two-cell comparison is applicable made lower than that in the portion where two-cell comparison is not applicable and, therefore, to detect a smaller defect.

Figure 33:
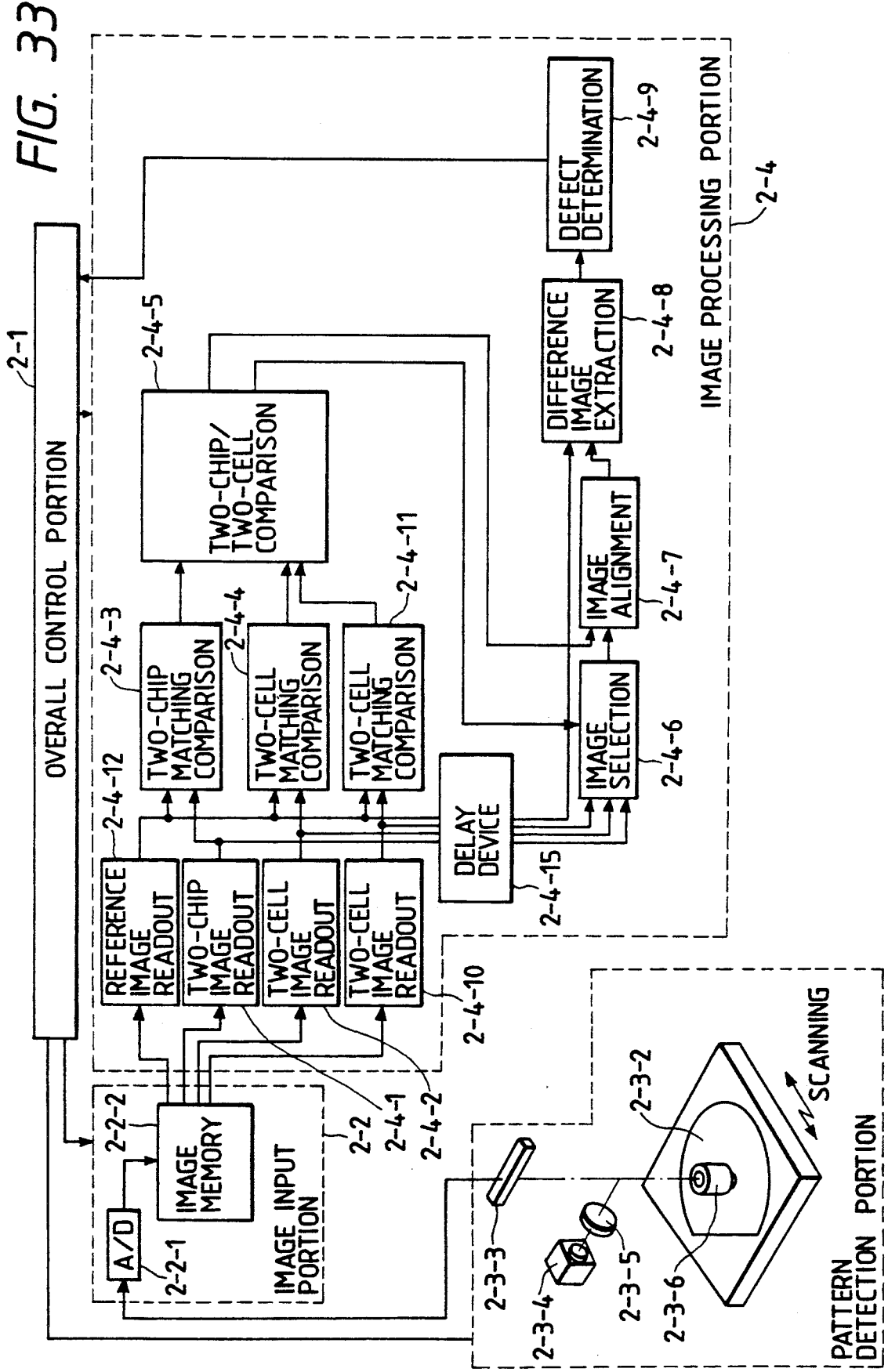
FIG. 33 is a more detailed block diagram in accordance with the present invention.
Figure 34:
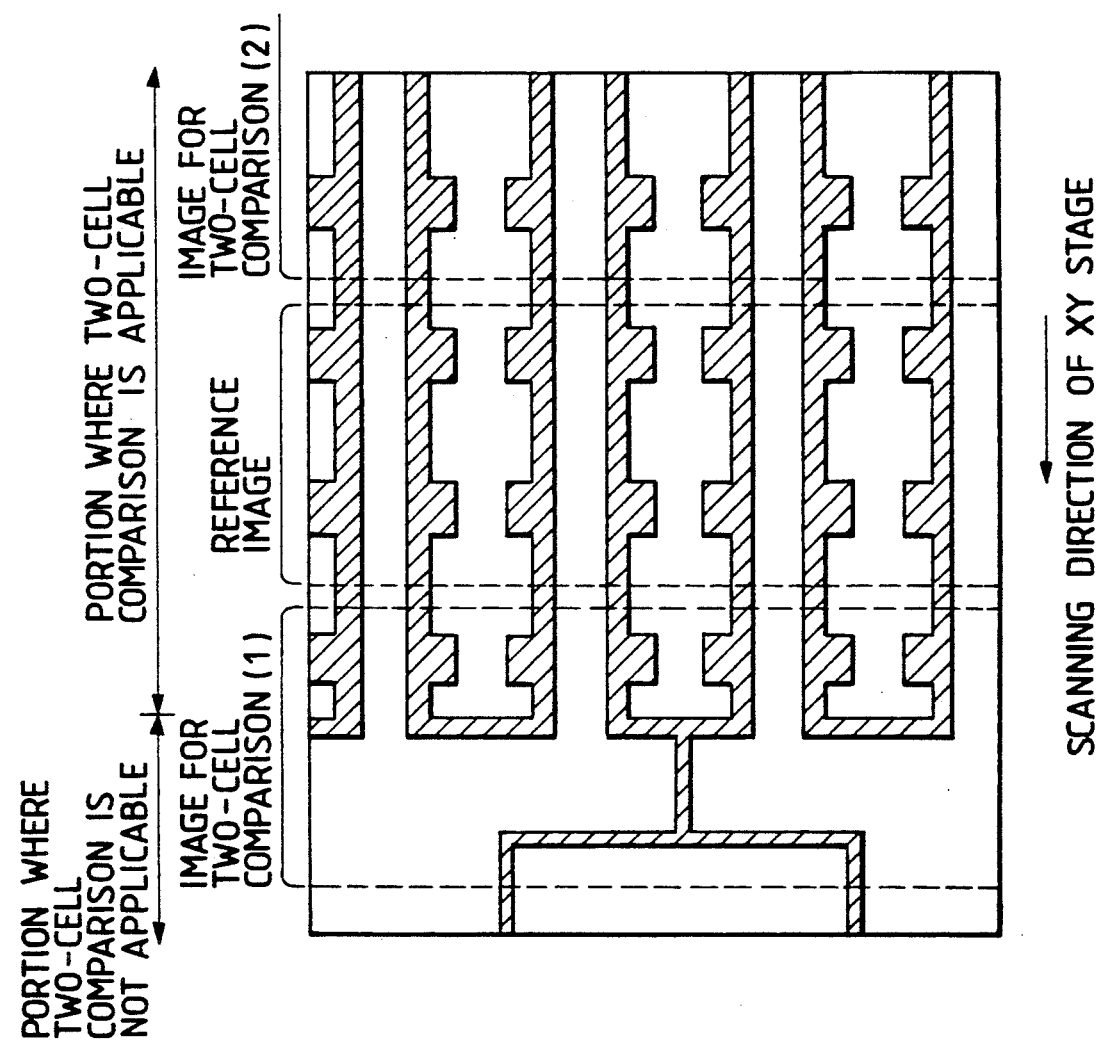
FIG. 34 is a diagram for explaining the possibility of two-cell comparison in the case where two-cell comparison images are established at both sides of a reference image.
Figure 35A:
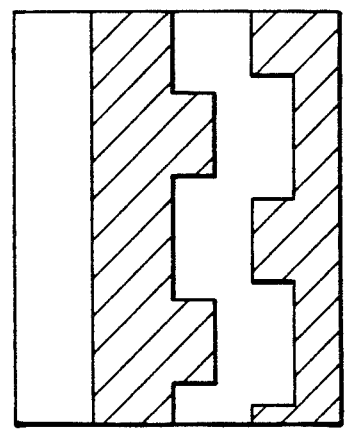
FIGS. 35(a), 35(b), and 35(c) are diagrams of a stored image, a detected image, and a difference of the patterns (difference as the result of comparison) for explaining a method for detecting a defect in a pattern in the prior art.
Figure 35B:
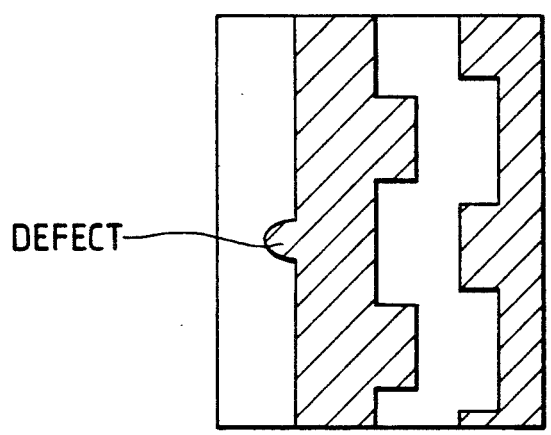
Figure 35C:
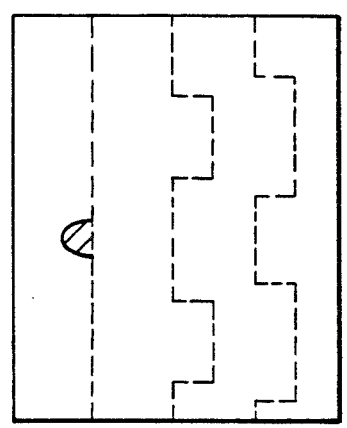
Figures 36A, 36B, 36C:
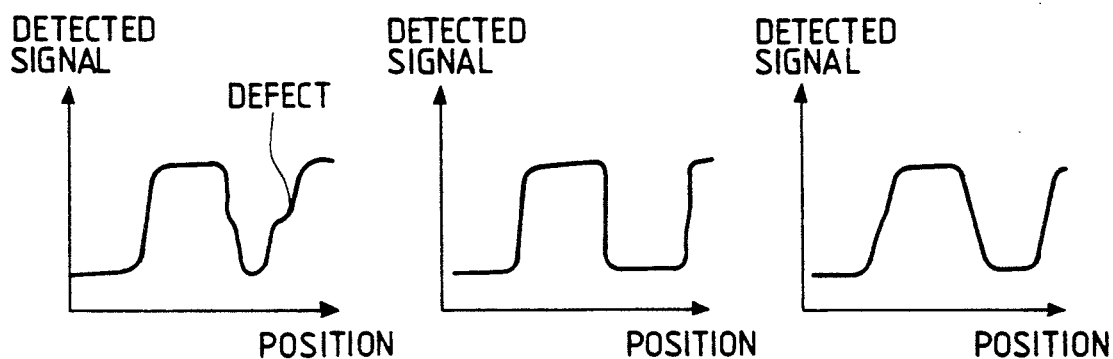
FIGS. 36(a) to 36(e) are diagrams for explaining the difference in occurrence of errors in the normal portion between that occurring in the two-cell comparison method and that occurring in the two-chip comparison method.
Figure 36D:
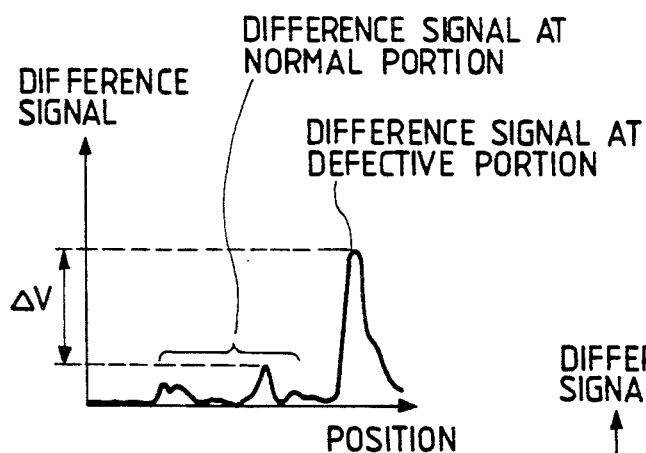
Figure 36E:
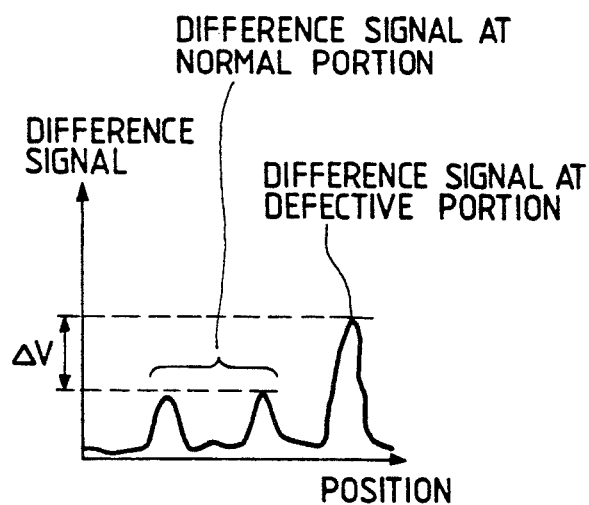

Another embodiment of an apparatus for detecting a pattern defect is shown in FIG. 33, wherein the same reference numerals are utilized to designate like parts in FIG. 30 and the difference from FIG. 30 is basically that the reference image is taken out from the image memory portion and a plurality of two-cell comparison images are read out and each of the read-out two-cell comparison images together with the reference image are subjected to matching comparison in the two-cell matching comparison portions. As described with the arrangement of FIG. 30, a two-dimensional pattern on a wafer 2-3-2 is stored into the image memory portion 2-2-2, but it is different from the case in the FIG. 30 that the reference image is taken out from the image memory portion 2-2-2. A reference image readout portion 2-4-12 refers to a predetermined address in the image memory portion 2-2-2, whereby the reference image is taken out. This reference image together with each of a two-chip comparison image and a two-cell comparison image are subjected to matching comparison in a two-chip matching comparison portion 2-4-3 and a two-cell matching comparison portion 2-4-4 as with the arrangement in FIG. 30, but in the present embodiment, another two-cell comparison image at a different coordinate is taken out by a two-cell image readout portion 2-4-10 and the two-cell comparison image taken out thereby together with the reference image are subjected to matching comparison in a two-cell matching comparison portion 2-4-11. In the present embodiment for simplicity of explanation, two sets of two-cell comparison images are shown to be simultaneously taken out, but that number is not limited to two. Generally, it is arranged such that more than two of images can be taken out. The same as in the case of FIG. 30, a two-chip/two-cell selection portion 2-4-5 searches for the minimum value related to the degrees of agreement corresponding to various shift amounts from the two-chip matching comparison portion 2-4-3 and the two-cell matching comparison portions 2-4-4, 2-4-11, and determines the minimum value to represent the highest degree of agreement. Thereupon, the related comparison method is selected and the shift amount providing the minimum value is obtained.

Other operations than described above are the same as those as described with respect to the arrangement of FIG. 30 and the characteristic of this embodiment is that a plurality of the two-cell comparison images are taken out and each of such comparison images and the reference image are subjected to matching comparison. The two-cell comparison images can be set to be at both sides of the reference image. If so set, even if the reference image is located in the vicinity of the portion where two-cell comparison is not applicable as shown in FIG. 6, one of the two-cell comparison images is present in the portion where two-cell comparison is applicable and the possibility to make two-cell comparison is increased accordingly. In the above description, the number of the two-chip comparison images is assumed to be one, but, generally, a plurality of images can be set up also for the two-chip comparison images.

According to the present invention as above described, detection of a pattern defect can be performed with the two-chip comparison and the two-cell comparison automatically switched, with the coordinate not specified. Therefore, the requirement for specifying the coordinate for the portion where two-cell comparison is applicable, which has so far had to be specified for each product type of the wafer, is eliminated. Further, since two-cell comparison and two-chip comparison are respectively performed in the portion where two-cell comparison is applicable and the portion where two-cell comparison is not applicable, the detection of a pattern defect can be carried out using suitable defect detecting threshold values.

A block diagram of a system for another principle of pattern recognition according to the present invention is shown in FIG. 37. The system includes a detection device 102 for detecting a pattern on a wafer 101 as the object of inspection, a storage device 103 for storing the detected pattern, an alignment device 104 for aligning the pattern detected and stored in the preceding step with the currently detected pattern, candidate shift-for alignment selection device 105 for selecting a plurality of candidate positional shifts allowing the two patterns in alignment to provide images with a high degree of agreement, an error image extraction device 106 for calculating, for each pixel, errors between the two images at all of the selected candidates using values at the candidates and values in the vicinity of each pixel to thereby generate an error image, and defect recognition device 107 for recognizing a defect in the pattern depending on the error image. The error image extraction device 106 may arrange to select the minimum of the values at the candidates.

Figure 39A:
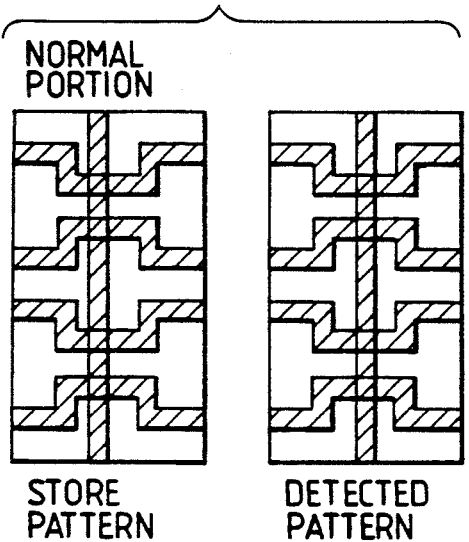

The operation of the system of FIG. 37 will be described taking, as examples, the cases where the system is applied to the patterns of FIG. 39(a) and FIG. 39(b). In the case of FIG. 39(a), a plurality of candidate shifts for alignment are searched for within the range of image shifts of 2 pixels in the vicinity of the best aligned position. An example of sum totals of differences in the overall image at each of the shifted positions is shown in Table 1.

TABLE 1

| | Errors in Normal Portion | | |
| --- | --- | --- | --- |
| | | X | |
| Y | −1 | 0 | 1 |
| −1 | 166 | 161 | 164 |
| 0 | 94 | 43 | 40 |
| 1 | 166 | 161 | 164 |

Figure 39C:
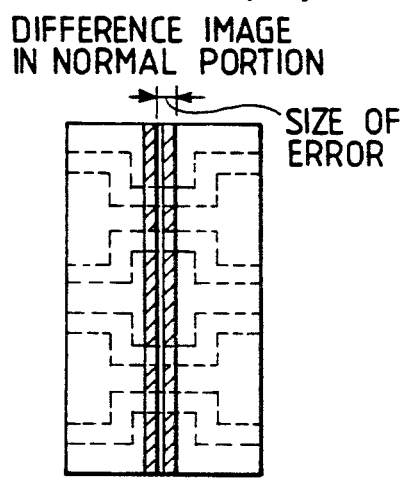
Figure 40A:
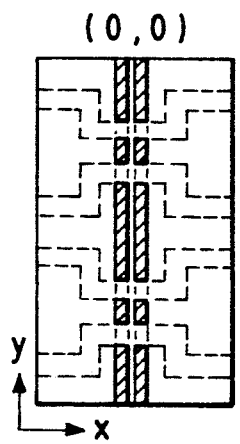
FIGS. 40(a) and 40(b) are difference images obtained at candidate shifts for alignment.
Figure 40B:
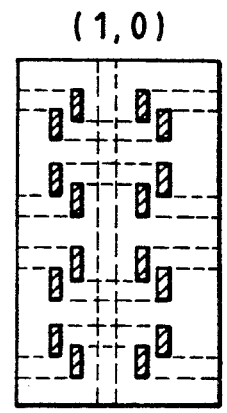

Here, the sum totals at the shifts (0, 0) and (1, 0) is small and, hence, these shifts become the candidate shifts for alignment. The difference images at the two candidates become as shown in FIGS. 40(a) and 40(b) and the minimum errors at the two candidate becomes zero at all of the pixels with FIG. 39(c) showing the difference image in the normal portion.

Figure 39B:
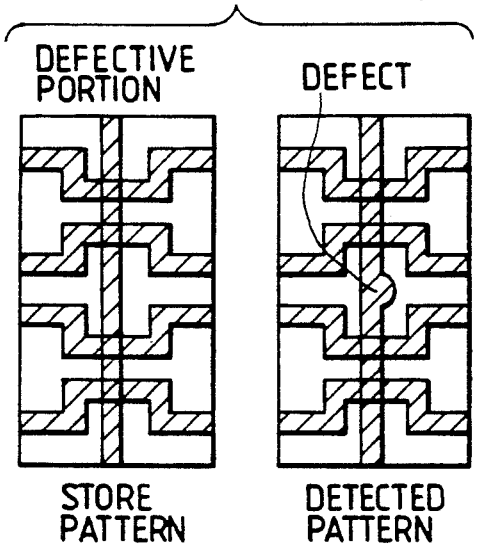
Figure 39D:
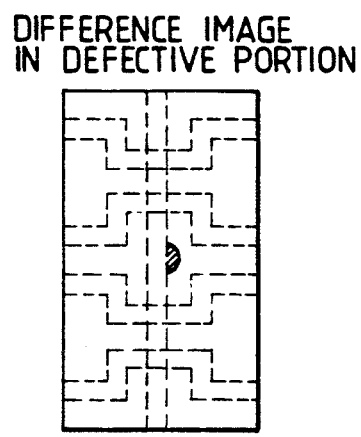

An example of sum totals in the case of FIG. 39(b) is shown in Table 2, in which the sum totals are large at all the shifts except (0, 0) and, hence, only (0, 0) becomes the candidate and the error image becomes the same as FIG. 39(d). From these results, a defect can be recognized as the position where the area of difference is large.

TABLE 2

| | Defective Portion | | |
| --- | --- | --- | --- |
| | | X | |
| Y | −1 | 0 | 1 |
| −1 | 152 | 109 | 154 |
| 0 | 83 | 2 | 87 |
| 1 | 152 | 109 | 154 |

As shown in the above examples, in the case of a normal portion having like error in an adjacent position to the position in question, the positions eliminating the error become the candidate shifts for alignment. When, there is no such an error in an adjacent position to the position in question, the position does not become the candidate shift for alignment and, as a result, only a defect appears in the error image.

As the method for deciding the candidate shifts for alignment, it is practicable to select positions where the total sum of differences is smaller than twice the sum total of differences at the best aligned position to thereby select the images with a high degree of agreement. The alignment device 104 may be omitted and the candidate shift-for-alignment selection device 105 selecting a plurality of candidate shifts for alignment may be caused also to search for the best aligned position.

Another embodiment of the present invention will be described below with reference to FIG. 41 in which the method for pattern recognition of the present invention is applied to inspection of a defect in a pattern on an LSI wafer, but the same can, of course, be applied to that in a pattern of TFT and the like. FIG. 41 is a block diagram of an apparatus for pattern recognition on an LSI wafer (hereinafter briefly referred to as "apparatus") for practicing the method. The apparatus comprises a detection portion 102A including an X-Y stage 108 for scanning a wafer 101, an illuminating light source 109 and an illuminating optical system 110 for illuminating the wafer, and an objective lens 111 and a linear image sensor 112 for detecting an optical image of the illuminated wafer, an image input portion 115 including an A/D converter 113 and an image memory portion 114 for digitizing and storing the signal from the linear image sensor 112, an image processing portion 123 including a matching portion 11 for calculating matching values, given by a later described expression (8), from a detected image 116 input to the image input portion 115 and a comparison image 117 from the image memory portion 114, a calculation portion 119 for obtaining the best aligned position and a plurality of candidate shifts for alignment, an error image extraction portion 121 for extracting an error image 120 from the detected image 116 and the comparison image 117 using the candidate shifts for alignment from the calculation portion 119, and a defect determination portion 122 binarizing the error image 120 to extract various feature parameters at the position where the difference is present, thereby determining existence of a defect, and an overall control portion 124 including a computer for performing control of the X-Y stage 108, storage and display of defect information output from the image processing portion 123, and management of the overall sequence.

After all portions are initialized upon issuance of an instruction from the overall control portion 124, the pattern on the wafer 101 illuminated by the illuminating light source 109 is detected by the linear image sensor 112 through the objective lens 111, in synchronism with the scanning of the X-Y stage 108, and thereby photo-electrically transduced into a two-dimensional pattern, which is then converted by the A/D converter 113 into the digitized two-dimensional detected image 116 and the thus obtained detected image is stored into the image memory portion 114. Matching values are obtained by the matching portion 118 from the detected image 116 and the comparison image 117 stored in the image memory portion 114.

Figure 42:
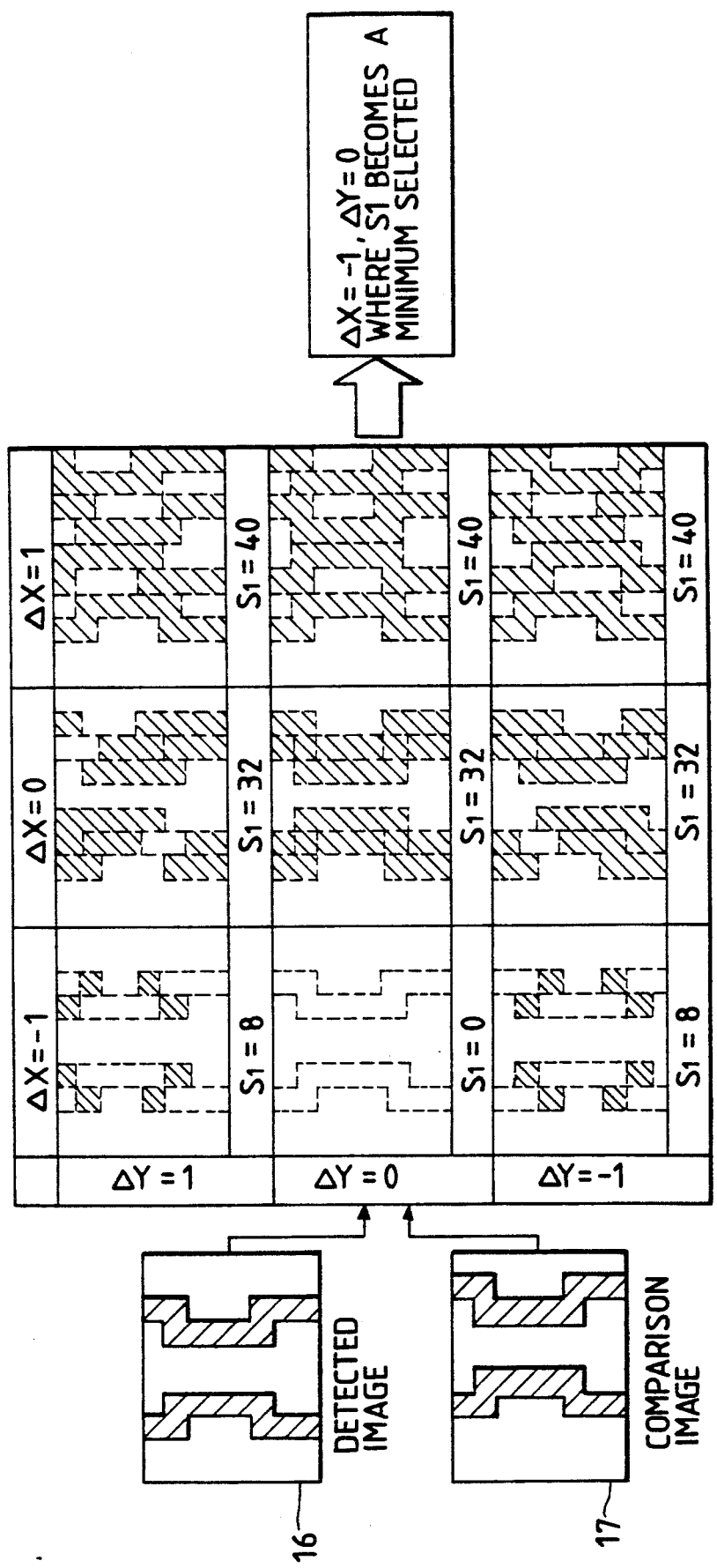
FIG. 42 is a diagram of difference images at various positional shifts for explaining a matching portion.

The above-identified operation will be described with reference to FIG. 42 which shows the operating principle of the matching portion 118. From the detected image 116 and the comparison image 117, the differences between the detected image 116 and the comparison image 117 with this comparison image 117 shifted in the directions of ΔX and ΔY by ±δ pixels, i.e., the positional discrepancy tolerance (δ=1 is assumed in the present embodiment, but this value is such that is to be determined depending on dimensional accuracy of the object of inspection and the positioning accuracy of the defect detecting apparatus and a suitable value may be established according to the need) are calculated from expression (8), to output the differences between the images corresponding to the various shift amounts as the matching values S1, $$S1(\Delta i, \Delta j) = \Sigma\Sigma |f(i, j) - g(i+\Delta i, j+\Delta j)| \qquad (8)$$

where f(i, j) represents the value of the detected image 116 at a pixel (i, j), g(i, j) represents the value of the comparison image 117 at the pixel (i, j), and S1(Δi, Δj) represent the differences between these images at the image shift amounts (Δi, Δj). Further, ΣΣ indicates summation performed over all the area of images where the positional shifts are calculated and Δi and Δj are adapted to be from −1 to +1 in the case of FIG. 42.

The calculation portion 119 obtains the minimum value Smin of S1(Δi, Δj) and the best aligned position (Δim, Δjm) as the set of (Δi, Δj) at which the above minimum value is obtained. Then, the same obtains a plurality of candidate shifts for alignment (Δis, Δjs), s=1, 2, ... as sets of (Δi, Δj) satisfying conditional expression (9), $$S1(\Delta i, \Delta j) < Smin \times Th \qquad (9)$$

where Th is a preset threshold value taking a value of about 2.

The error image extraction portion 121 obtains the error image 120 (h(i, j)) depending on the plurality of candidate shifts for alignment (Δis, Δjs) from the calculation portion 119 according to expression (10), $$h(i, j) = \text{Min}(s = 1, 2, \ldots) \quad (10)$$
$$\{|f(i, j) - g(i + \Delta is, j + \Delta js)|\}$$

The defect determination portion 22 binarizes the error image 20 with a threshold value Vth for defect determination, and extracts various feature parameters such as area, width, projected length at the position where the difference is present and, thereby, determines existence of a defect. Thus, a normal pattern with an error and a defect can be easily distinguished and, hence, such an effect is obtained that a defect smaller in size than the allowable error in the normal portion can be recognized.

As a variation of the present embodiment, the following arrangements can be considered. First, the arrangement in which a function of Smin, i.e., Smin x Smin x Th, for example, is used in place of Smin x Th of expression (9) is practicable. According to this variation, the degree of freedom can be increased, that is, a threshold value which, in the present case, is lowered in level when the value Smin is small and, hence, the degree of agreement is high and raised in level in the case to the contrary and, thereby, the quality of image can be provided.

Second, an arrangement is practicable in which, after the stored pattern and the detected pattern have been aligned, a plurality of candidate shifts for alignment are obtained from a narrower range than the current range of alignment. In this case, since the range to obtain the candidate shifts therefrom is narrow, the scale of the circuit at this portion becomes small. The alignment is in general practice today, and therefore, there is an advantage that the method of the present invention can be introduced into such apparatus with a minimum of additional components required.

Third, an arrangement in which expression (11) is used instead of expression (10) for obtaining the minimum value is practicable. That is, if there are present values $\{f(i, j) - g(i + \Delta is, j + \Delta js)\}$ whose signs are opposite, then $$h(i, j) = \text{Min}(s = 1, 2, \ldots) \quad (11)$$
$$\{|f(i, j) - g(i + \Delta is, j + \Delta js)|\} = 0$$

In this case, the presence of the values of opposite signs means that there is the value 0 somewhere, measured in the unit less than one pixel, and therefore, an advantage is obtained that an accurate evaluation can be made.

Fourth, such an arrangement is possible in which, instead of having a two-dimensional pattern detected through photoelectric transfer by a linear image sensor 112 in synchronism with scanning of an X-Y stage 108, a two-dimensional pattern is detected through photoelectric transfer by a TV camera with the X-Y stage 108 step-moved. A sensor of another type, e.g., a point type sensor such as a photomultiplier and a scanning mechanism may also be used instead of a linear image sensor 112.

Fifth, such an arrangement is possible in which, instead of calculating the matching value between the detected image 116 and the comparison image 117 according to expression (8), filters are applied to both the detected image 116 and the comparison image 117 to extract edges therefrom, and then, the matching value is calculated according to expression (8) with respect to the edge images, or filters are applied to both the detected image 116 and the comparison image 117 to binarize edges, and then, the matching value with respect to the binarized edge images is calculated according to expression (8). By virtue of the edges used in such a variation, an advantage is obtained that an adverse effect due to a difference in brightness of the pattern between the detected image and the comparison image can be lessened.

Figure 43:
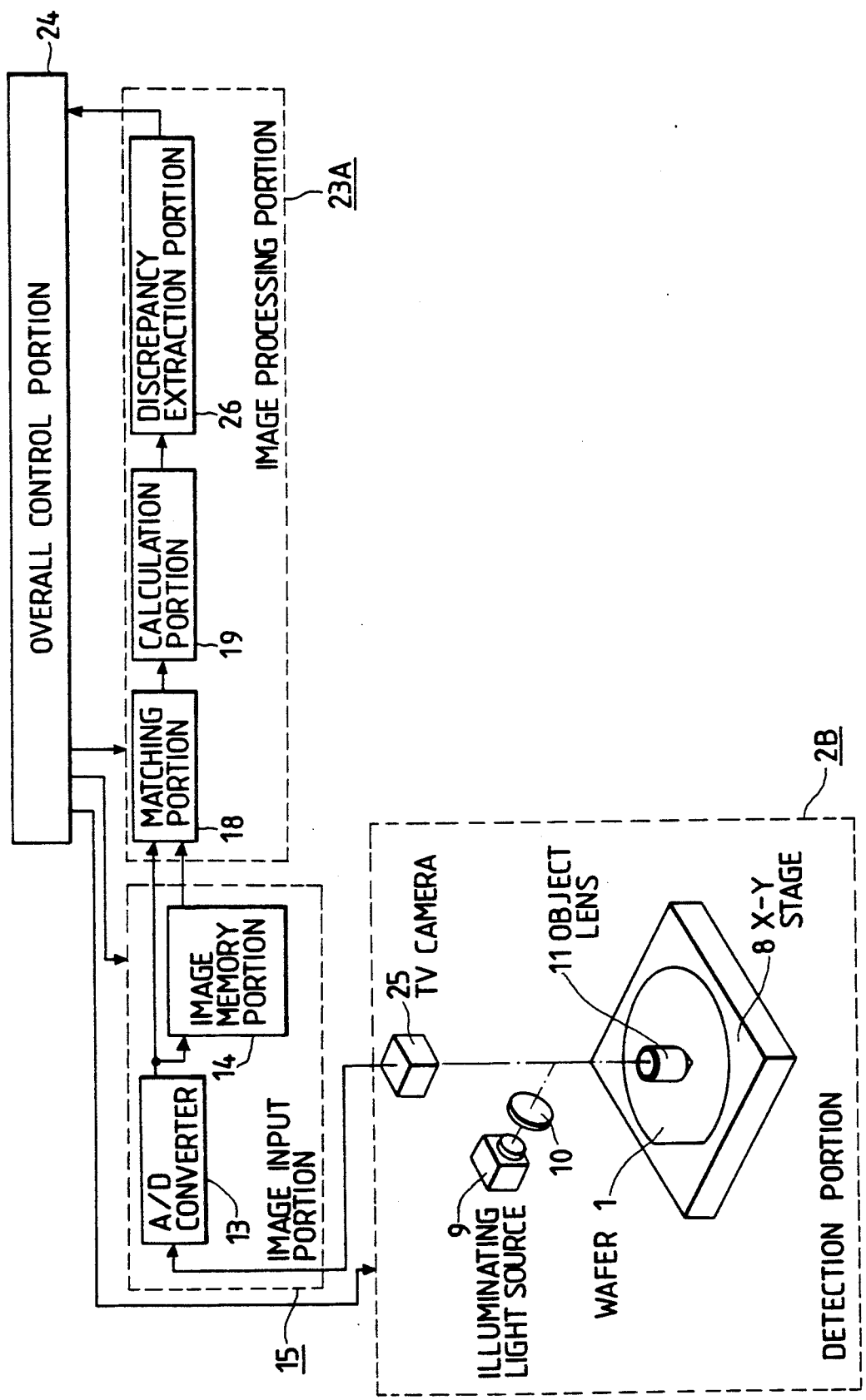
FIG. 43 is a block diagram of a further embodiment in accordance with the present invention.

Another embodiment of the present invention will be described below with reference to FIG. 43 in which the method of pattern recognition is applied to measurement of a discrepancy in a pattern on an LSI wafer, but the method can of course be applied to patterns of TFT and the like. FIG. 43 is a block diagram of an apparatus for pattern recognition (hereinafter briefly referred to as "apparatus") for LSI wafers used in the present embodiment. The apparatus comprises a detection portion 102B including up of an X-Y stage 108 for scanning a wafer 101, an illuminating light source 109 and an illuminating optical system 110 for illuminating the wafer, and an objective lens 111 and a TV camera 125 for detecting an optical image of the illuminated wafer, an image input portion 115 including an A/D converter 113 and an image memory portion 114 for digitizing and storing the signal from the TV camera 125, an image processing portion 123A including a matching portion 118 for calculating matching values, given by expression (8), from a detected image 116 input to the image input portion 115 and a comparison image 117 from the image memory portion 114, a calculation portion 119 for obtaining the best aligned position and a plurality of candidate shifts for alignment, and a discrepancy extraction portion 126 for obtaining a discrepancy amount, and an overall control portion 124 including a computer for performing control of the X-Y stage 108, storage and display of the discrepancy information output from the image processing portion 123A, and management of the overall sequence.

The apparatus operates in the following manner to measure the pattern discrepancy amount. After all parts are initialized upon issuance of an instruction from the overall control portion 124, the X-Y stage 108 is placed in position, the pattern on the wafer 101 illuminated by the illuminating light source 109 is detected by the TV camera 125 through the objective lens 111 and thereby photoelectrically transduced into a two-dimensional pattern, which is then converted by the A/D converter 113 into the digitized two-dimensional detected image 11 and the thus obtained detected image is stored into the image memory portion 114. Matching values are obtained by the matching portion 118 from the detected image 116 and the comparison image 117 stored in the image memory portion 114. This operation for obtaining the matching values is the same as that described in the preceding embodiment and is performed using the earlier mentioned expression (8).

The calculation portion 119 obtains, the same as in the preceding embodiment, the minimum value Smin of S1(Δi, Δj) in the expression (8) and the best aligned position (Δim, Δjm) as the set of (Δi, Δj) at which the above minimum value is obtained. Then, the same obtains a plurality of candidate shifts for alignment (Δis, $\Delta js$), s=1, 2, ... as sets of ($\Delta i$, $\Delta j$) satisfying the earlier mentioned expression (9).

The discrepancy extraction portion 126 outputs values S1($\Delta i$, $\Delta j$) in an ascending order from the smallest one.

According to the present embodiment, an effect is obtained that such features of patterns as a discrepancy between patterns of multiple layers overlapped at different positional shifts and the amount of deformation can be recognized. Further, according to the present invention, such effects are obtained that distinction between a normal pattern with an error and a defect can be easily made and pattern features such as pattern discrepancy and deformation can be recognized using such information as obtained by a transmission electron microscope.

While we have shown and described several embodiments in accordance with the present invention, it is understood that the same is not limited thereto but is susceptible to numerous changes and modifications as known to one of ordinary skill in the art and we therefore do not wish to be limited to the details shown and described herein but intend to cover all such modifications as are encompassed by the scope of the appended claims.

What is claimed is:

1. A method for detecting a defect in a circuit pattern comprising the steps:
   detecting a gray image signal from each of a plurality of circuit patterns as objects of inspection, which circuit patterns have been fabricated so as to be identical with one another; and
   detecting a defect as a difference of edge position between two circuit patterns by comparing the detected gray image signal of one circuit pattern with the detected gray image signal of another circuit pattern.

2. A method according to claim 1, wherein the step of detecting a defect includes obtaining a difference of the comparing of the detected gray image signals and detecting a defect in accordance with the difference.

3. A method according to claim 2, wherein the step of detecting a defect includes obtaining a difference of gray image signals having a larger value at a normal portion than a value at a defect portion.

4. A method according to claim 1, wherein the step of detecting a defect includes comparing polarities of the gray image signals to detect a defect.

5. A method according to claim 4, wherein the step of detecting a defect includes subjecting the gray image signals to differentiation processing to provide differentiated signals and, comparing polarities of the differentiated signals with each other.

6. A method according to claim 5, wherein the differentiation processing is linear differentiation processing providing linear derivatives.

7. A method according to claim 6, wherein comparison of polarities of the linear derivatives as the differentiated signals is performed only for image signals having linear derivatives with absolute values larger than a preset value.

8. A method according to claim 5, wherein the differentiation processing includes linear differentiation processing providing linear derivatives and second differentiation processing providing second derivatives, and the comparing of polarities of the linear derivatives is performed in regions obtained in accordance with the second derivatives.

9. A method according to claim 5, wherein the step of detecting a defect includes comparing, in an edge region, polarities of the differentiated signals with each other and obtaining, in a non-edge region, difference image signals between the compared gray image signals, and binarizing the difference image signals with a predetermined threshold value.

10. A method according to claim 5, wherein the step of detecting a defect includes aligning the gray image signals with each other at a position where the number of pixels disagreeing in polarity is at a minimum, and comparing the aligned gray image signals with each other.

11. A method according to claim 5, wherein the step of detecting a defect includes aligning the gray image signals with each other at a plurality of positions where the number of pixels disagreeing in polarity is less than a preset value, detecting difference image signals between the gray image signals aligned with each other at the plurality of positions, and binarizing the difference image signals with a predetermined threshold value.

12. A method according to claim 5, wherein the step of detecting a defect includes aligning the gray image signals with each other at a plurality of positions where the number of pixels disagreeing in polarity is less than a preset value, and comparing the polarity signals aligned at the plurality of positions.

13. A method according to claim 5, wherein the step of detecting a defect includes aligning the gray image signals with each other at a plurality of positions where the number of pixels disagreeing in polarity is less than a preset value, and comparing the polarity signals aligned at the plurality of positions so as to detect a polarity disagreement common at a plurality of positions as the defect.

14. An apparatus for detecting a defect in a circuit pattern comprising:
   means for detecting a gray image signal from each of a plurality of circuit patterns as objects of inspection, which circuit patterns have been fabricated so as to be identical with one another; and
   means for detecting a defect as a difference of edge position between two circuit patterns by comparing the detected gray image signal of one circuit pattern with the detected gray image signal of another circuit pattern.

15. An apparatus according to claim 14, wherein the means for detecting a defect includes comparison means for comparing the gray image signals and obtaining a difference of the comparison, and means for detecting a defect in accordance with the difference.

16. An apparatus according to claim 15, wherein means for detecting a defect includes means for obtaining a difference of gray image signals having a larger value at a normal portion than a value at a defect portion.

17. An apparatus according to claim 14, wherein the means for detecting a defect includes comparison means for comparing polarities of the gray image signals to detect a defect.

18. An apparatus according to claim 17, wherein the means for detecting a defect includes differentiating means for subjecting the gray image signals to differentiation processing to provide differentiated signals and means for comparing polarities of the differentiated signals with each other.

19. An apparatus according to claim 18, wherein the differentiation means is a linear differentiation means providing linear derivatives.

20. An apparatus according to claim 19, wherein the comparison means effects comparison of the linear derivatives as the differentiated signals only for image signals having linear derivatives with absolute values larger than a preset value.

21. An apparatus according to claim 18, wherein the differentiation means includes linear differentiation means and second differentiation means and the comparison means effects comparing of polarities of the linear derivatives in regions obtained in accordance with the second derivatives.

22. An apparatus according to claim 18, wherein the means for detecting a defect includes the comparison means comparing, in an edge region, the polarities of the differentiated signals with each other and obtaining, in a non-edge region, difference image signals between gray image signals, and means for binarizing the difference image signals with a predetermined threshold value.

23. An apparatus according to claim 18, wherein the means for detecting a defect includes aligning means for aligning the gray image signals with each other at a position where the number of pixels disagreeing in polarity is at a minimum, and the comparison means comparing the aligned image signals with each other.

24. An apparatus according to claim 18, wherein the means for detecting a defect includes aligning means for aligning the gray image signals with each other at a plurality of positions where the number of pixels disagreeing in polarity is less than a preset value, means for detecting difference image signals between the gray image signals aligned with each other at the plurality of positions, and means for binarizing the difference image signals with a predetermined threshold value.

25. An apparatus according to claim 18, wherein the means for detecting a defect includes aligning means for aligning the gray image signals with each other at a plurality of positions where the number of pixels disagreeing in polarity is less than a preset value, and the comparison means comparing the polarity signals aligned at the plurality of positions.

26. An apparatus according to claim 18, wherein the means for detecting a defect includes aligning means for aligning the gray image signals with each other at a plurality of positions where the number of pixels disagreeing in polarity is less than a preset value, and the comparison means comparing the polarity signals aligned at the plurality of positions so as to detect a plurality disagreement common at a plurality of positions as the defect.

* * * * *